(12) United States Patent
Farmer et al.

(10) Patent No.: US 10,273,233 B2
(45) Date of Patent: Apr. 30, 2019

(54) INHIBITORS OF INFLUENZA VIRUSES REPLICATION

(71) Applicant: Vertex Pharmaceuticals Incorporated, Boston, MA (US)

(72) Inventors: Luc J. Farmer, Montreal (CA); Michael John Boyd, Sharon, MA (US); Dean Shannon, Richibucto Road (CA); Michael Waldo, Grafton, MA (US); Kwame W. Nti-Addae, Tewksbury, MA (US); Yuegang Zhang, Wayland, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 15/807,984

(22) Filed: Nov. 9, 2017

(65) Prior Publication Data

US 2018/0065963 A1     Mar. 8, 2018

Related U.S. Application Data

(63) Continuation of application No. PCT/US2016/031713, filed on May 11, 2016.

(60) Provisional application No. 62/160,637, filed on May 13, 2015.

(51) Int. Cl.
   *C07D 471/04*     (2006.01)
   *A61K 31/506*     (2006.01)
   *A61K 31/4965*    (2006.01)
   *A61K 45/06*      (2006.01)

(52) U.S. Cl.
   CPC ........ *C07D 471/04* (2013.01); *A61K 31/4965* (2013.01); *A61K 31/506* (2013.01); *A61K 45/06* (2013.01); *C07B 2200/13* (2013.01)

(58) Field of Classification Search
   CPC ... C07D 471/04; C07D 403/04; A61K 31/506
   USPC .......................................... 544/328; 514/256
   See application file for complete search history.

(56) References Cited

U.S. PATENT DOCUMENTS

| | | |
|---|---|---|
| 4,349,552 A | 9/1982 | Takaya et al. |
| 5,051,412 A | 9/1991 | Macor |
| 5,304,121 A | 4/1994 | Sahatjian |
| 5,338,849 A | 8/1994 | Festal et al. |
| 5,395,840 A | 3/1995 | Miller et al. |
| 5,886,026 A | 3/1999 | Hunter et al. |
| 6,099,562 A | 8/2000 | Ding et al. |
| 6,169,181 B1 | 1/2001 | Romines et al. |
| 6,265,403 B1 | 7/2001 | Fraley et al. |
| 6,313,126 B1 | 11/2001 | Mewshaw et al. |
| 6,699,883 B1 | 3/2004 | Doemling et al. |
| 6,825,190 B2 | 11/2004 | Moon et al. |
| 6,900,201 B2 | 5/2005 | Noe et al. |
| 7,041,687 B2 | 5/2006 | Binch et al. |
| 7,135,550 B2 | 11/2006 | Come et al. |
| 7,432,375 B2 | 10/2008 | Graczyk et al. |
| 7,491,730 B2 | 2/2009 | Forster et al. |
| 7,507,826 B2 | 3/2009 | Salituro et al. |
| 7,514,448 B2 | 4/2009 | Green et al. |
| 7,645,769 B2 | 1/2010 | Khan et al. |
| 7,659,283 B2 | 2/2010 | Collier et al. |
| 7,700,609 B2 | 4/2010 | Jimenez et al. |
| 7,767,816 B2 | 8/2010 | Farmer et al. |
| 7,795,259 B2 | 9/2010 | Binch et al. |
| 7,872,129 B2 | 1/2011 | Forster et al. |
| 8,017,619 B2 | 9/2011 | Jimenez et al. |
| 8,017,781 B2 | 9/2011 | Brenchley et al. |
| 8,101,770 B2 | 1/2012 | Charrier et al. |
| 8,163,917 B2 | 4/2012 | Farmer et al. |
| 8,173,635 B2 | 5/2012 | Jimenez et al. |

(Continued)

FOREIGN PATENT DOCUMENTS

| | | |
|---|---|---|
| EP | 0557171 | 8/1993 |
| EP | 1748829 | 7/2007 |

(Continued)

OTHER PUBLICATIONS

International Search Report issued for PCT Application No. PCT/US2016/031713 Sated Sep. 20, 2016.

(Continued)

*Primary Examiner* — Charanjit Aulakh

(74) *Attorney, Agent, or Firm* — Honigman LLP; Andrew N. Weber; Jonathan P. O'Brien

(57) ABSTRACT

Polymorphic forms of Compound (1) or a pharmaceutically acceptable salt thereof, wherein Compound (1) is represented by the following structural formula:

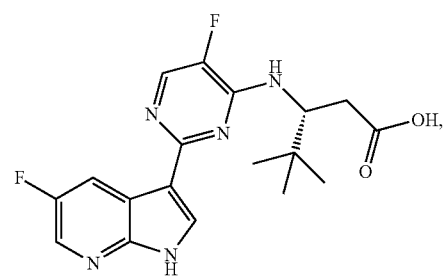

include Hydrate 2 of Compound (1), Hydrate 3 of Compound (1), Form A of Compound (1), Form B of Compound (1), Form C of Compound (1), Form D of Compound (1), and amorphous Compound (1). Such polymorphic forms are useful for treating influenza, inhibiting the replication of influenza viruses, or reducing the amount of influenza viruses in a biological sample or in a subject.

47 Claims, 18 Drawing Sheets

(56) References Cited

U.S. PATENT DOCUMENTS

| | | |
|---|---|---|
| 8,188,281 B2 | 5/2012 | Salituro et al. |
| 8,242,272 B2 | 8/2012 | Jimenez et al. |
| 8,247,421 B2 | 8/2012 | Mortimore et al. |
| 8,288,400 B2 | 10/2012 | Jimenez et al. |
| 8,338,597 B2 | 12/2012 | Charrier et al. |
| 8,367,697 B2 | 2/2013 | Jimenez et al. |
| 8,372,835 B2 | 2/2013 | Binch et al. |
| 8,445,681 B2 | 5/2013 | Brenchley et al. |
| 8,450,489 B2 | 5/2013 | Farmer et al. |
| 8,461,149 B2 | 6/2013 | Pierard et al. |
| 8,501,446 B2 | 8/2013 | Salituro et al. |
| 8,507,687 B2 | 8/2013 | Keshavarz-Shokri et al. |
| 8,513,414 B2 | 8/2013 | Tanoury et al. |
| 8,518,953 B2 | 8/2013 | Pierce et al. |
| 8,530,489 B2 | 9/2013 | Mortimore et al. |
| 8,541,445 B2 | 9/2013 | Jimenez et al. |
| 8,563,530 B2 | 10/2013 | Chang et al. |
| 8,563,576 B2 | 10/2013 | Brenchley et al. |
| 8,569,337 B2 | 10/2013 | Jimenez et al. |
| 8,580,802 B2 | 11/2013 | Salituro et al. |
| 8,598,361 B2 | 12/2013 | Jimenez et al. |
| 8,722,889 B2 | 5/2014 | Salituro et al. |
| 8,796,453 B2 | 8/2014 | Tanoury et al. |
| 8,822,681 B2 | 9/2014 | Farmer et al. |
| 8,829,007 B2 | 9/2014 | Charifson et al. |
| 8,946,425 B2 | 2/2015 | Tanoury et al. |
| 8,987,454 B2 | 3/2015 | Salituro et al. |
| 9,051,319 B2 | 6/2015 | Charifson et al. |
| 9,090,614 B2 | 7/2015 | Tanoury et al. |
| 9,120,790 B2 | 9/2015 | Farmer et al. |
| 9,296,727 B2 | 3/2016 | Charrier et al. |
| 9,345,708 B2 | 5/2016 | Charifson et al. |
| 9,394,302 B2 | 7/2016 | Charifson et al. |
| 9,518,056 B2 | 12/2016 | Charifson et al. |
| 9,771,361 B2 | 9/2017 | Nti-Addae et al. |
| 9,808,459 B2 | 11/2017 | Charifson et al. |
| 9,908,878 B2 | 3/2018 | Charifson et al. |
| 10,039,762 B2 | 8/2018 | Charifson et al. |
| 2002/0052386 A1 | 5/2002 | Armistead et al. |
| 2002/0065270 A1 | 5/2002 | Moriarty et al. |
| 2002/0147189 A1 | 10/2002 | Cai et al. |
| 2002/0183329 A1 | 12/2002 | Gross et al. |
| 2002/0183352 A1 | 12/2002 | Stack et al. |
| 2002/0183353 A1 | 12/2002 | Stack et al. |
| 2002/0183354 A1 | 12/2002 | Tran et al. |
| 2002/0193400 A1 | 12/2002 | Husbands et al. |
| 2003/0078268 A1 | 4/2003 | Zhao et al. |
| 2003/0100579 A1 | 5/2003 | Gross et al. |
| 2003/0153560 A1 | 8/2003 | Salituro et al. |
| 2003/0166668 A1 | 9/2003 | Zandt et al. |
| 2004/0009968 A1 | 1/2004 | Binch et al. |
| 2004/0009996 A1 | 1/2004 | Moon et al. |
| 2004/0043388 A1 | 3/2004 | Come et al. |
| 2004/0044203 A1 | 3/2004 | Wittman et al. |
| 2004/0236110 A1 | 11/2004 | Ladouceur et al. |
| 2005/0137201 A1 | 6/2005 | Aronov et al. |
| 2005/0148603 A1 | 7/2005 | Jimenez et al. |
| 2005/0208582 A1 | 9/2005 | Ohi et al. |
| 2005/0228005 A1 | 10/2005 | Moon et al. |
| 2005/0288290 A1 | 12/2005 | Borzilleri et al. |
| 2006/0003968 A1 | 1/2006 | Green et al. |
| 2006/0004014 A1 | 1/2006 | Hoffmann et al. |
| 2006/0122185 A1 | 6/2006 | Green et al. |
| 2006/0122213 A1 | 6/2006 | Pierard et al. |
| 2006/0183761 A1 | 8/2006 | Ledeboer et al. |
| 2006/0183900 A1 | 8/2006 | Huang et al. |
| 2006/0183911 A1 | 8/2006 | Charrier et al. |
| 2006/0258662 A1 | 11/2006 | Binch et al. |
| 2007/0043063 A1 | 2/2007 | Salituro et al. |
| 2007/0049615 A1 | 3/2007 | Ibrahim et al. |
| 2007/0066641 A1 | 3/2007 | Ibrahim et al. |
| 2007/0072896 A1 | 3/2007 | Khan et al. |
| 2007/0135466 A1 | 6/2007 | Ledeboer et al. |
| 2007/0203142 A1 | 8/2007 | Farmer et al. |
| 2007/0207995 A1 | 9/2007 | Salituro et al. |
| 2007/0213327 A1 | 9/2007 | Collier et al. |
| 2008/0242663 A1 | 10/2008 | Ashton et al. |
| 2008/0300267 A1 | 12/2008 | Okram et al. |
| 2009/0048250 A1 | 2/2009 | Aronov et al. |
| 2009/0088445 A1 | 4/2009 | Ledeboer et al. |
| 2009/0118278 A1 | 5/2009 | Forster et al. |
| 2009/0176763 A1 | 7/2009 | Salituro et al. |
| 2009/0291937 A1 | 11/2009 | Jimenez et al. |
| 2010/0069629 A1 | 3/2010 | Shimma et al. |
| 2010/0099686 A1 | 4/2010 | Charrier et al. |
| 2010/0120792 A1 | 5/2010 | Ivashchenko et al. |
| 2010/0189773 A1 | 7/2010 | Mortimore et al. |
| 2010/0280026 A1 | 11/2010 | Jimenez et al. |
| 2010/0311743 A1 | 12/2010 | Farmer et al. |
| 2011/0081364 A1 | 4/2011 | Binch et al. |
| 2011/0224197 A1 | 9/2011 | Henkle et al. |
| 2011/0263575 A1 | 10/2011 | Pierard et al. |
| 2012/0010197 A1 | 1/2012 | Charrier et al. |
| 2012/0028966 A1 | 2/2012 | Charrier et al. |
| 2012/0122879 A1 | 5/2012 | Charrier et al. |
| 2012/0136000 A1 | 5/2012 | Jimenez et al. |
| 2012/0149680 A1 | 6/2012 | Jimenez et al. |
| 2012/0165307 A1 | 6/2012 | Farmer et al. |
| 2012/0165368 A1 | 6/2012 | Brenchley et al. |
| 2012/0171245 A1 | 7/2012 | Charifson et al. |
| 2012/0178778 A1 | 7/2012 | Jimenez et al. |
| 2012/0183577 A1 | 7/2012 | Jimenez et al. |
| 2012/0184524 A1 | 7/2012 | Boyall et al. |
| 2012/0184534 A1 | 7/2012 | Brenchley et al. |
| 2012/0190699 A1 | 7/2012 | Charrier et al. |
| 2012/0258958 A1 | 10/2012 | Salituro et al. |
| 2012/0309963 A1 | 12/2012 | Mortimore et al. |
| 2013/0096302 A1 | 4/2013 | Binch et al. |
| 2013/0102782 A1 | 4/2013 | Tanoury et al. |
| 2013/0184259 A1 | 7/2013 | Charrier et al. |
| 2013/0237516 A1 | 9/2013 | Farmer et al. |
| 2013/0252939 A1 | 9/2013 | Jimenez et al. |
| 2013/0303764 A1 | 11/2013 | Tanoury et al. |
| 2013/0310418 A1 | 11/2013 | Brenchley et al. |
| 2013/0345197 A1 | 12/2013 | Salituro et al. |
| 2013/0345218 A1 | 12/2013 | Charifson et al. |
| 2014/0005192 A1 | 1/2014 | Charifson et al. |
| 2014/0005197 A1 | 1/2014 | Charifson et al. |
| 2014/0018352 A1 | 1/2014 | Pierard et al. |
| 2014/0045812 A1 | 2/2014 | Mortimore et al. |
| 2014/0094473 A1 | 4/2014 | Charifson et al. |
| 2014/0142119 A1 | 5/2014 | Charifson et al. |
| 2014/0148434 A1 | 5/2014 | Boyall et al. |
| 2014/0243273 A1 | 8/2014 | Kadiyala et al. |
| 2014/0249138 A1 | 9/2014 | Salituro et al. |
| 2014/0296201 A1 | 10/2014 | Charifson et al. |
| 2014/0309421 A1 | 10/2014 | Tanoury et al. |
| 2014/0336171 A1 | 11/2014 | Farmer et al. |
| 2015/0072982 A1 | 3/2015 | Hendricks et al. |
| 2015/0099875 A1 | 4/2015 | Charrier et al. |
| 2015/0099884 A1 | 4/2015 | Tanoury et al. |
| 2015/0152103 A1 | 6/2015 | Salituro et al. |
| 2015/0191468 A1 | 7/2015 | Charifson et al. |
| 2015/0284388 A1 | 10/2015 | Tanoury et al. |
| 2016/0008359 A1 | 1/2016 | Farmer et al. |
| 2016/0152614 A1 | 6/2016 | Charifson et al. |
| 2016/0168147 A1 | 6/2016 | Brummel et al. |
| 2016/0250213 A1 | 9/2016 | Simone et al. |
| 2016/0251353 A1 | 9/2016 | Nti-Addae et al. |
| 2016/0251354 A1 | 9/2016 | Tanoury et al. |
| 2016/0355512 A1 | 12/2016 | Charifson et al. |
| 2017/0100400 A1 | 4/2017 | Charifson et al. |
| 2018/0065962 A1 | 3/2018 | Farmer et al. |
| 2018/0155342 A1 | 6/2018 | Charifson et al. |

FOREIGN PATENT DOCUMENTS

| | | |
|---|---|---|
| JP | 2003-519143 | 6/2003 |
| JP | 2003-532635 | 11/2003 |
| JP | 2008-156370 | 7/2008 |
| WO | 1988/001997 | 3/1988 |
| WO | 1995/033748 | 12/1995 |
| WO | 1999/021859 | 5/1999 |
| WO | 2000/040554 | 7/2000 |

(56) References Cited

FOREIGN PATENT DOCUMENTS

| | | |
|---|---|---|
| WO | 2000/040581 | 7/2000 |
| WO | 2000/043393 | 7/2000 |
| WO | 2000/064898 | 11/2000 |
| WO | 2001/001986 | 1/2001 |
| WO | 2001/014374 | 3/2001 |
| WO | 2001/087887 | 11/2001 |
| WO | 2002/014317 | 2/2002 |
| WO | 2002/020013 | 3/2002 |
| WO | 2002/024636 | 3/2002 |
| WO | 2002/051837 | 7/2002 |
| WO | 2002/072587 | 9/2002 |
| WO | 2002/085896 | 10/2002 |
| WO | 2002/085911 | 10/2002 |
| WO | 2002/088129 | 11/2002 |
| WO | 2002/088131 | 11/2002 |
| WO | 2002/088135 | 11/2002 |
| WO | 2002/088136 | 11/2002 |
| WO | 2002/088140 | 11/2002 |
| WO | 2002/088144 | 11/2002 |
| WO | 2002/088146 | 11/2002 |
| WO | 2002/089811 | 11/2002 |
| WO | 2002/092602 | 11/2002 |
| WO | 2003/000688 | 1/2003 |
| WO | 2003/091246 | 11/2003 |
| WO | 2003/101968 | 12/2003 |
| WO | 2003/101990 | 12/2003 |
| WO | 2004/013140 | 2/2004 |
| WO | 2004/014912 | 2/2004 |
| WO | 2004/016609 | 2/2004 |
| WO | 2004/016610 | 2/2004 |
| WO | 2004/043388 | 5/2004 |
| WO | 2004/076454 | 9/2004 |
| WO | 2004/078756 | 9/2004 |
| WO | 2004/082638 | 9/2004 |
| WO | 2004/089913 | 10/2004 |
| WO | 2004/106298 | 12/2004 |
| WO | 2005/000813 | 1/2005 |
| WO | 2005/012304 | 2/2005 |
| WO | 2005/028475 | 3/2005 |
| WO | 2005/033072 | 4/2005 |
| WO | 2005/044181 | 5/2005 |
| WO | 2005/062795 | 7/2005 |
| WO | 2005/085244 | 9/2005 |
| WO | 2005/095400 | 10/2005 |
| WO | 2005/105213 | 11/2005 |
| WO | 2005/123736 | 12/2005 |
| WO | 2006/009755 | 1/2006 |
| WO | 2006/015123 | 2/2006 |
| WO | 2006/030031 | 3/2006 |
| WO | 2006/038001 | 4/2006 |
| WO | 2006/041773 | 4/2006 |
| WO | 2006/050076 | 5/2006 |
| WO | 2006/052913 | 5/2006 |
| WO | 2006/063167 | 6/2006 |
| WO | 2006/069258 | 6/2006 |
| WO | 2006/124863 | 11/2006 |
| WO | 2006/127587 | 11/2006 |
| WO | 2007/002325 | 1/2007 |
| WO | 2007/002433 | 1/2007 |
| WO | 2007/017145 | 2/2007 |
| WO | 2007/084557 | 7/2007 |
| WO | 2007/095188 | 8/2007 |
| WO | 2007/107221 | 9/2007 |
| WO | 2007/117494 | 10/2007 |
| WO | 2007/122410 | 11/2007 |
| WO | 2007/129195 | 11/2007 |
| WO | 2007/146057 | 12/2007 |
| WO | 2008/003958 | 1/2008 |
| WO | 2008/005457 | 1/2008 |
| WO | 2008/023159 | 2/2008 |
| WO | 2008/076392 | 6/2008 |
| WO | 2008/079346 | 7/2008 |
| WO | 2008/112642 | 9/2008 |
| WO | 2008/112646 | 9/2008 |
| WO | 2008/112651 | 9/2008 |
| WO | 2008/113711 | 9/2008 |
| WO | 2008/123800 | 10/2008 |
| WO | 2009/023269 | 2/2009 |
| WO | 2009/040556 | 4/2009 |
| WO | 2009/046983 | 4/2009 |
| WO | 2009/059943 | 5/2009 |
| WO | 2009/106442 | 9/2009 |
| WO | 2009/125395 | 10/2009 |
| WO | 2009/145814 | 12/2009 |
| WO | 2010/008454 | 1/2010 |
| WO | 2010/008459 | 1/2010 |
| WO | 2010/011756 | 1/2010 |
| WO | 2010/148197 | 12/2010 |
| WO | 2011/000566 | 1/2011 |
| WO | 2011/008915 | 1/2011 |
| WO | 2011/130146 | 10/2011 |
| WO | 2011/137022 | 11/2011 |
| WO | 2012/083121 | 6/2012 |
| WO | 2012/083122 | 6/2012 |
| WO | 2013/006634 | 1/2013 |
| WO | 2013/019828 | 2/2013 |
| WO | 2013/070606 | 5/2013 |
| WO | 2013/184985 | 12/2013 |
| WO | 2014/110259 | 7/2014 |
| WO | 2014/201332 | 12/2014 |
| WO | 2015/027005 | 2/2015 |
| WO | 2015/073476 | 5/2015 |
| WO | 2015/073481 | 5/2015 |
| WO | 2015/073491 | 5/2015 |
| WO | 2016/020526 | 2/2016 |
| WO | 2016/037953 | 3/2016 |
| WO | 2016/054309 | 4/2016 |
| WO | 2016/054312 | 4/2016 |
| WO | 2016/183116 | 11/2016 |
| WO | 2017/089518 | 6/2017 |
| WO | 2017/118680 | 7/2017 |
| WO | 2017/125506 | 7/2017 |
| WO | 2017/223231 | 12/2017 |

OTHER PUBLICATIONS

Alvarez, Mercedes et al., "Synthesis of 3-Aryl- and 3-Heteroaryl-7-azaindoles", Synthesis, Thieme Stuttgart, New York, No. 4, 1999, pp. 615-620.

Amano, Mutsuki et al., "Formation of Actin Stress Fibers and Focal Adhesions Enhanced by Rho-Kinase", Science, vol. 275, Feb. 28, 1997, pp. 1308-1311.

Amano, Mutsuki et al., "Identification of a Putative Target for Rho as the Serine-Threonine Kinase Protein Kinase N", Science vol. 271, Feb. 2, 1996, pp. 648-650.

Banfi, Luca et al., "Triisopropyl Borate", E-Eros Encyclopedia of Reagents for Organic Synthesis—2nd Edition, John Wiley & Sons, Ltd, GB, Jan. 1, 2006, pp. 10177-10179.

Bennett, J. Claide, M.D. et al., "Cecil Textbook of Medicine", W.B. Saunders Company, 20th Edition, vol. 1, 1996, pp. 1004-1010.

Berge, Stephen M. et al., "Pharmaceutical Salts'" Journal of Pharmaceutical Sciences, vol. 66, No. 1, Jan. 1977, pp. 1-19.

Bettayeb, Karima et al., "Meriolins, a New Class of Cell Death-Inducing Kinase Inhibitors with Enhanced Selectivity for Cyclin-Dependent Kinases", Cancer Research, vol. 67, No. 17, Sep. 1, 2007, pp. 8325-8334.

Biswas, Siddhartha K. et al., "Mutational Analysis of the Conserved Motifs of Influenza A Virus Polymerase Basic Protein 1", Journal of Virology, The American Society for Microbiology, Mar. 1, 1994, pp. 1819-1826.

Boysen, Mike, "Boronsäuren", ROEMPP, Jan. 2011.

Brittan, Harry G., "Methods for the Characterization of Polymorphs and Solvates", Polymorphism in Pharmaceutical Solids, 1999, whole document.

Burns, Timothy F. et al., "Silencing of the Novel p53 Target Gene Snk/Plk2 Leads to Mitotic Catastrophe in Paclitaxel (Taxol)-Exposed Cells", Molecular and cellular Biology, vol. 23, No. 16, Aug. 2003, pp. 5556-5571.

Caira, Mino R., "Crystalline Polymorphism of Organic Compounds", Topics in Current Chemistry, Springer, Berlin, DE, vol. 198, Jan. 1, 1998, pp. 163-208.

(56) References Cited

OTHER PUBLICATIONS

Catlett-Falcone, Robyn et al, "Constitutive Activation of Stat3 Signaling Confers Resistance to Apoptosis in Human U266 Myeloma Cells", Immunity, vol. 10, Jan. 1999, pp. 105-115.
Chelucci, Giorgio et al., "An easy route to optically active 1-substituted-1-pyridyl-methylamines by diastereoselective reduction of enantiopure N-tert-butanesulfinyl ketimines", Tetrahedron: Asymmetry, Elsevier, 2006, vol. 17, No. 22, pp. 3163-3169.
Chiba, Yoshihiko et al., "Augmented acetylcholine-induced translocation of RhoA in bronchial smooth muscle from antigen-induced airway hyperresponsive rats", British Journal of Pharmacology, vol. 133, 2001, pp. 886-890.
Chiba, Yoshihiko et al., "Augmented acetylcholine-induced, Rho-mediated Ca2+ sensitization of bronchial smooth muscle contraction in antigen-induced airway hyperresponsive rats", British Journal of Pharmacology, vol. 127, 1999, pp. 597-600.
Chiba, Yoshihiko et al., "Characteristics of muscarinic cholilnoceptors in airways of antigen-induced airway hyperresponsive rats", Comp. Biochem. Physiol. C Pharmacol. Toxicol. Endocrinol., vol. 111C, No. 3, 1995, pp. 351-357.
Chitaley, Kanchan et al., "Antagonism of Rho-kinase stimulates rat penile erection via a nitric oxide-independent pathway", Nature Medicine, Nature Publishing Group, vol. 7, No. 1, Jan. 2001, pp. 119-122.
Clapham, Kate M. et al., "Functionalized Heteroarylpyridazines and Pyridazin-3(2H)-one Derivatives via Palladium-Catalyzed Cross-Coupling Methodology", Journal of Organic Chemistry, vol. 73, No. 6, 2008, pp. 2176-2181.
Clark, Michael P. et al., "Discovery of a Novel, First-in-Class, Orally Bioavailable Azaindole Inhibitor (VX-787) of Influenza PB2", Journal of Medicinal Chemistry, vol. 57, No. 15, Jul. 14, 2014, pp. 6668-6678.
De Clercq, Erik, "Antiviral agents active against influenza A viruses", Nature Reviews Drug Discovery, vol. 5, Dec. 31, 2006, pp. 1015-1025.
Dymock, Brian W. et al., "Selective JAK inhibitors", Future Medicinal Chemistry, vol. 6, No. 12, 2014, pp. 1439-1471.
Eto, Masato et al., "Thrombin Suppresses Endothelial Nitric Oxide Synthase and Upregulates Endothelin-Converting Enzyme-1 Expression by Distinct Pathways", Circulation Research, vol. 89, 2001, pp. 583-590.
Eto, Yasuhiro et al., "Gene transfer of dominant negative Rho kinase suppresses neointimal formation after balloon injury in pigs", Am. J. Physiol. Heart Circ. Physiol., American Physiological Society, vol. 278, 2000, pp. H1744-H1750.
Fan, Yu et al., "Apoptosis induction with polo-like kinase-1 antisense phosph-orothioate oligodeoxynucleotide of colon cancer cell line SW480", World J. Gastroenterol, vol. 11, No. 29, 2005, pp. 4596-4599.
Fernandez, David et al., "Synthesis of Polyheterocyclic Nitrogen-Containing Marine Natural Products#", Monatshefte Fur Chemie, Chemical Monthly, AU, vol. 135, 2004, pp. 615-627.
Fournier, Alyson E. et al., "Rho Kinase Inhibition Enhances Axonal Regeneration in the Injured CNS", The Journal of Neuroscience, vol. 23, No. 4, Feb. 15, 2003, pp. 1416-1423.
Frank, David A, "STAT Signaling in the Pathogenesis and Treatment of Cancer", Molecular Medicine, vol. 5, Jul. 1999, pp. 432-456.
Fresneda, Pilar M. et al., "Synthesis of the indole alkaloids meridianins from the tunicate Aplidium meridianum", Tetrahedron, Pergamon, vol. 57, No. 12, 2001, pp. 2355-2363.
Fu, Xiahong et al., "The effects of the Rho-kinase inhibitor Y-27632 on arachidonic acid-, GTPgammaS-, and phorbol ester-induced induced Ca2+ -sensitization of smooth muscle", FEBS Letters, vol. 440, 1998, pp. 183-187.
Fukata, Yuko et al., "Rho-Rho-kinase pathway in smooth muscle contraction and cytoskeletal reorganization of non-muscle cells", Trends Pharmacological Sciences, vol. 22, No. 1, Jan. 2001, pp. 32-39.

Galli, Stephan J., MD, "New Concepts About the Mast Cell", New England Journal of Medicine, vol. 328, No. 4, 1993, pp. 257-265.
Garcia-Bustos, Jose F. et al., "PIK1, an essential phosphatidylinositol 4-kinase associated with the yeast nucleus", The EMBO Journal, vol. 13, No. 10, 1994, pp. 2352-2361.
Genda, Takuya et al., "Cell Motility Mediated by Rho and Rho-Associated Protein Kinase Plays a Critical Role in Intrahepatic Metastasis of Human Hepatocellular Carcinoma", Hepatology, vol. 30, No. 4, Oct. 1999, pp. 1027-1036.
Gonzalez, Susana et al., "Characterization of Influenza Virus PB1 Protein Binding to Viral RNA: Two Separate Regions of the Protein Contribute to the Interaction Domain", Journal of Virology, The American Society for Microbiology, vol. 73, No. 1, Jan. 1, 1999, pp. 631-637.
Gordon, John R. et al, "Mast cells as a source of both preformed and immunologically inducible TNF-alpha/cachectin", Nature, vol. 346, Jul. 19, 1990, pp. 274-276.
Guan, Ran et al., "Small Interfering RNA-Mediated Polo-Like Kinase 1 Depletion Preferentially Reduces the Survival of p53-Defective, Oncogenic Transformed Cells and Inhibits Tumor Growth in Animals", Cancer Res., vol. 65, No. 7, Apr. 1, 2005, pp. 2698-2704.
Ha, Hyung-Ho et al., "Novel heterocycle-substituted pyrimidines as inhibitors of NF-κB transcription regulation related to TNF-alpha cytokine release", Bioorganic & Medicinal Chemistry Letters, Elsevier, vol. 18, 2008, pp. 653-656.
Hamanaka, Ryoji et al., "Polo-like Kinase Is a Cell Cycle-regulated Kinase Activated during Mitosis", Journal of Biological Chemistry, vol. 270, No. 36, Sep. 8, 1995, pp. 21086-21091.
Hanks, Steven K. et al., "Protein kinases 6. The eukaryotic protein kinase superfamily: kinase (catalytic) domain structure and classification", FASEB J., vol. 9, No. 8, 1995, pp. 576-596.
Harrington, Elizabeth A. et al., "VX-680, a potent and selective small-molecule inhibitor of the Aurora kinases, suppresses tumor growth in vivo", Nature Medicine, vol. 10, No. 3, Feb. 22, 2004, pp. 262-267.
Hatanaka, Masashi. et al., "Preparation and antioxidant activity of alpha-pyridoin and its derivatives", Bioorganic & Medicinal Chemistry, Elsevier, 2005, vol. 13, pp. 6763-6770.
Herbert, R. et al., "1H-Pyrrolo[2,3-b]pyridines. Part II. Fragmentation of Some 1H-Pyrrolo[2,3-b]pyridines induced by Electron Impact", J. Chem. Soc., Phys. Org., 1970, pp. 459-463.
Hernandez-Perera, Octavio et al., "Involvement of Rho GTPases in the Transcriptional Inhibition of Preproendothelin-1 Gene Expression by Simvastatin in Vascular Endothelial Cells", Circulation Research, vol. 87, 2000, pp. 616-622.
Hiles, Ian D. et al., "Phosphatidylinositol 3-Kinase: Structure and Expression of the 110 kd Catalytic Subunit", Cell, vol. 70, No. 3, Aug. 7, 1992, pp. 419-429.
Hirose, Masaya et al., "Molecular Dissection of the Rho-associated Protein Kinase (p160ROCK)-regulated Neurite Remodeling in Neuroblastoma N1E-115 Cells", Journal of Cell Biology, vol. 141, No. 7, Jun. 29, 1998, pp. 1625-1636.
Honjo, Meguni et al., "Effects of Protein Kinase Inhibitor, HA1077 on Intraocular Pressure and Outflow Facility in Rabbit Eyes", Arch. Ophthalmol, vol. 119, Aug. 2001, pp. 1171-1178.
Hoshijima, Masahiko et al., "The Low Molecular Weight GTPase Rho Regulates Myofibril Formation and Organization in Neonatal Rat Ventricular Myocytes", The Journal of Biological Chemistry, USA, vol. 273, No. 13, Mar. 27, 1998, pp. 7725-7730.
Huang, Shenlin, et al., "Synthesis of 2-amino-4-(7-azaindol-3-yl)pyrimidines as cyclin dependent kinase 1 (CDK1) inhibitors", Bioorganic & Medicinal Chemistry Letters, Elsevier, vol. 16, 2006, pp. 4818-4821.
Hudson, J.W. et al., "Late mitotic failure in mice lacking Sak, a polo-like kinase", Current Biology, vol. 11, No. 6, Mar. 20, 2001, pp. 441-446.
Iizuka, Kunihiko et al., "Evaluation of Y-27632, a Rho-kinase inhibitor, as a bronchodilator in guinea pigs", European Journal of Pharmacology, vol. 406, No. 2, 2000, pp. 273-279.

(56) References Cited

OTHER PUBLICATIONS

Ikeda, Fusao et al., "Reduction of Hepatic Ischemia/Reperfusion-Induced Injury by a Specific ROCK/Rho Kinase Inhibitor Y-27632", Journal of Surgical Research, Elsevier Science (USA), vol. 109, 2003, pp. 155-160.
International Search Report issued for PCT Application No. PCT/US2005/010846 Dated Aug. 19, 2005.
International Search Report issued for PCT Application No. PCT/US2007/001225 Dated Jul. 20, 2007.
International Search Report issued for PCT Application No. PCT/US2007/026190 Dated May 20, 2008.
International Search Report issued for PCT Application No. PCT/US2008/009786 Dated Jan. 19, 2009.
International Search Report issued for PCT Application No. PCT/US2009/001534 Dated Apr. 2, 2010.
International Search Report issued for PCT Application No. PCT/US2010/038988 dated Aug. 20, 2010.
International Search Report issued for PCT Application No. PCT/US2012/045431 dated Feb. 5, 2013.
International Search Report issued for PCT Application No. PCT/US2012/049097 Dated Sep. 25, 2012.
International Search Report issued for PCT Application No. PCT/US2012/063712 dated Jan. 8, 2013.
International Search Report issued for PCT Application No. PCT/US2014/010876 Dated Apr. 29, 2014.
International Search Report issued for PCT Application No. PCT/US2014/051988 Dated Nov. 3, 2014.
International Search Report issued for PCT Application No. PCT/US2014/065114 Dated Jan. 29, 2015.
International Search Report issued for PCT Application No. PCT/US2014/065121 Dated Apr. 8, 2015.
International Search Report issued for PCT Application No. PCT/US2014/065144 Dated Mar. 2, 2015.
International Search Report issued for PCT Application No. PCT/US2015/053385 Dated Dec. 17, 2015.
International Search Report issued for PCT Application No. PCT/US2015/053393 Dated Dec. 15, 2015.
International Search Report issued for PCT Application No. PCT/US2016/031705 Dated Jun. 22, 2016.
IPRP issued for PCT/US2005/010846 Dated Oct. 4, 2006.
IPRP issued for PCT/US2007/001225 Dated Jul. 22, 2008.
IPRP issued for PCT/US2010/038988 dated Dec. 20, 2011.
Ishibashi, Toshiyuki et al., "Inhibition of Rho/Rho-kinase signaling downregulates plasminogen activator inhibitor-1 synthesis in cultured human monocytes", Biochimica Et Biophysica Acta, Elsevier, vol. 1590, 2002, pp. 123-130.
Ishizaki, Toshimasa et al., "p160ROCK, a Rho-associated coiled-coil forming protein kinase, works downstream of Rho and induces focal adhesions", FEBS Letters, vol. 404, No. 2, 1997, pp. 118-124.
Ishizaki, Toshimasa et al., "The small GTP-binding protein Rho binds to and activates a 160 kDa Ser/Thr protein kinase homologous to myotonic dystrophy kinase", The EMBO Journal, vol. 15, No. 8, 1996, pp. 1885-1893.
Itoh, Kazuyuki et al., "An essential part for Rho-associated kinase in the transcellular invasion of tumor cells", Nature Medicine, vol. 5, No. 2, Feb. 1999, pp. 221-225.
Jaeschke, Georg et al., "Highly Enantioselective Ring Opening of Cyclic Meso-Anhydrides to Isopropyl Hemiesters with Ti-TADDOLates: An Alternative to Hydrolytic Enzymes?", The Journal of Organic Chemistry, American Chemical Society, US, vol. 63, No. 4, Jan. 1, 1998, pp. 1190-1197.
Jiang, Jun-Jie J. et al., "Advances in the Inhibitors of Janus Kinase", Medicinal chemistry, vol. 4, No. 8, 2014, pp. 540-548.
Jorden, Danica, "World Alzheimer Day: French Doctor Denounces Routine Alzheimer Medications", ZCommunications, Sep. 22, 2015, Whole document.
Kandabashi, Tadashi, MD et al., "Inhibition of Myosin Phosphatase by Upregulated Rho-Kinase Plays a Key Role for Coronary Artery Spasm in a Porcine Model with Interleukin-1beta", Circulation, vol. 101, No. 11, Mar. 21, 2000, pp. 1319-1323.

Karpov, Alexei S. et al., "Concise Synthesis of Meridianins by Carbonylative Alkynylation and a Four-Component Pyrimidine Synthesis", Angewandte Chemie., International Edition, Wiley VCH Verlag, Weinheim, DE, vol. 44, 2005, pp. 6951-6956.
Katsumata, Naoki et al., "Enhanced Myosin Light Chain Phosphorylations as a Central Mechanism for Coronary Artery Spasm in a Swine Model With Interleukin-1beta", Circulation, vol. 96, No. 12, 1997, pp. 4357-4363.
Kelly, Terence A. et al., "Novel Non-Nucleoside Inhibitors of Human Immunodeficiency Virus Type 1 Reverse Transcriptase. 6. 2-Indo)-3-yl and 2-Azaindo1-3-yl-dipyridodiazepinones1", Journal of Medicinal Chemistry, vol. 40, No. 15, 1997, pp. 2430-2433.
Khaselev, N. et al., "The Role of the C—C Double Bond in Alcohol Elimination from MH+ Ions of Unsaturated Bicyclic Esters upon Chemical Ionization", Journal of Mass Spectrometry, vol. 30, No. 11, Nov. 1, 1995, pp. 1533-1538.
Kimura, Kazushi et al., "Regulation of Myosin Phosphatase by Rho and Rho-Associated Kinase (Rho-Kinase)", Science, vol. 273, Jul. 12, 1996,pp. 245-248.
Kirken, R. A., "Targeting Jak3 for Immune Suppression and Allograft Acceptance", Transplantation Proceedings, Elsevier, vol. 33, No. 7-8, 2001, pp. 3268-3270.
Klages, Birgit et al., "Activation of G12/G13 Results in Shape Change and Rho/Rho-Kinase-mediated Myosin Light Chain Phosphorylation in Mouse Platelets", Journal of Cell Biology, vol. 144, No. 4, Feb. 9, 1999, pp. 745-754.
Knighton, Daniel R. et al., "Crystal Structure of the Catalytic Subunit of Cyclic Adenosine Monophosphate-Dependent Protein Kinase", Science, vol. 253, Jul. 26, 1991, pp. 407-414.
Kunz, Jeannette et al., "Target of Rapamycin in Yeast, TOR2, Is an Essential Phosphatidylinositol Kinase Homolog Required for G1 Progression", Cell, vol. 73, No. 3, May 7, 1993, pp. 585-596.
Kupittayanant, S. et al., "The effects of inhibiting Rho-associated kinase with Y-27632 on force and intracellular calcium in human myometrium", Pflugers Arch—Eur J Physiol, vol. 443, 2001, pp. 112-114.
Kuwahara, Koichiro et al., "The effects of the selective ROCK inhibitor, Y27632, on ET-1-induced hypertrophic response in nenatal rat cardiac myocytes—possible involvement of Rho/ROCK pathway in cardiac muscle cell hypertrophy'" Federation of European Biochemial Societies Letters, vol. 452, 1999, pp. 314-318.
Lane, Heidi A. et al., "Antibody Microinjection Reveals an Essential Role for Human Polo-like Kinase 1 (Plk1) in the Functional Maturation of Mitotic Centrosomes", Journal of Cell Biology, vol. 135, No. 6-2, Dec. 1996, pp. 1701-1713.
Laufs, Ulrich et al., "Post-transcriptional Regulation of Endothelial Nitric Oxide Synthase mRNA Stability by Rho GTPase*", The Journal of Biological Chemistry, USA, vol. 273, No. 37, Sep. 11, 1998, pp. 24266-24271.
Leung, Thomas et al., "A Novel Serine/Threonine Kinase Binding the Ras-related RhoA GTPase Which Translocates the Kinase to Peripheral Membranes", Journal of Biological Chemistry, vol. 270, No. 49, Dec. 8, 1995, pp. 29051-29054.
Leung, Thomas et al., "The p160 RhoA-Binding Kinase ROKalpha is a Member of a Kinase Family and is Involved in the Reorganization of the Cytoskeleton", Molecular and Cellular Biology, vol. 16, No. 10, Oct. 1996, pp. 5313-5327.
Li, Jun et. al "SAK, A New Polo-Like Kinase, Is Transcriptionally Repressed by p53 and Induces Apoptosis upon RNAi Silencing", Neoplasia, vol. 7, No. 4, Apr. 2005, pp. 312-323.
Li, Wenjie et al., "An Improved Protocol for the Preparation of 3-Pyridyl- and Some Arylboronic Acids", Journal of Organic Chemistry, vol. 67, No. 15, 2002, pp. 5394-5397.
Li, Zhongkui et al., "Function of Polo-like Kinase 3 in NF-κB-mediated Proapoptotic Response", Journal of Biological Chemistry, vol. 280, No. 17, Apr. 29, 2005, pp. 16843-16850.
Liu, Xiaoqi et al., "Polo-like kinase (Plk)1 depletion induces apoptosis in cancer cells", Proc. Nat'l. Acad. Sci., USA, vol. 100, No. 10, May 13, 2003, pp. 5789-5794.
Liu, Yanbing et al., "Bis-Suzuki reactions of 2,3-dihaloindoles. A convenient synthesis of 2,3-diarylindoles", Tetrahedron Letters, vol. 41, 2000, pp. 8717-8721.

(56) References Cited

OTHER PUBLICATIONS

Lowery, Drew M. et al., "Structure and function of Polo-like Kinases", Oncogene, Nature Publishing Group, vol. 24, 2005, pp. 248-259.

M.A. Malllkobcknn, "JleKapcTBeHHble cpeAcTBa", 2001, vol. 1, p. 14.

Ma, Sheng et al., "Role of Plk2 (Snk) in Mouse Development and Cell Proliferation", Molecular and Cellular Biology, vol. 23, No. 19, Oct. 2003, pp. 6936-6943.

Macmillan, Jennifer C. et al., "Comparative Expression of the Mitotic Regulators SAK and PLK in Colorectal Cancer", Annals of Surgical Oncology, vol. 8, No. 9, 2001, pp. 729-740.

Madaule, Pascal et al., "A novel partner for the GTP-bound forms of rho and rac", FEBS Letters, vol. 377, No. 2, 1995, pp. 243-248.

Madaule, Pascal et al., "Role of citron kinase as a target of the small GTPase Rho in cytokinesis", Nature, vol. 394, Jul. 30, 1998, pp. 491-494.

Malaviya, Ravi et al., "Genetic and Biochemical Evidence for a Critical Role of Janus Kinase (JAK)-3 in Mast Cell-Mediated Type I Hypersensitivity Reactions", Biochemical and Biophysical Research Communications, vol. 257, No. 3, 1999, pp. 807-813.

Malaviya, Ravi et al., "Targeting Janus Kinase 3 in Mast Cells Prevents Immediate Hypersensitivity Reactions and Anaphylaxis", Journal of Biological Chemistry, vol. 274, No. 38, Sep. 17, 1999, pp. 27028-27038.

Martinez, Ana et al. "Glycogen Synthase Kinase 3 Inhibitors in the Next Horizon for Alzheimer's Disease Treatment", International Journal of Alzheimer's Disease, vol. 2011, 2011 pp. 1-7.

Masumoto, Akihiro et al., "Possible Involvement of Rho-kinase in the Pathogenesis of Hypertension in Humans", Hypertension, vol. 38, No. 6, Dec. 2001, pp. 1307-1310.

Masumoto, Akihiro et al., "Suppression of Coronary Artery Spasm by the Rho-Kinase Inhibitor Fasudil in Patients With Vasospastic Angina", Circulation, vol. 105, 2002, pp. 1545-1547.

Matsui, Takeshi et al., "Rho-associated kinase, a novel serine/threonine kinase, as a putative target for small GTP binding protein Rho", The EMBO Journal, vol. 15, No. 9, 1996, pp. 2208-2216.

Mills, Thomas M. et al., "Effect of Rho-kinase inhibition on vasoconstriction in the penil circulation", J. Appl. Physiol., vol. 91, 2001, pp. 1269-1273.

Miyagi, Yasushi, M.D., Ph.D. et al., "Upregulation of rho A and rho kinase messenger RNAs in the basilar artery of a rat model of subarachnoid hemorrhage", J. Neurosurg., vol. 93, No. 3, Sep. 2000, pp. 471-476.

Mizunuma, Kazuyuki et al., "Prevention of Ischemia-Reperfusion-Induced Hepatic Microcirculatory Disruption by Inhibiting Stellate Cell Contraction Using ROCK Inhibitor1", Transplantation, USA, vol. 75, No. 5, Mar. 15, 2003, pp. 579-586.

Morishige, Kunio et al., "Asenovirus-Mediated Transfer of Dominant-Negative Rho-Kinase Induces a Regression of Coronary Arteriosclerosis in Pigs In Vivo", Arterioscler. Thromb. Vasc. Biol., vol. 21, Apr. 2001, pp. 548-554.

Morissette, Sherry L. et al., "High-throughput crystallization: polymorphs, salts, co-crystals and solvates of pharmaceutical solids", Advanced Drug Delivery Reviews, vol. 56, 2004, pp. 275-300.

Mukai, Yasushi et al., "Involvement of Rho-kinase in hypertensive vascular disease: a novel therapeutic target in hypertension", The FASEB Journal, vol. 15, No. 6, Apr. 2001, pp. 1062-1064.

Müller-Ladner, Ulf et al., "Activation of the IL-4 STAT Pathway in Rheumatoid Synovium", Journal of Immunology, vol. 164, No. 4, 2000, pp. 3894-3901.

Nakagawa, Osamu et al., "ROCK-I and ROCK-II, two isoforms of Rho-associated coiled-coil forming protein serine/threonine kinase in mice", FEBS Letters, vol. 392, No. 2, 1996, pp. 189-193.

Nakazawa, Misako et al., "PA subunit of RNA polymerase as a promising target for anti-influenza virus agents", Antiviral Research, Elsevier, vol. 78, No. 3, Jan. 17, 2008, pp. 194-201.

Narayanan, A. et al., "Developments in antivirals against influenza, smallpox and hemorrhagic fever viruses", Expert Opinion on Investigational Drugs, Ashley Publications Ltd., London, GB, vol. 20, No. 2, Feb. 1, 2011, pp. 239-254.

Nemecek, Conception et al., "Design of Potent IGF1-R Inhibitors Related to Bis-azaindoles", Chemical Biology & Drug Design, vol. 76, No. 2, Aug. 9, 2010, pp. 100-106.

Nielsen, Mette et al., "Constitutive activation of a slowly migrating isoform of Stat3 in mycosis fungoides: Tyrphostin AG490 inhibits Stat3 activation and growth of mycosis fungoides tumor cell lines", Proc. Nat. Acad. Sci., USA, vol. 94, No. 13, Jun. 1997, pp. 6764-6769.

Niggli, Verena, "Rho-kinase in human neutrophils: a role in signalling for myosin light chain phosphorylation and cell migration", FEBS Letters, vol. 445, No. 1, 1999, pp. 69-72.

Nitro, Naohisa et al., "Up-Regulation of rho A and rho-Kinase mRHAs in the Rat Myometrium during Pregnancy", Biochemiacl and Biophysical Research Communications, vol. 230, 1997, pp. 356-359.

Nilius, Bernd et al., "Role of Rho and Rho kinase in the activation of volume-regulated anion channels in bovine endothelial cells", Journal of Physiology, vol. 516, No. 1, 1999, pp. 67-74.

Nobes, Catherine D. et al., "Rho GTPases Control Polarity, Protrusion, and Adhesion during Cell Movement", Journal of Cell Biology, vol. 144, No. 6, Mar. 2, 1999, pp. 1235-1244.

Pungpo, Pornpan et al., "Three-dimensional quantitative structure-activity relationship study on HIV-1 reverse transcriptase inhibitors in the class of dipyridodiazepinone derivatives, using comparative molecular field analysis" Journal of Molecular Graphics and Modeling, Elsevier Science Inc., vol. 18, 2000, pp. 581-590.

Rao, P. Vasantha et al., "Modulation of Aqueous Humor Outflow Facility by the Rho Kinase-Specific Inhibitor Y-27632", Investigative Ophthalmology & Visual Science, vol. 42, No. 5, Apr. 2001, pp. 1029-1037.

Rees, Rowland W. et al., "Y-27632, A Rho-Kinase Inhibitor, Inhibits Proliferation and Adrenergic Contraction of Prostatic Smooth Muscle Cells", The Journal of Urology, USA, vol. 170, Dec. 2003, pp. 2517-2522.

Retzer, Michaela et al., "Mildly oxidised low density lipoprotein induces platelet shape change via Rho-kinase-dependent phosphorylation of myosin light chain and moesin", Federation of European Biochemial Societies Letters, vol. 466, 2000, pp. 70-74.

Rizki, Aylin et al., "Polo-like Kinase 1 Is Involved in Invasion through Extracellular Matrix", American Association of Cancer Research, vol. 67, No. 23, Dec. 1, 2007, pp. 11106-11110.

Sah, Valerie P. et al., "Rho Is Required for Galphaq and alpha1-Adrenergic Receptor Signaling in Cardiomyocytes", The Journal of Biological Chemistry, USA, vol. 27, No. 49, Dec. 6, 1996, pp. 31185-31190.

Sahai, Erik et al., "Transformation mediated by RhoA requires activity of ROCK kinases", Current Biology, vol. 9, No. 3, 1999, pp. 136-145.

Sanborn, M.D., William J. et al., "Tofacitinib, an Oral Janus Kinase Inhibitor, in Active Ulcerative Colitis", The New England Journal of Medicine, vol. 367, No. 7, Aug. 16, 2012, pp. 616-624.

Sato, Motohiko et al., "Involvement of Rho-Kinase-Mediated Phosphorylation of Myosin Light Chain in Enhancement of Cerebral Vasospasm", Circulation Research, vol. 87, No. 2, Aug. 4, 2000, pp. 195-200.

Satoh, Shin-Ichi et al., "Antiischemic Properties of Fasudil in Experimental Models of Vasospastic Angina", Jpn. J. Pharmacol., vol. 87, 2001, pp. 34-40.

Satoh, Shinji et al., "Augmented Agonist-induced Ca2+-Sensitization of Coronary Artery Contraction in Genetically Hypertensive Rats: Evidence for Altered Signal Transduction in the Coronary Smooth Muscle Cells", J. Clin. Invest., vol. 94, No. 4, Oct. 1994, pp. 1397-1403.

Sawada, Naoki et al., "Inhibition of Rho-Associated Kinase Results in Suppression of Neointimal Formation of Balloon Injured Arteries", Circulation, vol. 101, May 2, 2000, pp. 2030-2023.

Schmidtke, M. et al., "A rapid assay for evaluation of antiviral activity against coxsackie virus B3, influenza virus A, and herpes simplex virus type 1", Elsevier, Journal of Virological Methods, vol. 95, 2001, pp. 133-143.

(56) References Cited

OTHER PUBLICATIONS

Schneider, Cederic et al., "In Situ Anionic Shielding for Regioselective Metalation: Directed peri and Iterative Metalation Routes to Polyfunctionalized 7-Azaindoles", Angew. Chem. Int. Ed., vol. 51, No. 11, Mar. 12, 2012, pp. 2722-2726.
Schwaller, Juerg et al., "Transformation of hematopoietic cell lines to growth-factor independence and induction of a fatal myelo- and lymphoproliferative disease in mice by retrovirally transduced TEL/JAK2 fusion genes", The EMBO Journal, vol. 17, No. 18, 1998, pp. 5321-5333.
Seasholtz, Tammy M. et al., "Rho and Rho Kinase Mediate Thrombin-Stimulated Vascular Smooth Muscle Cell DNA Synthesis and Migration", Circulation Research, vol. 84, No. 4, 1999, pp. 1186-1193.
Segain, Jean-Pierre et al., "Rho Kinase Blockade Prevents Inflammation Via Nuclear Factor kB Inhibition: Evidence in Crohn's Disease and Experimental Colitis", Gastroenterology, vol. 124, No. 5, May 2003, pp. 1180-1187.
Seidel, H. Martin et al., "Pharmaceutical intervention in the JAK/STAT signaling pathway", Oncogene, vol. 19, No. 21, 2000, pp. 2645-2656.
Sheu, Tiffany G. et al., "Dual Resistance to Adamantanes and Oseltamivir Among Seasonal Influenza A(H1N1) Viruses: 2008-2010", Journal of Infectious Diseases, vol. 203, No. 1, Jan. 1, 2011, pp. 13-17.
Shibata, Rei et al., Role of Rho-Associated Kinase in Neointima Formation After Vascular Injury, Circulation, vol. 130, Jan. 16, 2001, pp. 284-289.
Shimokawa, Hiroaki et al., "Anti-anginal Effect of Fasudil, a Rho-Kinase Inhibitor, in Patients With Stable Effort Angina: A Multicenter Study", Journal of Cardiovascular Pharmacology, vol. 40, No. 5, 2002, pp. 751-761.
Shimokawa, Hiroaki et al., "Cellular and Molecular Mechanisms of Coronary Artery Spasm: Lessons From Animal Models", Jpn. Cir. J., vol. 64, No. 1, 2000, pp. 1-12.
Shimokawa, Hiroaki et al., "Long-term inhibition of Rho-kinase induces a regression of arteriosclerotic coronary lesions in a percine model in vivo", Cardiovascular Research, Elsevier, vol. 51, 2001, pp. 169-177.
Shimokawa, Hiroaki et al., "Rho-kinase as a Novel Therapeutic Target in Treatment of Cardiovascilar Diseases", Journal of Cardiovascular Pharmacology, vol. 39, No. 3, 2002, pp. 319-327.
Smith, Mark R. et al., "Malignant Transformation of Mammalian Cells Initiated by Constitutive Expression of the Polo-like Kinase1", Biochemical and Biophysical Research Communications, vol. 234, No. 2, 1997, pp. 397-405.
Somlyo, Avril V. et al., Rho-Kinase Inhibitor Retards Migration and in Vivo Dissemination of Human Prostate Cancer Cells, Biochemical and Biophysical Research Communications, vol. 269, No. 3, 2000, pp. 652-659.
Stewart, Gavin W. et al., "Process Development and Large-Scale Synthesis of a c-Met Kinase Inhibitor", Organic Process Research & Development, vol. 14, No. 8, 2010, pp. 849-858.
Strebhardt, Klaus et al., "Targeting polo-like kinase 1 for cancer therapy", Nature Reviews, Cancer, Nature Publishing Group, London, GB, vol. 6, No. 4, Apr. 1, 2006, pp. 321-330.
Stump, Kristine L. et al., "A highly selective, orally active inhibitor of Janus kinase 2, CEP-33779, ablates disease in two mouse models of rheumatoid arthritis", Arthritis Research & Therapy, BioMed Central, London, GB, vol. 13, No. 2, Apr. 21, 2011, p. 1, abstract.
Subbarao, E. Kanta et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influenza A Virus Vaccine", Journal of Virology, The American Society for Microbiology, vol. 69, No. 10, Oct. 1, 1995, pp. 5969-5977.
Sudbeck, Elise A. et al., "Structure-based Design of Specific Inhibitors of Janus Kinase 3 as Apoptosis-inducing Antileukemic Agents", Clinical Cancer Research, vol., 5, No. 6, Jun. 1999, pp. 1569-1582.
Suzuki, Kotaro et al., "Role of common cytokine receptor gamma chain (gamma(c))- and Jak3-dependent signaling in the proliferation and survival of murine mast cells", Blood, 2000, 96(6), pp. 2172-2180.
Tachibana, E. et al., "Intra-arterial infusion of fasudil hydrochloride for treating vasospasm following subarachnoid haemorrhage", Acta Neurochir (Wien), 1999, 141(1), pp. 13-19.
Tahara, Masahiro et al., "RhoA/Rho-Kinase Cascade Is Involved in Oxytocin-Induced Rat Uterine Contraction", Endocrinology, vol. 143, No. 3, Mar. 2002, pp. 920-929.
Tobita, K. et al., "Plaque Assay and Primary Isolation of Influenza A Viruses in an Established Line of Canine Kidney Cells (MDCK) in the Presence of Trypsin", Med. Microbiol. Immunol., vol. 162, 1975, pp. 9-14.
Traxler, Peter M., "Protein tyrosine kinase inhibitors in cancer treatment", Expert Opinion on Therapeutic Patents, vol. 7, No. 6, 1997, pp. 571-588.
Trieu, Vuong N. et al., "A Specific Inhibitor of Janus Kinase-3 Increases Survival in a Transgenic Mouse Model of Amyotrophic Lateral Sclerosis", Biochemical and Biophysical Research Communications, vol. 267, No. 1, 2000, pp. 22-25.
Uehata, Masayoshi et al., "Calcium sensitization of smooth muscle mediated by a Rho-associated protein kinase in hypertension", Nature, vol. 389, Oct. 30, 1997, pp. 990-994.
Utsunomiya, T. et al., "Antianginal effects of hydroxyfasudil, a Rho-kinase inhibitor, in a canine model of effort angina", British Journal of Pharmacology, vol. 134, No. 8, 2001, pp. 1724-1730.
Van Baelen, Gitte et al., "Synthesis of 5-methyl-5H-pyrrolo[2,3-c]quinoline and 4-methyl-4H-pyrrolo[2,3-c] isoquinoline: two new unnatural D-ring stripped isomers of the cryptolepine series", Arkivoc, Jan. 1, 2009, pp. 174-182.
Venkatesh, Srini et al., "Role of the Development Scientist in Compound Lead Selection and Optimization", Journal of Pharmaceutical Sciences, vol. 89, No. 2, Feb. 2000, pp. 145-154.
Vertex Pharmaceuticals Incorporated, "VX-787 Showed Significant Antiviral Activity and Reduced the Severity and Duration of Influenza Symptoms in Phase 2 Challenge Study", Mar. 4, 2013.
Vippagunta, Shuda R. et al., "Crystalline Solids", Advanced Drug Delivery Reviews, vol. 48, 2001, pp. 3-26.
Wada, Makoto et al "siRNA targeting PLK-1 induces apoptosis of synoviocytes in rheumatoid arthritis", Biochemical and Biophysical Research Communications, vol. 357, No. 2, 2007, pp. 353-359.
Watanabe, GO et al., "Protein Kinase N (PKN) and PKN-Related Protein Rhophilin as Targets of Small GTPase Rho", Science, vol. 271, Feb. 2, 1996, pp. 645-648.
Weichert, Wilko et al., "Polo-like kinase isoform expression is a prognostic factor in ovarian carcinoma", British Journal of Cancer, vol. 90, No. 4, 2004, pp. 815-821.
Weichert, Wilko et al., "Polo-like kinase isoforms in breast cancer: expression patterns and prognostic implications", Virchows Archiv, vol. 446, No, 4, 2005, pp. 442-450.
West, Anthony R., "Solid state chemistry and its implications", John Wiley & Sons, 1984, pp. 358 & 365.
Written Opinion of the International Searching Authority issued for PCT Application No. PCT/US2005/010846 Dated Aug. 19, 2005.
Written Opinion of the International Searching Authority issued for PCT Application No. PCT/US2007/001225 Dated Jul. 20, 2007.
Written Opinion of the International Searching Authority issued for PCT Application No. PCT/US2007/025688 Dated Apr. 6, 2008.
Written Opinion of the International Searching Authority issued for PCT Application No. PCT/US2007/026190 Dated May 20, 2008.
Written Opinion of the International Searching Authority issued for PCT Application No. PCT/US2008/009786 Dated Jan. 19, 2009.
Written Opinion of the International Searching Authority issued for PCT Application No. PCT/US2009/001534 Dated Apr. 2, 2010.
Written Opinion of the International Searching Authority issued for PCT Application No. PCT/US2009/003716 Dated Nov. 20, 2009.
Written Opinion of the International Searching Authority issued for PCT Application No. PCT/US2009/003723 Dated Nov. 20, 2009.
Xu, Zhengren et al., "Palladium-Catalyzed Indole and Azaindole Synthesis by Direct Annulation of Electron-Poor o-Chloroanilines and o-Chloroaminopyridines with Aldehydes", Synthesis, vol. 2008, No. 24, Dec. 1, 2008, pp. 3981-3987.

(56) References Cited

OTHER PUBLICATIONS

Yanazume, Tetsuhiko et al., "Rho/ROCK Pathway Contributes to the Activation of Extracellular Signal-regulated Kinase/GTA-4 during Myocardial Cell Hypertrophy*", The Journal of Biological Chemistry, USA, vol. 277, No. 10, Mar. 8, 2002, pp. 8618-8625.

Yoshii, Akihiro et al. "Relaxation of Contracted Rabbit Tracheal and Human Bronchial Smooth Muscle by Y-27632 through Inhibition of Ca2+ Sensitization", American Journal of Respiratory Cell and Molecular Biology, vol. 20, No. 6, 1999, pp. 1190-1200.

Yu, Chao-Lan et al., "Constitutive Activation of the Janus Kinase-STAT Pathway in T Lymphoma Overexpressing the Lck protein tyrosine kinase1", Journal of Immunology, vol. 159, No. 11, 1997, pp. 5206-5210.

Zhou, Yan et al., "Nonsteroidal Anti-Inflammatory Drugs Can Lower Amyloidogenic Aβ42 by Inhibiting Rho", Science, vol. 302, No. 14, Nov. 2003, pp. 1215-1218.

In Vivo exposures of Hydrates 3 of Compound (1), compared to exposures of the corresponding HCL salt, H₂SO₄ salt, and SDD in Monkeys and Rats Hydrate 3 of Compound (1) shows dose-proportional increase in rats up to 500 mg/kg, but plateaus at 250 mg/kg in monkeys. Dosed as suspensions in 0.5% MC

INHIBITORS OF INFLUENZA VIRUSES REPLICATION

CROSS REFERENCE TO RELATED APPLICATION

This patent application is a continuation of PCT application no. PCT/US2016/031713, filed on May 11, 2016, which claims the benefit of U.S. provisional application No. 62/160,637, filed on May 13, 2015. Each of these documents is hereby incorporated by reference in its entirety.

FIELD OF THE INVENTION

The present invention relates to compounds and solid forms of compounds that are useful for inhibiting influenza virus replication, treating or reducing the severity of influenza infections in patients, and prophylactically preventing or reducing the incidence of influenza infections in patients.

BACKGROUND

Influenza spreads around the world in seasonal epidemics, resulting in the deaths of hundreds of thousands annually—millions in pandemic years. For example, three influenza pandemics occurred in the 20th century and killed tens of millions of people, with each of these pandemics being caused by the appearance of a new strain of the virus in humans. Often, these new strains result from the spread of an existing influenza virus to humans from other animal species.

Influenza is primarily transmitted from person to person via large virus-laden droplets that are generated when infected persons cough or sneeze; these large droplets can then settle on the mucosal surfaces of the upper respiratory tracts of susceptible individuals who are near (e.g. within about 6 feet) infected persons. Transmission might also occur through direct contact or indirect contact with respiratory secretions, such as touching surfaces contaminated with influenza virus and then touching the eyes, nose or mouth. Adults might be able to spread influenza to others from 1 day before getting symptoms to approximately 5 days after symptoms start. Young children and persons with weakened immune systems might be infectious for 10 or more days after onset of symptoms.

Influenza viruses are RNA viruses of the family Orthomyxoviridae, which comprises five genera: Influenza virus A, Influenza virus B, Influenza virus C, ISA virus and Thogoto virus.

The Influenza virus A genus has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are: H1N1 (which caused Spanish influenza in 1918), H2N2 (which caused Asian Influenza in 1957), H3N2 (which caused Hong Kong Flu in 1968), H5N1 (a pandemic threat in the 2007-08 influenza season), H7N7 (which has unusual zoonotic potential), H1N2 (endemic in humans and pigs), H9N2, H7N2, H7N3 and H10N7.

The Influenza virus B genus has one species, influenza B virus. Influenza B almost exclusively infects humans and is less common than influenza A. The only other animal known to be susceptible to influenza B infection is the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

The Influenza virus C genus has one species, influenza C virus, which infects humans and pigs and can cause severe illness and local epidemics. However, influenza C is less common than the other types and usually seems to cause mild disease in children.

Influenza A, B and C viruses are very similar in structure. The virus particle is 80-120 nanometers in diameter and usually roughly spherical, although filamentous forms can occur. Unusually for a virus, its genome is not a single piece of nucleic acid; instead, it contains seven or eight pieces of segmented negative-sense RNA. The Influenza A genome encodes 11 proteins: hemagglutinin (HA), neuraminidase (NA), nucleoprotein (NP), M1, M2, NS1, NS2(NEP), PA, PB1, PB1-F2 and PB2.

HA and NA are large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins have been targets for antiviral drugs. Furthermore, they are antigens to which antibodies can be raised. Influenza A viruses are classified into subtypes based on antibody responses to HA and NA, forming the basis of the H and N distinctions (vide supra) in, for example, H5N1.

Influenza produces direct costs due to lost productivity and associated medical treatment, as well as indirect costs of preventative measures. In the United States, influenza is responsible for a total cost of over $10 billion per year, while it has been estimated that a future pandemic could cause hundreds of billions of dollars in direct and indirect costs. Preventative costs are also high. Governments worldwide have spent billions of U.S. dollars preparing and planning for a potential H5N1 avian influenza pandemic, with costs associated with purchasing drugs and vaccines as well as developing disaster drills and strategies for improved border controls.

Current treatment options for influenza include vaccination, and chemotherapy or chemoprophylaxis with anti-viral medications. Vaccination against influenza with an influenza vaccine is often recommended for high-risk groups, such as children and the elderly, or in people that have asthma, diabetes, or heart disease. However, it is possible to get vaccinated and still get influenza. The vaccine is reformulated each season for a few specific influenza strains but cannot possibly include all the strains actively infecting people in the world for that season. It may take six months for the manufacturers to formulate and produce the millions of doses required to deal with the seasonal epidemics; occasionally, a new or overlooked strain becomes prominent during that time and infects people although they have been vaccinated (as by the H3N2 Fujian flu in the 2003-2004 influenza season). It is also possible to get infected just before vaccination and get sick with the very strain that the vaccine is supposed to prevent, as the vaccine may require several weeks to become effective.

Further, the effectiveness of these influenza vaccines is variable. Due to the high mutation rate of the virus, a particular influenza vaccine usually confers protection for no more than a few years. A vaccine formulated for one year may be ineffective in the following year, since the influenza virus changes rapidly over time, and different strains become dominant.

Also, because of the absence of RNA proofreading enzymes, the RNA-dependent RNA polymerase of influenza vRNA makes a single nucleotide insertion error roughly every 10 thousand nucleotides, which is the approximate length of the influenza vRNA. Hence, nearly every newly-manufactured influenza virus is a mutant-antigenic drift. The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

Antiviral drugs can also be used to treat influenza, with neuraminidase inhibitors being particularly effective, but viruses can develop resistance to the standard antiviral drugs. Such agents can be prepared so as to have a variety of different chemical forms including chemical derivatives or salts, or to have different physical forms. For example, they may be amorphous, may have different crystalline polymorphs, or may exist in different solvation or hydration states. By varying the forms, it may be possible to vary the physical properties thereof. Such different forms may have different properties, in particular, as oral formulations. Specifically, it may be desirable to identify improved forms that exhibit improved properties, such as increased aqueous solubility and stability, better processability or preparation of pharmaceutical formulations, and increase of the bio-availability of orally-administered compositions. Such improved properties discussed above may be altered in a way which is beneficial for a specific therapeutic effect.

Variation of the forms of an antiviral agent can be one of many ways in which to modulate the physical properties of such antiviral agent to be more useful in treating influenza.

SUMMARY OF THE INVENTION

The present invention generally relates to polymorphic forms of Compound (1), solvates thereof, pharmaceutically acceptable salts thereof, pharmaceutically acceptable formulations thereof, methods of preparing such polymorphic forms of Compound (1), and uses of such polymorphic forms or solvates for inhibiting the replication of influenza viruses, for reducing the amount of influenza viruses, and for treating influenza.

In one aspect, the present invention provides a polymorphic form of Compound (1) wherein Compound (1) is represented by the following structural formula:

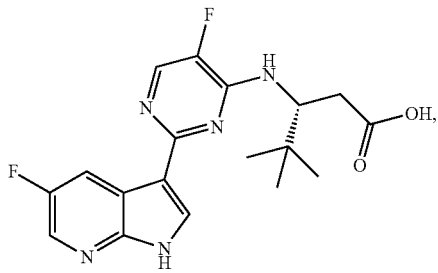 [SMILES: CC(C)(C)[C@@H](CC(=O)O)Nc1nc(-c2c[nH]c3ncc(F)cc23)ncc1F]

and wherein the polymorphic form is selected from the group consisting of: Hydrate 2 of Compound (1), Hydrate 3 of Compound (1), Form A of Compound (1), Form B of Compound (1), Form C of Compound (1), Form D of Compound (1), and amorphous Compound (1).

In some embodiments, the polymorphic form is Hydrate 2 of Compound (1). In some embodiments, Hydrate 2 of Compound (1) is characterized by one or more peaks corresponding to 2-theta values, measured in degrees, of 6.9±0.2, 7.9±0.2, 13.8±0.2, 15.9±0.2, 20.9±0.2, and 23.4±0.2 in an X-ray powder diffraction pattern. In other embodiments, Hydrate 2 of Compound (1) is further characterized by one or more peaks corresponding to 2-theta values, measured in degrees, of 17.1±0.2, 18.6±0.2, 22.1±0.2 and 29.2±0.2 in an X-ray powder diffraction pattern.

In some embodiments, Hydrate 2 of Compound (1) is further characterized by a $^{13}C$ SSNMR spectrum of 178.5 ppm, 137.2 ppm, 126.8 ppm, 107.0 ppm, and 35.3 ppm. And, in other embodiments, Hydrate 2 of Compound (1) is further characterized by a $^{13}C$ SSNMR spectrum of 27.1 ppm.

In some embodiments, the polymorphic form is Hydrate 3 of Compound (1). In some embodiments, Hydrate 3 of Compound (1) is characterized by one or more peaks corresponding to 2-theta values, measured in degrees, of 7.0±0.2, 18.6±0.2, 20.8±0.2, 23.3±0.2, and 26.0±0.2 in an X-ray powder diffraction pattern. In other embodiments, Hydrate 3 of Compound (1) is further characterized by one or more peaks corresponding to 2-theta values, measured in degrees, of 8.9±0.2, 16.6±0.2, and 28.9±0.2 in an X-ray powder diffraction pattern.

In some embodiments, Hydrate 3 of Compound (1) is further characterized by a $^{13}C$ SSNMR spectrum of 178.8 ppm, 136.7 ppm, 107.8 ppm, 34.9 ppm, and 26.3 ppm. In other embodiments, Hydrate 3 of Compound (1) is further characterized by a $^{13}C$ SSNMR spectrum of 127.7 ppm.

In some embodiments, the polymorphic form is Form D of Compound (1). In some embodiments, Form D of Compound (1) is characterized by one or more peaks corresponding to 2-theta values, measured in degrees, of 6.1±0.2, 14.7±0.2, 23.9±0.2, and 25.2±0.2 in an X-ray powder diffraction pattern. In some embodiments, Form D of Compound (1) is further characterized by one or more peaks corresponding to 2-theta values, measured in degrees, of 7.3±0.2, 13.2±0.2, and 19.4±0.2 in an X-ray powder diffraction pattern.

In some embodiments, the polymorphic form is Form A of Compound (1). In some embodiments, Form A of Compound (1) is characterized by one or more peaks corresponding to 2-theta values, measured in degrees, of 7.2±0.2, 7.9±0.2, 17.1±0.2, and 24.4±0.2 in an X-ray powder diffraction pattern. In some embodiments, Form A of Compound (1) is further characterized by one or more peaks corresponding to 2-theta values, measured in degrees, of 14.4±0.2, 19.4±0.2, and 21.1±0.2 in an X-ray powder diffraction pattern.

In some embodiments, the polymorphic form is Form B of Compound (1). In some embodiments, Form B of Compound (1) is characterized by one or more peaks corresponding to 2-theta values, measured in degrees, of 6.3±0.2, 12.6±0.2, 17.8±0.2, and 18.4±0.2 in an X-ray powder diffraction pattern. In some embodiments, Form B of Compound (1) is further characterized by one or more peaks corresponding to 2-theta values, measured in degrees, of 15.4±0.2, 16.0±0.2, and 18.9±0.2 in an X-ray powder diffraction pattern.

In some embodiments, the polymorphic form is Form C of Compound (1). In some embodiments, Form C of Compound (1) is characterized by one or more peaks corresponding to 2-theta values, measured in degrees, of 8.8±0.2, 12.2±0.2, 14.4±0.2, and 24.2±0.2 in an X-ray powder diffraction pattern. In some embodiments, Form B of Compound (1) is further characterized by one or more peaks corresponding to 2-theta values, measured in degrees, of 6.1±0.2, 17.7±0.2, and 19.1±0.2 in an X-ray powder diffraction pattern.

In some embodiments, the polymorphic form is amorphous Compound (1).

Another aspect of the present invention provides a solvate of Compound (1) wherein Compound (1) is represented by the following structural formula:

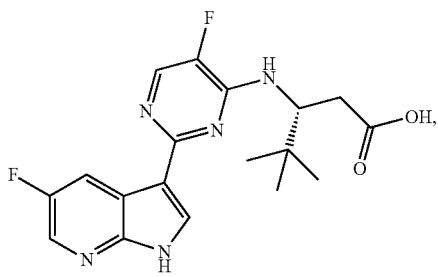

and wherein the solvate is selected from the group consisting of: an isopropyl alcohol solvate of Compound (1), an acetonitrile solvate of Compound (1), or a 2-methyl tetrahydrofuran solvate of Compound (1).

In some embodiments, the solvate is the isopropyl alcohol solvate of Compound (1).

In some embodiments, the isopropyl alcohol solvate of Compound (1) is characterized by one or more peaks corresponding to 2-theta values, measured in degrees, of 5.7±0.2, 6.3±0.2, 13.1±0.2, and 17.4±0.2 in an X-ray powder diffraction pattern. In some embodiments, the isopropyl alcohol solvate of Compound (1) is further characterized by one or more peaks corresponding to 2-theta values, measured in degrees, of 8.0±0.2, 19.3±0.2, and 24.3±0.2 in an X-ray powder diffraction pattern.

In some embodiments, the solvate is the acetonitrile solvate of Compound (1).

In some embodiments, the acetonitrile solvate of Compound (1) is characterized by one or more peaks corresponding to 2-theta values, measured in degrees, of 6.2±0.2, 6.8±0.2, 8.5±0.2, 12.2±0.2, and 21.8±0.2 in an X-ray powder diffraction pattern. In some embodiments, the acetonitrile solvate of Compound (1) is further characterized by one or more peaks corresponding to 2-theta values, measured in degrees, of 9.1±0.2, 13.5±0.2, and 15.2±0.2 in an X-ray powder diffraction pattern.

In some embodiments, the solvate is the 2-methyl tetrahydrofuran solvate of Compound (1).

In some embodiments, the 2-methyl tetrahydrofuran solvate of Compound (1) is characterized by one or more peaks corresponding to 2-theta values, measured in degrees, of 6.5±0.2, 8.4±0.2, 15.3±0.2, and 19.2±0.2 in an X-ray powder diffraction pattern. In some embodiments, the 2-methyl tetrahydrofuran solvate of Compound (1) is further characterized by one or more peaks corresponding to 2-theta values, measured in degrees, of 14.7±0.2, 16.4±0.2, and 24.5±0.2 in an X-ray powder diffraction pattern.

Another aspect of the present invention provides a pharmaceutical composition comprising a polymorphic form of Compound (1), such as any of the forms described herein, and at least one pharmaceutically acceptable carrier or excipient.

In some embodiments, the polymorphic form is Hydrate 2 of Compound (1). In some embodiments, the polymorphic form is Hydrate 3 of Compound (1). In some embodiments, the polymorphic form is Form D of Compound (1). In some embodiments, the polymorphic form is Form A of Compound (1). In some embodiments, the polymorphic form is Form B of Compound (1). In some embodiments, the polymorphic form is Form C of Compound (1). In some embodiments, the polymorphic form is amorphous Compound (1).

Another aspect of the present invention provides a method of reducing the amount of influenza viruses in a biological in vitro sample or in a subject, comprising administering to the sample an effective amount of a polymorphic form of Compound (1), such as any of the forms described herein.

Another aspect of the present invention provides a method of inhibiting the replication of influenza viruses in a biological in vitro sample or in a subject, comprising administering to the sample an effective amount of a polymorphic form of Compound (1), such as any of the forms described herein.

Another aspect of the present invention provides a method of treating influenza in a subject, comprising administering to the subject a therapeutically effective amount of a polymorphic form of Compound (1), such as any of the forms described herein.

Several implementations of these methods further comprise co-administering one or more additional therapeutic agents to the subject. In some implementations, additional therapeutic agent is an anti-virus drug. For example, the anti-virus drug is a neuraminidase inhibitor. In other examples, the neuraminidase inhibitor is oseltamivir or zanamivir. And, in some examples, the anti-virus drug is a polymerase inhibitor. For instance, the polymerase inhibitor is flavipiravir.

In several implementations of these methods, the influenza viruses are influenza A viruses.

Another aspect of the present invention provides a method of generating a polymorphic form of Compound (1). In some implementations, the polymorphic form is Hydrate 2 of Compound (1). In some implementations, the polymorphic form is Hydrate 3 of Compound (1). In some implementations, the polymorphic form is Form D of Compound (1). In some implementations, the polymorphic form is Form A of Compound (1). In some implementations, the polymorphic form is Form B of Compound (1). In some implementations, the polymorphic form is Form C of Compound (1). And, in some implementations, the polymorphic form is amorphous Compound (1).

Another aspect of the present invention provides methods of generating Hydrate 2, Hydrate 3, Form D, Form A, Form B, Form C, or amorphous Compound (1).

Another aspect of the present invention provides a dosage regimen comprising administering to a subject a polymorphic form of Compound (1) or a pharmaceutically acceptable salt thereof in a dosage amount of 100 mg to 1,600 mg, wherein the dosage amount is administered once, twice or three times per day.

In some implementations, the dosage amount is 300 mg to 1,600 mg. For example, the dosage amount is 600 mg to 1,200 mg.

In some implementations, the dosage is administered once per day. In some of these implementations, the dosage amount is 600 mg or 800 mg. In others implementations, the dosage amount is 300 mg to 900 mg.

In some implementations, the dosage is administered twice per day. In some of these implementations, the dosage amount is 400 mg or 600 mg.

In some implementations of the methods above, the polymorphic form of Compound (1) or a pharmaceutically acceptable salt thereof is administered for duration of treatment of 1 day to an entire flu season. In some implementations, the treatment duration is 3 days to 14 days. In other implementations, the treatment duration is 3 days, 4 days, or 5 days.

In some implementations of the methods above, a loading dosage amount of 600 mg to 1,600 mg is administered to the subject on day 1 and a dosage amount of 400 mg to 1,200 mg is administered to the subject for the rest of the treatment duration. In other implementations, a loading dosage amount of 900 mg or 1,200 mg is administered to the subject on day 1 and a dosage amount of 600 mg to 800 mg is administered to the subject for the rest of the treatment duration. In some implementations, a loading dosage amount of 900 mg is administered to the subject on day 1 and a dosage amount of 600 mg is administered once a day to the subject for the rest of the treatment duration. In some implementations, a loading dosage amount of 1,200 mg is administered to the subject on day 1 and a dosage amount of 600 mg is administered once a day to the subject for the rest of the treatment duration.

BRIEF DESCRIPTION OF DRAWINGS

The following figures are provided by way of example and are not intended to limit the scope of the claimed invention.

DETAILED DESCRIPTION OF THE INVENTION

The present invention provides polymorphic forms of Compound (1), solvates thereof, uses therefor, and methods of synthesizing these polymorphic forms and solvates.

I. SOLID FORMS

Compound (1) represented by the following structural formula:

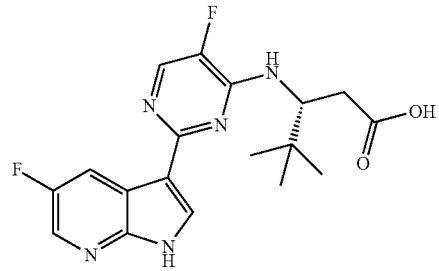 [SMILES: CC(C)(C)[C@@H](CC(=O)O)Nc1nc(-c2c[nH]c3ncc(F)cc23)ncc1F]

and pharmaceutically acceptable salts thereof can inhibit the replication of influenza viruses and also described in WO 2010/148197.

Compound (1) can exist in or form different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds. Generally, different polymorphs can be characterized by analytical methods such as X-ray powder diffraction (XRPD) pattern, thermogravimetric analysis (TGA), and differential scanning calorimetry (DSC), or by its melting point, or other techniques known in the art. As used herein, the term "polymorphic form" includes solvates, neat polymorphic forms that do not have any solvates, and an amorphous form.

One aspect of the present invention provides a polymorphic form of Compound (1) wherein Compound (1) is represented by the following structural formula:

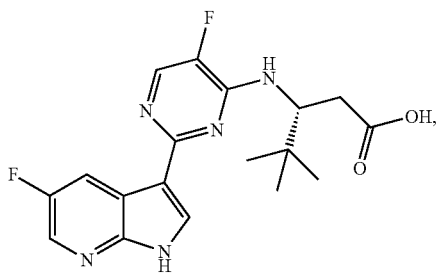 [SMILES: CC(C)(C)[C@@H](CC(=O)O)Nc1nc(-c2c[nH]c3ncc(F)cc23)ncc1F]

and wherein the polymorphic form is selected from the group consisting of: Hydrate 2 of Compound (1), Hydrate 3 of Compound (1), Form A of Compound (1), Form B of Compound (1), and Form D of Compound (1).

A. Hydrate 2 of Compound (1).

One embodiment of the present invention provides a Hydrate 2 of Compound (1).

In some embodiments, Hydrate 2 of Compound (1) is characterized by one or more peaks corresponding to 2-theta values, measured in degrees, of 6.9±0.2, 7.9±0.2, 13.8±0.2, 15.9±0.2, 20.9±0.2, and 23.4±0.2 in an X-ray powder diffraction pattern. In some embodiments, Hydrate 2 of Compound (1) is further characterized by one or more peaks corresponding to 2-theta values, measured in degrees, of 17.1±0.2, 18.6±0.2, 22.1±0.2 and 29.2±0.2 in an X-ray powder diffraction pattern.

Figure 1:
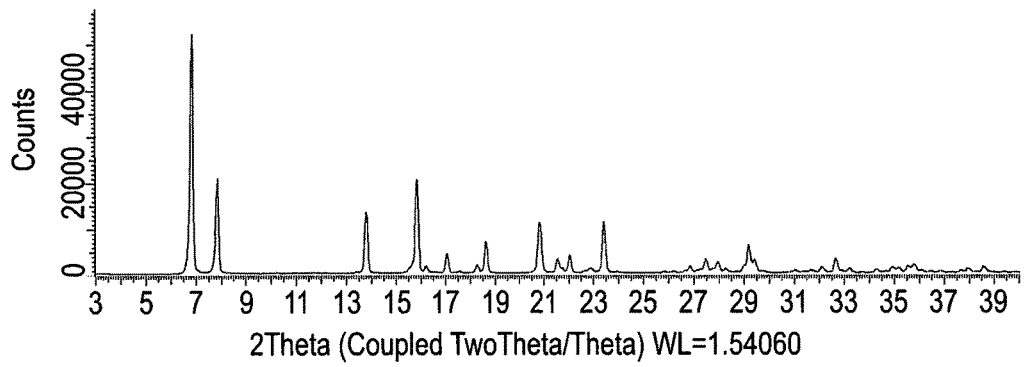
FIG. 1 is an X-ray powder diffraction pattern (XRPD) for Hydrate 2 of Compound (1).

Referring to FIG. 1, in one embodiment, Hydrate 2 of Compound (1) is characterized by an XRPD Pattern, obtained using the methods described in Example 1, having the following peaks:

TABLE 1A

XRPD pattern for Hydrate 2 of Compound (1).

| Angle (2-Theta) ± 0.2 | Relative Intensity % |
| --- | --- |
| 6.9 | >10 |
| 7.9 | >10 |
| 13.8 | >10 |

TABLE 1A-continued

XRPD pattern for Hydrate 2 of Compound (1).

| Angle (2-Theta) ± 0.2 | Relative Intensity % |
| --- | --- |
| 15.9 | >10 |
| 18.6 | >10 |
| 20.9 | >10 |
| 23.4 | >10 |
| 29.2 | >10 |

Referring to FIG. 1, in one embodiment, Hydrate 2 of Compound (1) is further characterized by an XRPD Pattern, obtained using the methods described in Example 1, having the following peaks:

TABLE 1B

XRPD pattern for Hydrate 2 of Compound (1).

| Angle (2-Theta) ± 0.2 | Relative Intensity % |
| --- | --- |
| 6.9 | >10 |
| 7.9 | >10 |
| 13.8 | >10 |
| 15.9 | >10 |
| 17.1 | <10 |
| 18.6 | >10 |
| 20.9 | >10 |
| 22.1 | <10 |
| 23.4 | >10 |
| 27.5 | <10 |
| 29.2 | >10 |
| 29.4 | <10 |

In other embodiments, Hydrate 2 of Compound (1) is characterized by a $^{13}$C SSNMR spectrum of 178.5 ppm, 137.2 ppm, 126.8 ppm, 107.0 ppm, and 35.3 ppm. In some embodiments, Hydrate 2 of Compound (1) is further characterized by a $^{13}$C SSNMR spectrum of 27.1 ppm.

Figure 2:
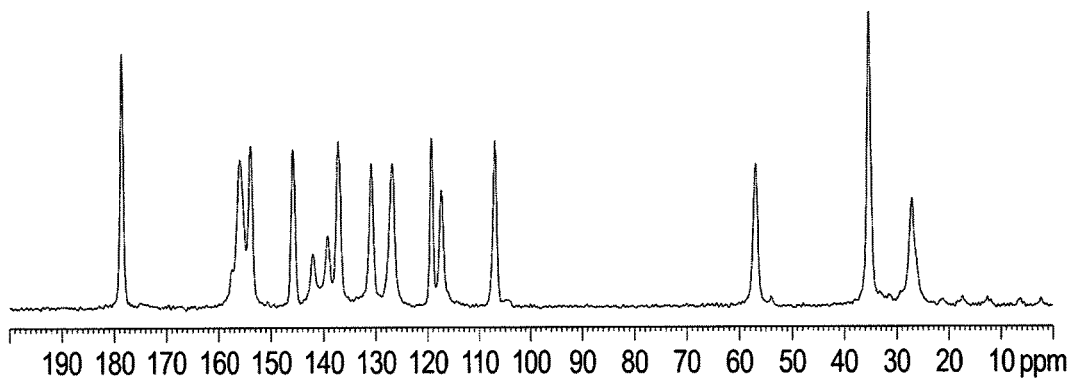
FIG. 2 is a $C^{13}$ SSNMR spectrum of Hydrate 2 of Compound (1).

Referring to FIG. 2, in one embodiment, Hydrate 2 of Compound (1) is characterized by a $^{13}$C SSNMR spectrum, obtained using the methods described in Example 1, having the following peaks:

TABLE 2

$^{13}$C SSNMR spectrum for Hydrate 2 of Compound (1).

| Chemical Shift (ppm) | Relative Intensity % |
| --- | --- |
| 178.5 | >30 |
| 155.9 | >30 |
| 153.9 | >30 |
| 145.8 | >30 |
| 137.2 | >30 |
| 130.9 | >30 |
| 126.8 | >30 |
| 119.3 | >30 |
| 117.4 | >30 |
| 107.0 | >30 |
| 56.9 | >30 |
| 35.3 | >30 |
| 27.1 | >30 |

B. Hydrate 3 of Compound (1).

One embodiment of the present invention provides a Hydrate 3 of Compound (1).

In some embodiments, Hydrate 3 of Compound (1) is characterized by one or more peaks corresponding to 2-theta values, measured in degrees, of 7.0±0.2, 18.6±0.2, 20.8±0.2, 23.3±0.2, and 26.0±0.2 in an X-ray powder diffraction pattern. In some embodiments, Hydrate 3 of Compound (1) is further characterized by one or more peaks corresponding to 2-theta values, measured in degrees, of 8.9±0.2, 16.6±0.2, and 28.9±0.2 in an X-ray powder diffraction pattern.

Figure 5:
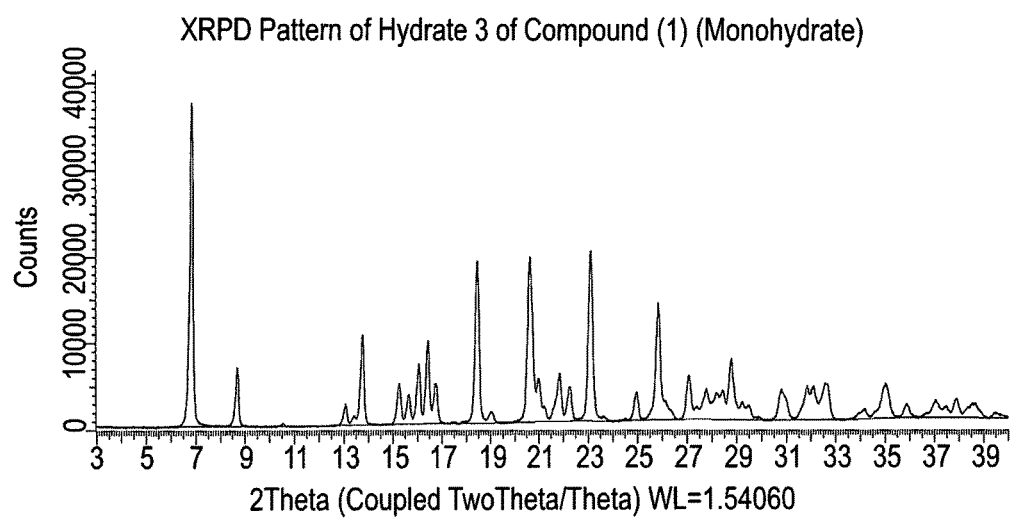
FIG. 5 is an X-ray powder diffraction pattern (XRPD) for Hydrate 3 of Compound (1).

Referring to FIG. 5, in one embodiment, Hydrate 3 of Compound (1) is characterized by an XRPD Pattern, obtained using the methods described in Example 1, having the following peaks:

TABLE 3A

XRPD pattern for Hydrate 3 of Compound (1).

| Angle (2-Theta) ± 0.2 | Relative Intensity % |
|---|---|
| 7.0 | >25 |
| 16.2 | >25 |
| 16.6 | >25 |
| 18.6 | >25 |
| 20.8 | >25 |
| 23.3 | >25 |
| 26.0 | >25 |
| 28.9 | >25 |

Referring to FIG. 5, in one embodiment, Hydrate 3 of Compound (1) is further characterized by an XRPD Pattern, obtained using the methods described in Example 1, having the following peaks:

TABLE 3B

XRPD pattern for Hydrate 3 of Compound (1).

| Angle (2-Theta) ± 0.2 | Relative Intensity % |
|---|---|
| 7.0 | >25 |
| 8.9 | <25 |
| 16.2 | >25 |
| 16.6 | >25 |
| 18.6 | >25 |
| 20.8 | >25 |
| 23.3 | >25 |
| 26.0 | >25 |
| 28.9 | >25 |

In other embodiments, Hydrate 3 of Compound (1) is characterized by a $^{13}$C SSNMR spectrum of 178.8 ppm, 136.7 ppm, 107.8 ppm, 34.9 ppm, and 26.3 ppm. In some embodiments, Hydrate 3 of Compound (1) is further characterized by a $^{13}$C SSNMR spectrum of 127.7 ppm.

Figure 6:
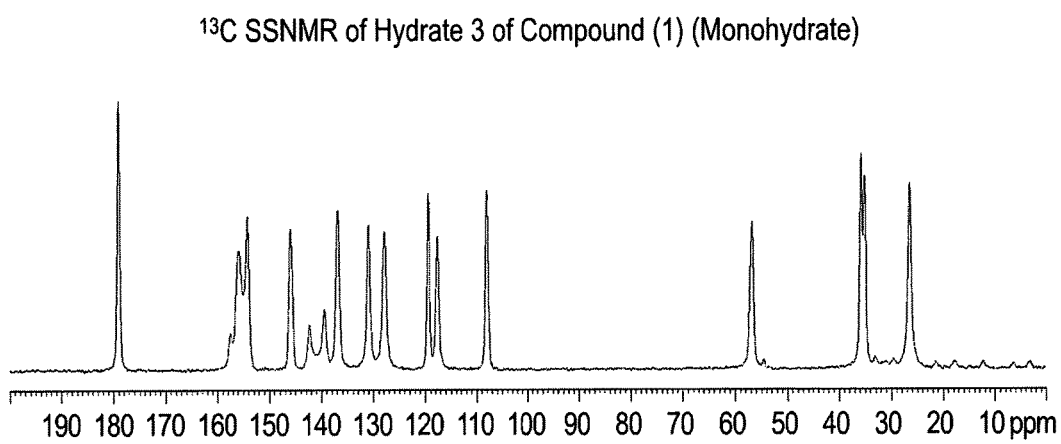
FIG. 6 is a $C^{13}$ SSNMR spectrum of Hydrate 3 of Compound (1).

Referring to FIG. 6, in one embodiment, Hydrate 3 of Compound (1) is characterized by a $^{13}$C SSNMR spectrum, obtained using the methods described in Example 1, having the following peaks:

TABLE 4

$^{13}$C SSNMR spectrum for Hydrate 3 of Compound (1).

| Chemical Shift (ppm) | Relative Intensity % |
|---|---|
| 178.8 | >50 |
| 154.0 | >50 |
| 145.8 | >50 |
| 136.7 | >50 |
| 130.8 | >50 |
| 127.7 | >50 |
| 119.2 | >50 |
| 107.8 | >50 |
| 56.6 | >50 |

TABLE 4-continued $^{13}$C SSNMR spectrum for Hydrate 3 of Compound (1).

| Chemical Shift (ppm) | Relative Intensity % |
|---|---|
| 35.6 | >50 |
| 34.9 | >50 |
| 26.3 | >50 |

C. Form D of Compound (1).

One embodiment of the present invention provides a Form D of Compound (1).

In some embodiments, Form D of Compound (1) is characterized by one or more peaks corresponding to 2-theta values, measured in degrees, of 6.1±0.2, 14.7±0.2, 23.9±0.2, and 25.2±0.2 in an X-ray powder diffraction pattern. In some embodiments, Form D of Compound (1) is further characterized by one or more peaks corresponding to 2-theta values, measured in degrees, of 7.3±0.2, 13.2±0.2, and 19.4±0.2 in an X-ray powder diffraction pattern.

Figure 9:
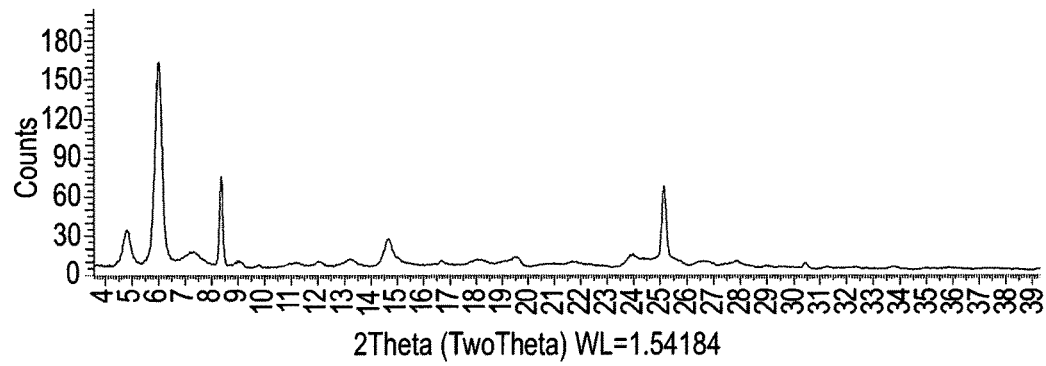
FIG. 9 is an X-ray powder diffraction pattern (XRPD) for Form D of Compound (1).

Referring to FIG. 9, in one embodiment, Form D of Compound (1) is characterized by an XRPD Pattern, obtained using the methods described in Example 1, having the following peaks:

TABLE 5

XRPD pattern for Form D of Compound (1).

| Angle (2-Theta) ± 0.2 | Relative Intensity % |
|---|---|
| 4.8 | >15 |
| 6.1 | >15 |
| 7.3 | <15 |
| 8.4 | >15 |
| 13.2 | <15 |
| 14.7 | <15 |
| 19.4 | <15 |
| 23.9 | <15 |
| 25.2 | >15 |

D. Form A of Compound (1).

One embodiment of the present invention provides a Form A of Compound (1).

In some embodiments, Form A of Compound (1) is characterized by one or more peaks corresponding to 2-theta values, measured in degrees, of 7.2±0.2, 7.9±0.2, 17.1±0.2, and 24.4±0.2 in an X-ray powder diffraction pattern. In some embodiments, Form A of Compound (1) is further characterized by one or more peaks corresponding to 2-theta values, measured in degrees, of 14.4±0.2, 19.4±0.2, and 21.1±0.2 in an X-ray powder diffraction pattern.

Figure 12:
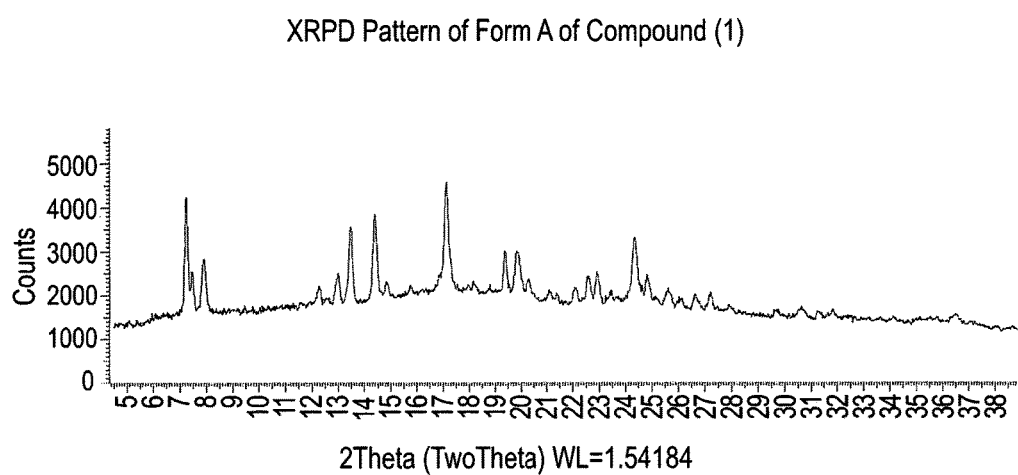
FIG. 12 is an X-ray powder diffraction pattern (XRPD) for Form A of Compound (1).

Referring to FIG. 12, in one embodiment, Form A of Compound (1) is characterized by an XRPD Pattern, obtained using the methods described in Example 1, having the following peaks:

TABLE 6

XRPD pattern for Form A of Compound (1).

| Angle (2-Theta) ± 0.2 | Relative Intensity % |
|---|---|
| 7.2 | >20 |
| 7.9 | >20 |
| 13.0 | >20 |
| 13.5 | >20 |
| 14.4 | >20 |

TABLE 6-continued

XRPD pattern for Form A of Compound (1).

| Angle (2-Theta) ± 0.2 | Relative Intensity % |
|---|---|
| 17.1 | >20 |
| 19.4 | >20 |
| 19.9 | >20 |
| 21.1 | <20 |
| 24.4 | >20 |

E. Form B of Compound (1).

One embodiment of the present invention provides a Form B of Compound (1).

In some embodiments, Form B of Compound (1) is characterized by one or more peaks corresponding to 2-theta values, measured in degrees, of 6.3±0.2, 12.6±0.2, 17.8±0.2, and 18.4±0.2 in an X-ray powder diffraction pattern. In some embodiments, Form B of Compound (1) is further characterized by one or more peaks corresponding to 2-theta values, measured in degrees, of 15.4±0.2, 16.0±0.2, and 18.9±0.2 in an X-ray powder diffraction pattern.

Figure 14:
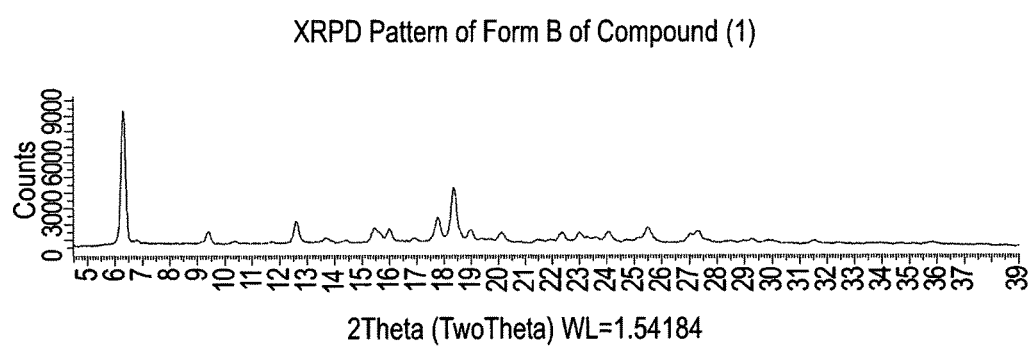
FIG. 14 is an X-ray powder diffraction pattern (XRPD) for Form B of Compound (1).

Referring to FIG. 14, in one embodiment, Form B of Compound (1) is characterized by an XRPD Pattern, obtained using the methods described in Example 1, having the following peaks:

TABLE 7

XRPD pattern for Form B of Compound (1).

| Angle (2-Theta) ± 0.2 | Relative Intensity % |
|---|---|
| 6.3 | >10 |
| 12.6 | >10 |
| 15.4 | >10 |
| 16.0 | >10 |
| 17.8 | >10 |
| 18.4 | >10 |
| 18.9 | >10 |
| 24.1 | >10 |
| 25.5 | >10 |
| 27.4 | >10 |

F. Form C of Compound (1).

One embodiment of the present invention provides a Form C of Compound (1).

In some embodiments, Form C of Compound (1) is characterized by one or more peaks corresponding to 2-theta values, measured in degrees, of 8.8±0.2, 12.2±0.2, 14.4±0.2, and 24.2±0.2 in an X-ray powder diffraction pattern. In some embodiments, Form C of Compound (1) is further characterized by one or more peaks corresponding to 2-theta values, measured in degrees, of 6.1±0.2, 17.7±0.2, and 19.1±0.2 in an X-ray powder diffraction pattern.

Figure 15:
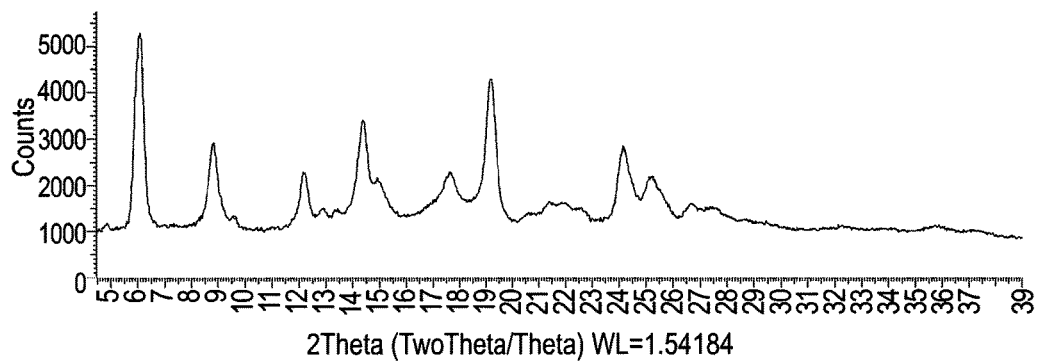
FIG. 15 is an X-ray powder diffraction pattern (XRPD) for Form C of Compound (1).

Referring to FIG. 15, in one embodiment, Form C of Compound (1) is characterized by an XRPD Pattern, obtained using the methods described in Example 1, having the following peaks:

TABLE 8

XRPD pattern for Form C of Compound (1).

| Angle (2-Theta) ± 0.2 | Relative Intensity % |
|---|---|
| 6.1 | >20 |
| 8.8 | >20 |

TABLE 8-continued

XRPD pattern for Form C of Compound (1).

| Angle (2-Theta) ± 0.2 | Relative Intensity % |
|---|---|
| 12.2 | >20 |
| 14.4 | >20 |
| 17.7 | >20 |
| 19.1 | >20 |
| 24.2 | >20 |
| 25.1 | >20 |

G. Isopropyl Alcohol Solvate of Compound (1).

One embodiment of the present invention provides an isopropyl alcohol solvate of Compound (1).

In some embodiments, the isopropyl alcohol solvate of Compound (1) is characterized by one or more peaks corresponding to 2-theta values, measured in degrees, of 5.7±0.2, 6.3±0.2, 13.1±0.2, and 17.4±0.2 in an X-ray powder diffraction pattern. In some embodiments, the isopropyl alcohol solvate of Compound (1) is further characterized by one or more peaks corresponding to 2-theta values, measured in degrees, of 8.0±0.2, 19.3±0.2, and 24.3±0.2 in an X-ray powder diffraction pattern.

Figure 16:
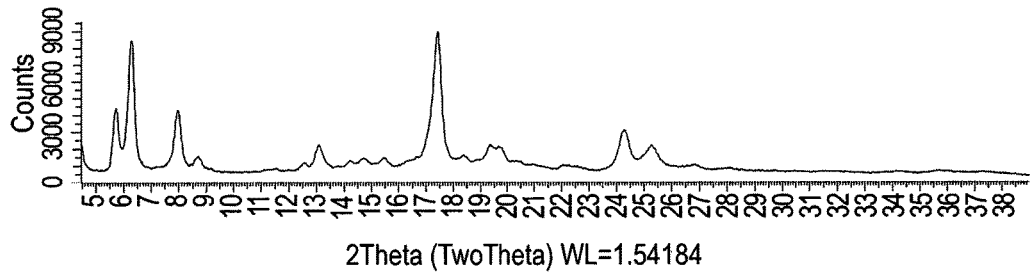
FIG. 16 is an X-ray powder diffraction pattern (XRPD) for an isopropyl alcohol solvate of Compound (1).

Referring to FIG. 16, in one embodiment, the isopropyl alcohol solvate of Compound (1) is characterized by an XRPD Pattern, obtained using the methods described in Example 1, having the following peaks:

TABLE 9

XRPD pattern for isopropyl alcohol solvate of Compound (1).

| Angle (2-Theta) ± 0.2 | Relative Intensity % |
|---|---|
| 5.7 | >15 |
| 6.3 | >15 |
| 8.0 | >15 |
| 13.1 | >15 |
| 17.4 | >15 |
| 19.3 | >15 |
| 19.8 | >15 |
| 24.3 | >15 |
| 25.3 | >15 |

H. Acetonitrile Solvate of Compound (1).

One embodiment of the present invention provides an acetonitrile solvate of Compound (1).

In some embodiments, the acetonitrile solvate of Compound (1) is characterized by one or more peaks corresponding to 2-theta values, measured in degrees, of 6.2±0.2, 6.8±0.2, 8.5±0.2, 12.2±0.2, and 21.8±0.2 in an X-ray powder diffraction pattern. In some embodiments, the acetonitrile solvate of Compound (1) is further characterized by one or more peaks corresponding to 2-theta values, measured in degrees, of 9.1±0.2, 13.5±0.2, and 15.2±0.2 in an X-ray powder diffraction pattern.

Figure 18:
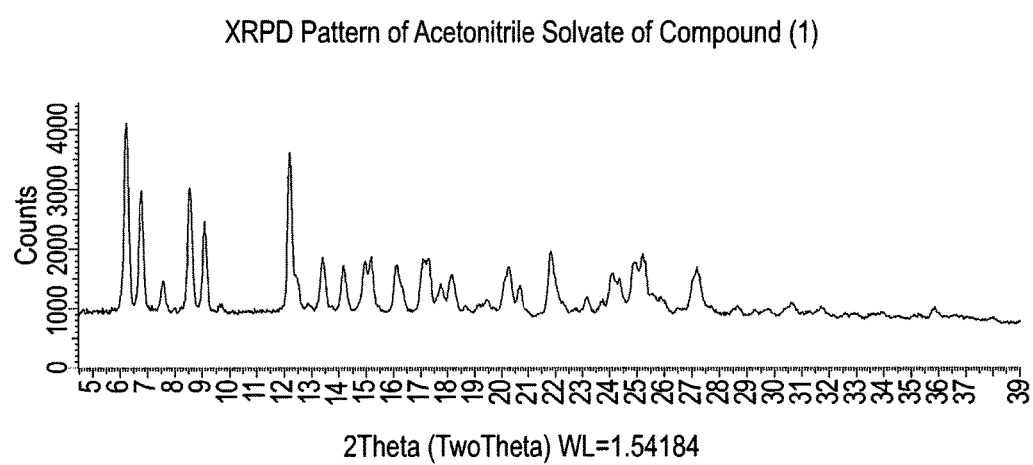
FIG. 18 is an X-ray powder diffraction pattern (XRPD) for an acetonitrile solvate of Compound (1).

Referring to FIG. 18, in one embodiment, the acetonitrile solvate of Compound (1) is characterized by an XRPD Pattern, obtained using the methods described in Example 1, having the following peaks:

TABLE 10

XRPD pattern for acetonitrile solvate of Compound (1).

| Angle (2-Theta) ± 0.2 | Relative Intensity % |
| --- | --- |
| 6.2 | >30 |
| 6.8 | >30 |
| 8.5 | >30 |
| 9.1 | >30 |
| 12.2 | >30 |
| 13.5 | >30 |
| 15.0 | >30 |
| 15.2 | >30 |
| 21.8 | >30 |
| 24.3 | >30 |
| 25.2 | >30 |

I. 2-Methyl Tetrahydrofuran Solvate of Compound (1).

One embodiment of the present invention provides a 2-methyl tetrahydrofuran solvate of Compound (1).

In some embodiments, the 2-methyl tetrahydrofuran solvate of Compound (1) is characterized by one or more peaks corresponding to 2-theta values, measured in degrees, of 6.5±0.2, 8.4±0.2, 15.3±0.2, and 19.2±0.2 in an X-ray powder diffraction pattern. In some embodiments, the 2-methyl tetrahydrofuran of Compound (1) is further characterized by one or more peaks corresponding to 2-theta values, measured in degrees, of 14.7±0.2, 16.4±0.2, and 24.5±0.2 in an X-ray powder diffraction pattern.

Figure 20:
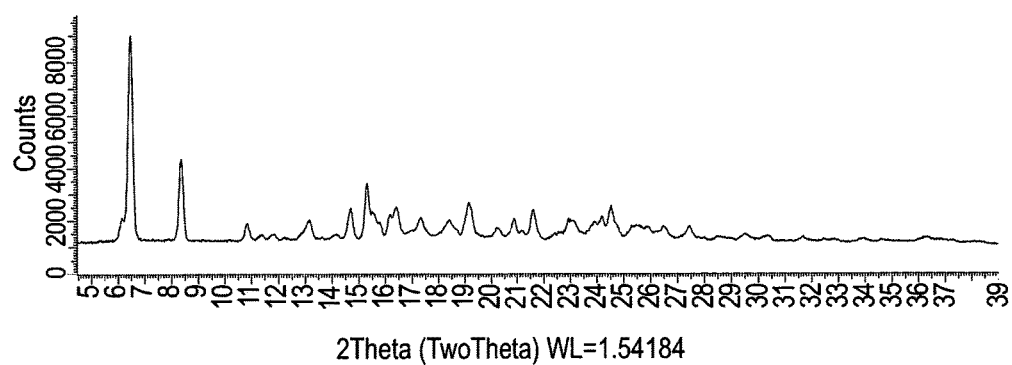
FIG. 20 is an X-ray powder diffraction pattern (XRPD) for a 2-methyl tetrahydrofuran solvate of Compound (1).

Referring to FIG. 20, in one embodiment, the 2-methyl tetrahydrofuran solvate of Compound (1) is characterized by an XRPD Pattern, obtained using the methods described in Example 1, having the following peaks:

TABLE 11

XRPD pattern for 2-methyl tetrahydrofuran solvate of Compound (1).

| Angle (2-Theta) ± 0.2 | Relative Intensity % |
| --- | --- |
| 6.5 | >15 |
| 8.4 | >15 |
| 14.7 | >15 |
| 15.3 | >15 |
| 16.4 | >15 |
| 19.2 | >15 |
| 21.6 | >15 |
| 24.5 | >15 |

J. Amorphous Compound (1).

One embodiment of the present invention provides amorphous Compound (1).

Figure 21:
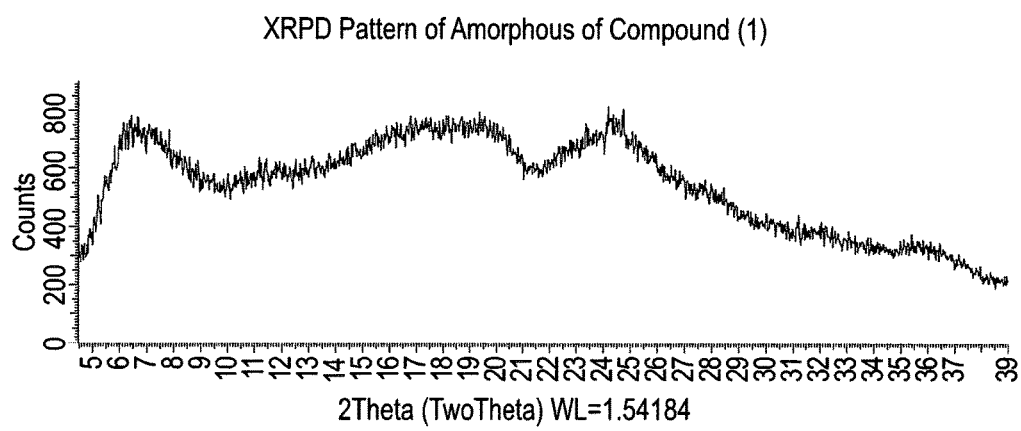
FIG. 21 is an X-ray powder diffraction pattern (XRPD) for amorphous Compound (1).

Referring to FIG. 21, the XRPD pattern of amorphous Compound (1) lacks any characteristic peaks.

II. METHODS OF GENERATING SOLID FORMS OF COMPOUND (1)

In another embodiment, the present invention is directed to methods of preparing Hydrate 2 of Compound (1), Hydrate 3 of Compound (1), Form D of Compound (1), Form A of Compound (1), Form B of Compound (1), Form C of Compound (1), or amorphous Compound (1).

As used herein, the term "water activity" ($a_w$) refers to a measure of the energy status of water in a solvent system. It is defined as the vapor pressure of a liquid divided by that of pure water at the same temperature. Specifically, it is defined as $a_w = p/p_0$ where p is the vapor pressure of water in the substance, and $p_0$ is the vapor pressure of pure water at the same temperature, or as $a_w = l_w * x_w$ where $l_w$ is the activity coefficient of water and $x_w$ is the mole fraction of water in the aqueous fraction. For example, pure water has a water activity value of 1.0. Water activity values can typically be obtained by either a capacitance hygrometer or a dew point hygrometer. Various types of water activity measuring instrument are also commercially available. Alternatively, water activity values of mixtures of two or more solvents can be calculated based on the amounts of the solvents and the known water activity values of the solvents.

One implementation of the present invention provides a method of preparing Hydrate 2 of Compound (1), wherein Compound (1) is represented by the following structural formula:

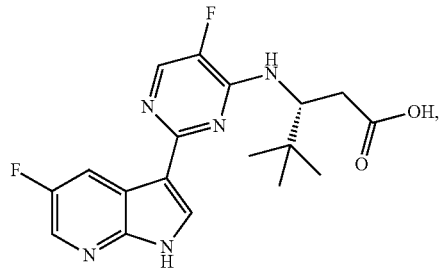 [SMILES: CC(C)(C)[C@@H](CC(=O)O)Nc1nc(-c2c[nH]c3ncc(F)cc23)ncc1F]

comprising:
    mixing Hydrate 1 of Compound (1) with a solvent system comprising water to generate a mixture; and
    removing at least some of the solvent system from the mixture to generate Hydrate 2 of Compound (1).

As used herein, the term "solvent system" refers to a solvent (e.g., water) or mixture of solvents (e.g., water and acetone or water and acetonitrol, or water and an alcohol).

In some implementations, the solvent system comprises water. In other implementations, the solvent system further comprises chlorobenzene, cyclohexane, 1,2-dichloroethene, dichloromethane, 1,2-dimethoxyethane, N,N-dimentylacetamide, N,N-dimethylformamide, 1,4-dioxane, 2-ethoxyethanol, formamide, hexane, 2-methoxyethanol, methylbutyl ketone, methylcyclohexane, N-methylpyrrolidone, nitromethane, pyridine, sulfolane, tetrahydrofuran, tetralin, tolune, 1,1,2-trichloroethene and xylene, acetic acid, acetone, anisole, 1-butanol, 2-butanol, butyl acetate, tert-butylmethyl ether, cumene, heptane, isobutyl acetate, isopropyl acetate, methyl acetate, 3-methyl-1-butanol, methylethyl ketone, methylisobutyl ketone, 2-methyl-1-propanol, ethyl acetate, ethyl ether, ethyl formate, pentane, 1-pentanol, 1-propanol, 2-propanol, propyl acetate, or any combination thereof.

In other examples, the solvent system further comprises chlorobenzene, cyclohexane, 1,2-dichloroethane, dichloromethane, 1,2-dimethoxyethane, formamide, hexane, 2-methoxyethanol, methylbutyl ketone, methylcyclohexane, nitromethane, tetralin, xylene, toluene, 1,1,2-trichloroethane, acetone, anisole, 1-butanol, 2-butanol, butyl acetate, t-butylmethylether, cumene, ethanol, ethyl acetate, ethyl ether, ethyl formate, heptane, isobutyl acetate, isopropyl acetate, methyl acetate, 3-methyl-1-butanol, methylethyl ketone, 2-methy-1-propanol, pentane, 1-propanol, 1-pentanol, 2-propanol, propyl acetate, tetrahydrofuran, or methyl tetrahydrofuran. In other examples, the solvent system further comprises 2-ethoxyethanol, ethyleneglycol, methanol, 2-methoxyethanol, 1-butanol, 2-butanol, 3-methyl-1-butanol, 2-methyl-1-propanol, ethanol, 1-pentanol, 1-propanol, 2-propanol, methylbutyl ketone, acetone, methylethyl ketone, methylisobutyl ketone, butyl acetate, isobutyl acetate, isopropyl acetate, methyl acetate, ethyl acetate, propyl acetate, pyridine, toluene, xylene, or any combination thereof.

In some examples, the solvent system further comprises acetone, n-propanol, isopropanol, iso-butylacetate, acetic acid, or any combination thereof. For example, the solvent system includes water and acetone, or water and isopropanol. In some instances, the solvent system includes water and acetone.

In some examples, the solvent system further comprises sodium chloride, dextrose, glycerine, or a surfactant.

In some implementations, the mixing is performed at a temperature in range from 20° C. to less than 40° C.

Solvent systems can be removed from the mixture to recrystallize a form of Compound (1) using any suitable methods (e.g., vacuum oven, vacuum, or the like).

Some implementations further comprise applying a vacuum to the mixture to remove the solvent system.

Another aspect provides a method of preparing Hydrate 3 of Compound (1), wherein Compound (1) is represented by the following structural formula:

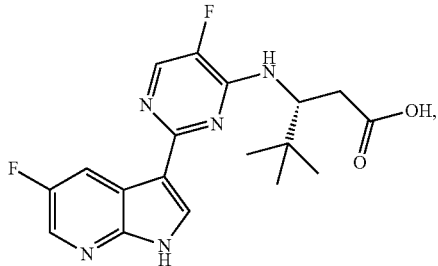 [SMILES: CC(C)(C)[C@@H](CC(=O)O)Nc1nc(-c2c[nH]c3ncc(F)cc23)ncc1F]

comprising:

mixing Hydrate 1 of Compound (1) or amorphous Compound (1) with a solvent system comprising water to generate a mixture;

heating the mixture; and removing at least some of the solvent system to generate Hydrate 3 of Compound (1).

In some implementations, the solvent system further comprises acetonitrile, chlorobenzene, cyclohexane, 1,2-dichloroethene, dichloromethane, 1,2-dimethoxyethane, N,N-dimentylacetamide, N,N-Dimethylformamide, 1,4-dioxane, 2-ethoxyethanol, formamide, hexane, 2-methoxyethanol, methylbutyl ketone, methylcyclohexane, N-methylpyrrolidone, nitromethane, pyridine, sulfolane, tetrahydrofuran (THF), tetralin, tolune, 1,1,2-trichloroethene, xylene, acetic acid, acetone, anisole, 1-butanol, 2-butanol, butyl acetate, tert-butylmethyl ether, cumene, heptane, isobutyl acetate, isopropyl acetate, methyl acetate, 3-methyl-1-butanol, methylethyl ketone, methylisobutyl ketone, 2-methyl-1-propanol, ethyl acetate, ethyl ether, ethyl formate, pentane, 1-pentanol, 1-propanol, 2-propanol, propyl acetate, or any combination thereof.

In some implementations, the solvent system further comprises chlorobenzene, cyclohexane, 1,2-dichloroethane, dichloromethane, 1,2-dimethoxyethane, formamide, hexane, 2-methoxyethanol, methylbutyl ketone, methylcyclohexane, nitromethane, tetralin, xylene, toluene, 1,1,2-trichloroethane, acetone, anisole, 1-butanol, 2-butanol, butyl acetate, t-butylmethylether, cumene, ethanol, ethyl acetate, ethyl ether, ethyl formate, heptane, isobutyl acetate, isopropyl acetate, methyl acetate, 3-methyl-1-butanol, methylethyl ketone, 2-methy-1-propanol, pentane, 1-propanol, 1-pentanol, 2-propanol, propyl acetate, tetrahydrofuran, methyl tetrahydrofuran, or any combination thereof.

And, in some implementations, the solvent system further comprises 2-ethoxyethanol, ethyleneglycol, methanol, 2-methoxyethanol, 1-butanol, 2-butanol, 3-methyl-1-butanol, 2-methyl-1-propanol, ethanol, 1-pentanol, 1-propanol, 2-propanol, methylbutyl ketone, acetone, methylethyl ketone, methylisobutyl ketone, butyl acetate, isobutyl acetate, isopropyl acetate, methyl acetate, ethyl acetate, propyl acetate, pyridine, toluene, xylene, or any combination thereof.

In other implementations, the solvent system further comprises isopropanol, acetonitrile, acetone, or any combination thereof.

In some implementations, the mixture is heated to a temperature of from about 45° C. to about 55° C. (e.g., about 50° C.).

Some implementations further comprise applying a vacuum to the mixture to remove the solvent system.

Another aspect provides a method of preparing Form D of Compound (1), wherein Compound (1) is represented by the following structural formula:

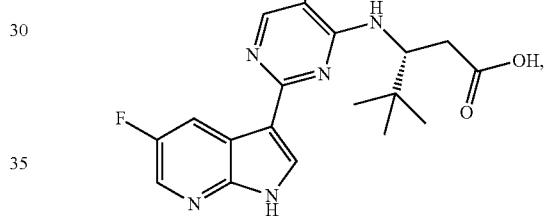

comprising:

mixing Hydrate 1, Hydrate 2, or Hydrate 3 of Compound (1), amorphous Compound (1), or any combination thereof with a solvent system in a solvent system comprising water to generate a mixture;

maintaining the temperature of the mixture to about room temperature; and removing at least some of the solvent system from the mixture.

In some implementations, the solvent system further comprises IPAC and a water activity of lower than about 0.25.

Another aspect provides a method of preparing Form A of Compound (1), wherein Compound (1) is represented by the following structural formula:

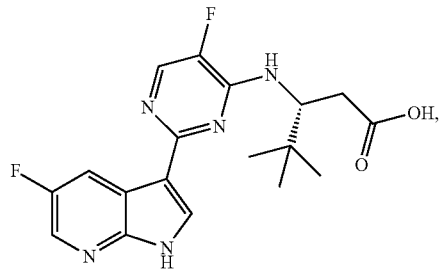 [SMILES: CC(C)(C)[C@@H](CC(=O)O)Nc1nc(-c2c[nH]c3ncc(F)cc23)ncc1F]

comprising:
heating amorphous Compound (1) to a temperature of at least about 150° C.; and
recrystallizing the heated amorphous Compound (1) to generate Form A of Compound (1).
In some implementations, the amorphous Compound (1) is heated to a temperature of from about 170° C. to 180° C. (e.g., about 175° C.).
Another aspect provides a method of preparing Form B of Compound (1), wherein Compound (1) is represented by the following structural formula:

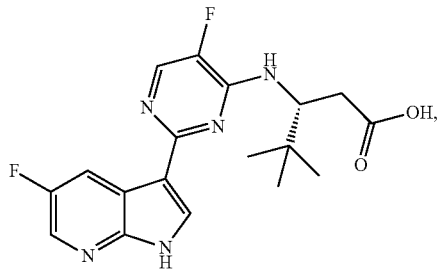 [SMILES: CC(C)(C)[C@@H](CC(=O)O)Nc1nc(-c2c[nH]c3ncc(F)cc23)ncc1F]

comprising:
heating Hydrate 3 of Compound (1) to a temperature of from about 110° C. to about 170° C.; and
recrystallizing the heated Hydrate of Compound (1) to generate Form A of Compound (1).
Another aspect provides a method of preparing Form C of Compound (1), wherein Compound (1) is represented by the following structural formula:

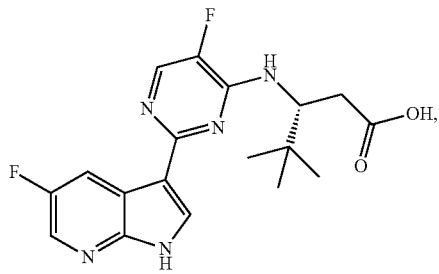 [SMILES: CC(C)(C)[C@@H](CC(=O)O)Nc1nc(-c2c[nH]c3ncc(F)cc23)ncc1F]

comprising:
mixing an IPA solvate of Compound (1) in n-propanol to generate a mixture;
heating the mixture; and
recrystallizing the heated IPA solvate of Compound (1) to generate Form C of Compound (1).
For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, New York: 2001, the entire contents of which are hereby incorporated by reference.
Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this invention, unless only one of the isomers is drawn specifically. As would be understood to one skilled in the art, a substituent can freely rotate around any rotatable bonds. For example, a substituent drawn as

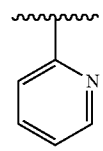

also represents

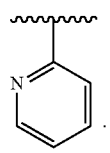

.

Therefore, single stereochemical isomers as well as enantiomeric, diastereomeric, cis/trans, conformational, and rotational mixtures of the present compounds are within the scope of the invention.
Unless otherwise indicated, all tautomeric forms of the compounds of the invention are within the scope of the invention.
Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, especially deuterium (D) analogs, can also be therapeutically useful.
The compounds described herein are defined herein by their chemical structures and/or chemical names. Where a compound is referred to by both a chemical structure and a chemical name, and the chemical structure and chemical name conflict, the chemical structure is determinative of the compound's identity.
It will be appreciated by those skilled in the art that the compounds in accordance with the present invention can contain a chiral center. The compounds of formula may thus exist in the form of two different optical isomers (i.e. (+) or (−) enantiomers). All such enantiomers and mixtures thereof including racemic mixtures are included within the scope of the invention. The single optical isomer or enantiomer can be obtained by method well known in the art, such as chiral HPLC, enzymatic resolution and chiral auxiliary.
In one embodiment, the compounds in accordance with the present invention are provided in the form of a single enantiomer at least 95%, at least 97% and at least 99% free of the corresponding enantiomer.
In a further embodiment, the compounds in accordance with the present invention are in the form of the (+) enantiomer at least 95% free of the corresponding (−) enantiomer.
In a further embodiment, the compounds in accordance with the present invention are in the form of the (+) enantiomer at least 97% free of the corresponding (−) enantiomer.

In a further embodiment, the compounds in accordance with the present invention are in the form of the (+) enantiomer at least 99% free of the corresponding (−) enantiomer.

In a further embodiment, the compounds in accordance with the present invention are in the form of the (−) enantiomer at least 95% free of the corresponding (+) enantiomer.

In a further embodiment, the compounds in accordance with the present invention are in the form of the (−) enantiomer at least 97% free of the corresponding (+) enantiomer.

In a further embodiment the compounds in accordance with the present invention are in the form of the (−) enantiomer at least 99% free of the corresponding (+) enantiomer.

III. USES OF COMPOUND (1) AND PHARMACEUTICALLY ACCEPTABLE SALTS THEREOF

One aspect of the present invention is generally related to the use of Compound (1) and its pharmaceutically acceptable salts, including the various solid forms (e.g., Hydrate 2, Hydrate 3, Form D, Form A, Form B, Form C, or amorphous) of Compound (1)) as described above, for inhibiting the replication of influenza viruses in a biological sample or in a patient, for reducing the amount of influenza viruses (reducing viral titer) in a biological sample or in a patient, and for treating influenza in a patient. Hereinafter unless specifically indicated otherwise, Compound (1) and its pharmaceutically acceptable salts, including the various solid forms (e.g., Hydrate 2, Hydrate 3, Form D, Form A, Form B, Form C, or amorphous) of Compound (1)) described above, are referred to generally as "compounds".

In one embodiment, the present invention is generally related to the use of the compounds disclosed herein (e.g., in pharmaceutically acceptable compositions) for any of the uses specified above.

In yet another embodiment, the compounds disclosed herein can be used to reduce viral titre in a biological sample (e.g. an infected cell culture) or in humans (e.g. lung viral titre in a patient).

The terms "influenza virus mediated condition", "influenza infection", or "Influenza", as used herein, are used interchangeable to mean the disease caused by an infection with an influenza virus.

Influenza is an infectious disease that affects birds and mammals caused by influenza viruses. Influenza viruses are RNA viruses of the family Orthomyxoviridae, which comprises five genera: Influenza virus A, Influenza virus B, Influenza virus C, ISA virus and Thogoto virus. Influenza virus A genus has one species, influenza A virus which can be subdivided into different serotypes based on the antibody response to these viruses: H1N1, H2N2, H3N2, H5N1, H7N7, H1N2, H9N2, H7N2, H7N3 and H10N7. Additional examples of influenza A virus include H3N8 and H7N9. Influenza virus B genus has one species, influenza B virus. Influenza B almost exclusively infects humans and is less common than influenza A. Influenza virus C genus has one species, Influenza virus C virus, which infects humans and pigs and can cause severe illness and local epidemics. However, Influenza virus C is less common than the other types and usually seems to cause mild disease in children.

In some embodiments of the invention, influenza or influenza viruses are associated with Influenza virus A or B. In some embodiments of the invention, influenza or influenza viruses are associated with Influenza virus A. In some specific embodiments of the invention, Influenza virus A is H1N1, H2N2, H3N2 or H5N1. In some specific embodiments of the invention, Influenza virus A is H1N1, H3N2, H3N8, H5N1, and H7N9. In some specific embodiments of the invention, Influenza virus A is H1N1, H3N2, H3N8, and H5N1.

In humans, common symptoms of influenza are chills, fever, pharyngitis, muscle pains, severe headache, coughing, weakness, and general discomfort. In more serious cases, influenza causes pneumonia, which can be fatal, particularly in young children and the elderly. Although it is often confused with the common cold, influenza is a much more severe disease and is caused by a different type of virus. Influenza can produce nausea and vomiting, especially in children, but these symptoms are more characteristic of the unrelated gastroenteritis, which is sometimes called "stomach flu" or "24-hour flu".

Symptoms of influenza can start quite suddenly one to two days after infection. Usually the first symptoms are chills or a chilly sensation, but fever is also common early in the infection, with body temperatures ranging from 38° C.-39° C. (approximately 100° F.-103° F.). Many people are so ill that they are confined to bed for several days, with aches and pains throughout their bodies, which are worse in their backs and legs. Symptoms of influenza may include: body aches, especially joints and throat, extreme coldness and fever, fatigue, headache, irritated watering eyes, reddened eyes, skin (especially face), mouth, throat and nose, abdominal pain (in children with influenza B). Symptoms of influenza are non-specific, overlapping with many pathogens ("influenza-like illness"). Usually, laboratory data is needed in order to confirm the diagnosis.

The terms, "disease", "disorder", and "condition" may be used interchangeably here to refer to an influenza virus mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In a preferred embodiment, the subject is a "human".

The term "biological sample", as used herein, includes, without limitation, cell cultures or extracts thereof; biopsied material obtained from a mammal or extracts thereof; blood, saliva, urine, feces, semen, tears, or other body fluids or extracts thereof.

As used herein, "multiplicity of infection" or "MOI" is the ratio of infectious agents (e.g. phage or virus) to infection targets (e.g. cell). For example, when referring to a group of cells inoculated with infectious virus particles, the multiplicity of infection or MOI is the ratio defined by the number of infectious virus particles deposited in a well divided by the number of target cells present in that well.

As used herein the term "inhibition of the replication of influenza viruses" includes both the reduction in the amount of virus replication (e.g. the reduction by at least 10%) and the complete arrest of virus replication (i.e., 100% reduction in the amount of virus replication). In some embodiments, the replication of influenza viruses are inhibited by at least 50%, at least 65%, at least 75%, at least 85%, at least 90%, or at least 95%.

Influenza virus replication can be measured by any suitable method known in the art. For example, influenza viral titre in a biological sample (e.g. an infected cell culture) or in humans (e.g. lung viral titre in a patient) can be measured. More specifically, for cell based assays, in each case cells are cultured in vitro, virus is added to the culture in the presence or absence of a test agent, and after a suitable length of time a virus-dependent endpoint is evaluated. For typical assays, the Madin-Darby canine kidney cells (MDCK) and the standard tissue culture adapted influenza strain, A/Puerto Rico/8/34 can be used. A first type of cell assay that can be used in the invention depends on death of the infected target cells, a process called cytopathic effect (CPE), where virus infection causes exhaustion of the cell resources and eventual lysis of the cell. In the first type of cell assay, a low fraction of cells in the wells of a microtiter plate are infected (typically $\frac{1}{10}$ to $\frac{1}{1000}$), the virus is allowed to go through several rounds of replication over 48-72 hours, then the amount of cell death is measured using a decrease in cellular ATP content compared to uninfected controls. A second type of cell assay that can be employed in the invention depends on the multiplication of virus-specific RNA molecules in the infected cells, with RNA levels being directly measured using the branched-chain DNA hybridization method (bDNA). In the second type of cell assay, a low number of cells are initially infected in wells of a microtiter plate, the virus is allowed to replicate in the infected cells and spread to additional rounds of cells, then the cells are lysed and viral RNA content is measured. This assay is stopped early, usually after 18-36 hours, while all the target cells are still viable. Viral RNA is quantitated by hybridization to specific oligonucleotide probes fixed to wells of an assay plate, then amplification of the signal by hybridization with additional probes linked to a reporter enzyme.

As used herein a "viral titer" or "titre" is a measure of virus concentration. Titer testing can employ serial dilution to obtain approximate quantitative information from an analytical procedure that inherently only evaluates as positive or negative. The titer corresponds to the highest dilution factor that still yields a positive reading; for example, positive readings in the first 8 serial twofold dilutions translate into a titer of 1:256. A specific example is viral titer. To determine the titer, several dilutions will be prepared, such as $10^{-1}$, $10^{-2}$, $10^{-3}$, $10^{-4}$, $10^{-5}$, $10^{-6}$, $10^{-7}$, $10^{-8}$. The lowest concentration of virus that still infects cells is the viral titer.

As used herein, the terms "treat", "treatment" and "treating" refer to both therapeutic and prophylactic treatments. For example, therapeutic treatments includes the reduction or amelioration of the progression, severity and/or duration of influenza viruses mediated conditions, or the amelioration of one or more symptoms (specifically, one or more discernible symptoms) of influenza viruses mediated conditions, resulting from the administration of one or more therapies (e.g., one or more therapeutic agents such as a compound or composition of the invention). In specific embodiments, the therapeutic treatment includes the amelioration of at least one measurable physical parameter of an influenza virus mediated condition. In other embodiments the therapeutic treatment includes the inhibition of the progression of an influenza virus mediated condition, either physically by, e.g., stabilization of a discernible symptom, physiologically by, e.g., stabilization of a physical parameter, or both. In other embodiments the therapeutic treatment includes the reduction or stabilization of influenza viruses mediated infections. Antiviral drugs can be used in the community setting to treat people who already have influenza to reduce the severity of symptoms and reduce the number of days that they are sick.

The term "chemotherapy" refers to the use of medications, e.g. small molecule drugs (rather than "vaccines") for treating a disorder or disease.

The terms "prophylaxis" or "prophylactic use" and "prophylactic treatment" as used herein, refer to any medical or public health procedure whose purpose is to prevent, rather than treat or cure a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a person with the disease. The term "chemoprophylaxis" refers to the use of medications, e.g. small molecule drugs (rather than "vaccines") for the prevention of a disorder or disease.

As used herein, prophylactic use includes the use in situations in which an outbreak has been detected, to prevent contagion or spread of the infection in places where a lot of people that are at high risk of serious influenza complications live in close contact with each other (e.g. in a hospital ward, daycare center, prison, nursing home, or the like). It also includes the use among populations who require protection from the influenza but who either do not get protection after vaccination (e.g., due to weak immune system), or when the vaccine is unavailable to them, or when they cannot get the vaccine because of side effects. It also includes use during the two weeks following vaccination, since during that time the vaccine is still ineffective. Prophylactic use may also include treating a person who is not ill with the influenza or not considered at high risk for complications, in order to reduce the chances of getting infected with the influenza and passing it on to a high-risk person in close contact with him (for instance, healthcare workers, nursing home workers, or the like).

According to the US CDC, an influenza "outbreak" is defined as a sudden increase of acute febrile respiratory illness (AFRI) occurring within a 48 to 72 hour period, in a group of people who are in close proximity to each other (e.g. in the same area of an assisted living facility, in the same household, etc.) over the normal background rate or when any subject in the population being analyzed tests positive for influenza. One case of confirmed influenza by any testing method is considered an outbreak.

A "cluster" is defined as a group of three or more cases of AFRI occurring within a 48 to 72 hour period, in a group of people who are in close proximity to each other (e.g. in the same area of an assisted living facility, in the same household, etc.).

As used herein, the "index case", "primary case" or "patient zero" is the initial patient in the population sample of an epidemiological investigation. When used in general to refer to such patients in epidemiological investigations, the term is not capitalized. When the term is used to refer to a specific person in place of that person's name within a report on a specific investigation, the term is capitalized as Patient Zero. Often scientists search for the index case to determine how the disease spread and what reservoir holds the disease in between outbreaks. Note that the index case is the first patient that indicates the existence of an outbreak. Earlier cases may be found and are labeled primary, secondary, tertiary, and the like.

In one embodiment, the methods of the invention are a preventative or "pre-emptive" measure to a patient, specifically a human, having a predisposition to complications resulting from infection by an influenza virus. The term "pre-emptive" or "pre-emptively", as used herein, for example, in 'pre-emptive' use, is the prophylactic use in situations in which an "index case" or an "outbreak" has been confirmed, in order to prevent the spread of infection in the rest of the community or population group.

In another embodiment, the methods of the invention are applied as a "pre-emptive" measure to members of a community or population group, specifically humans, in order to prevent the spread of infection.

As used herein, an "effective amount" refers to an amount sufficient to elicit the desired biological response. In the present invention the desired biological response is to inhibit the replication of influenza virus, to reduce the amount of influenza viruses or to reduce or ameliorate the severity, duration, progression, or onset of a influenza virus infection, prevent the advancement of an influenza viruses infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other antiviral agents, e.g., when co-administered with an anti-influenza medication, an 'effective amount' of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, the compounds disclosed herein can be administered to a subject in a dosage range from between approximately 0.01 mg/kg to 100 mg/kg body weight/day for therapeutic or prophylactic treatment.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compounds described herein required to treat, to prevent, inhibit (fully or partially) or arrest the progress of the disease.

Dosages of the compounds described herein can range from 0.01 mg/kg to 100 mg/kg body weight/day, 0.01 mg/kg to 50 mg/kg body weight/day, 0.1 mg/kg to 50 mg/kg body weight/day, or 1 mg/kg to 25 mg/kg body weight/day. It is understood that the total amount per day can be administered in a single dose or can be administered in multiple dosing, such as twice a day (e.g., every 12 hours), three times a day (e.g., every 8 hours), or four times a day (e.g., every 6 hours).

In some embodiments, dosages of the compounds described herein (e.g., Hydrate 2, Hydrate 3, Form D, Form A, Form B, Form C, or amorphous Compound (1)) are in a range of 100 mg to 1,600 mg, such as 400 mg to 1,600 mg or 400 mg to 1,200 mg. Each dose can be taken once a day (QD), twice per day (e.g., approximately every 12 hours (BID)), or three times per day (e.g., approximately every 8 hours (TID)). It is noted that any combinations of QD, BID, and TID can be employed, as desired, such as BID on day 1, followed by QD thereafter.

In some embodiments, dosages of the compounds described herein (e.g., Compound (1) and its pharmaceutically acceptable salts thereof, including the various solid forms (e.g., Hydrate 2, Hydrate 3, Form D, Form A, Form B, Form C, or amorphous) of Compound (1)) are in a range of 100 mg to 1,600 mg, such as 400 mg to 1,600 mg or 400 mg to 1,200 mg. Each dose can be taken once a day (QD), twice per day (e.g., every 12 hours (BID)), or three times per day (e.g., q8 h (TID)). It is noted that any combinations of QD, BID, and TID can be employed, as desired, such as BID on day 1, followed by QD thereafter, or, when a loading dosage is employed on day 1, BID on day 2, followed by QD thereafter.

In one specific embodiment, dosages of the compounds described herein are 400 mg to 1,600 mg, 400 mg to 1,200 mg, or 600 mg to 1,200 mg once a day. In another specific embodiment, dosages of the compounds described herein are 400 mg to 1,600 mg, 400 mg to 1,200 mg, or 300 mg to 900 mg twice a day. In yet another specific embodiment, dosages of the compounds described herein are 400 mg to 1,000 mg once a day. In yet another specific embodiment, dosages of the compounds described herein are 600 mg to 1,000 mg once a day. In yet another specific embodiment, dosages of the compounds described herein are 600 mg to 800 mg once a day. In yet another specific embodiment, dosages of the compounds described herein are 400 mg to 800 mg twice a day (e.g., 400 mg to 800 mg every 12 hours). In yet another specific embodiment, dosages of the compounds described herein are 400 mg to 600 mg twice a day.

In some embodiments, a loading dosage regimen is employed. In one specific embodiment, a loading dose of 400 mg to 1,600 mg is employed on day 1 of treatment. In another specific embodiment, a loading dose of 600 mg to 1,600 mg is employed on day 1 of treatment. In another specific embodiment, a loading dose of 800 mg to 1,600 mg is employed on day 1 of treatment. In yet another specific embodiment, a loading dose of 900 mg to 1,600 mg is employed on day 1 of treatment. In yet another specific embodiment, a loading dose of 900 mg to 1,200 mg is employed on day 1 of treatment. In yet another specific embodiment, a loading dose of 900 mg is employed on day 1 of treatment. In yet another specific embodiment, a loading dose of 1,000 mg is employed on day 1 of treatment. In yet another specific embodiment, a loading dose of 1,200 mg is employed on day 1 of treatment.

In one specific embodiment, the dosage regimen of the compounds described herein employs a loading dosage of 600 mg to 1,600 mg on day 1 and with a regular dosage of 300 mg to 1,200 mg for the rest of the treatment duration. Each regular dose can be taken once a day, twice a day, or three times a day, or any combination thereof. In a further specific embodiment, a loading dosage of 900 mg to 1,600 mg, such as 900 mg, 1,200 mg, or 1,600 mg, is employed. In another further specific embodiment, a loading dosage of 900 mg to 1,200 mg, such as 900 mg or 1,200 mg, is employed. In yet another further specific embodiment, a regular dosage of 400 mg to 1,200 mg, such as 400 mg, 600 mg, or 800 mg, is employed for the rest of the treatment duration. In yet another further specific embodiment, a regular dosage of 400 mg to 1,000 mg for the rest of the treatment duration. In yet another further specific embodiment, a regular dosage of 400 mg to 800 mg is employed for the rest of the treatment duration. In yet another further specific embodiment, a regular dosage of 300 mg to 900 mg twice a day is employed. In yet another further specific embodiment, a regular dosage of 600 mg to 1,200 mg once a day is employed. In yet another further specific embodiment, a regular dosage of 600 mg twice a day on day 2, followed by 600 mg once a day for the rest of the treatment duration.

For therapeutic treatment, the compounds described herein can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). Alternatively, for therapeutic treatment, the compounds described herein can be administered to a patient within, for example, 96 hours of onset of symptoms. The therapeutic treatment can last for any suitable duration, for example, for 3 days, 4 days, 5 days, 7 days, 10 days, 14 days, etc. For prophylactic treatment during a community outbreak, the compounds described herein can be administered to a patient within, for example, 2 days of onset of symptoms in the index case, and can be continued for any suitable duration, for example, for 7 days, 10 days, 14 days, 20 days, 28 days, 35 days, 42 days, etc., up to the entire flu season. A flu season is an annually-recurring time period characterized by the prevalence of outbreaks of influenza. Influenza activity can sometimes be predicted and even tracked geographically. While the beginning of major flu activity in each season varies by location, in any specific location these minor epidemics usually take 3-4 weeks to peak and another 3-4 weeks to significantly diminish. Typically, Centers for Disease Control (CDC) collects, compiles and analyzes information on influenza activity year round in the United States and produces a weekly report from October through mid-May.

In one embodiment, the therapeutic treatment lasts for 1 day to an entire flu season. In one specific embodiment, the therapeutic treatment lasts for 3 days to 14 days. In another specific embodiment, the therapeutic treatment lasts for 5 days to 14 days. In another specific embodiment, the therapeutic treatment lasts for 3 days to 10 days. In yet another specific embodiment, the therapeutic treatment lasts for 4 days to 10 days. In yet another specific embodiment, the therapeutic treatment lasts for 5 days to 10 days. In yet another specific embodiment, the therapeutic treatment lasts for 4 days to 7 days (e.g., 4 days, 5 days, 6 days, or 7 days). In yet another specific embodiment, the therapeutic treatment lasts for 5 days to 7 days (e.g., 5 days, 6 days, or 7 days). In one specific embodiment, the prophylactic treatment lasts up to the entire flu season.

In one specific embodiment, the compounds described herein are administered to a patient for 3 days to 14 days (e.g., 5 days to 14 days) with a loading dosage of 900 mg to 1,600 mg on day 1 and with a regular dosage of 300 mg to 1,200 mg for the rest of the treatment duration. In another specific embodiment, the compounds described herein are administered to a patient for 3 days to 14 days (e.g., 5 days to 14 days) with a loading dosage of 900 mg to 1,200 mg on day 1 and with a regular dosage of 400 mg to 1,000 mg for the rest of the treatment duration. In yet another specific embodiment, the compounds described herein are administered to a patient for 3 days to 14 days (e.g., 5 days to 14 days) with a loading dosage of 900 mg to 1,200 mg on day 1 and with a regular dosage of 400 mg to 800 mg for the rest of the treatment duration. In yet another specific embodiment, the compounds described herein are administered to a patient for 3 days to 14 days (e.g., 5 days to 14 days) with a loading dosage of 900 mg to 1,200 mg on day 1 and with a regular dosage of 400 mg to 800 mg for the rest of the treatment duration. Each dose can be taken once a day, twice a day, or three times a day, or any combination thereof.

In one specific embodiment, the compounds described herein are administered to a patient for 3 days to 14 days with a loading dosage of 900 mg to 1,600 mg on day 1 and with a regular dosage of 600 mg to 1,000 mg once a day for the rest of the treatment duration. In another specific embodiment, the compounds described herein are administered to a patient for 3 days to 14 days with a loading dosage of 900 mg to 1,200 mg on day 1 and with a regular dosage of 600 mg to 800 mg (e.g., 600 mg, 650 mg, 700 mg, 750 mg, or 800 mg) once a day for the rest of the treatment duration. In some embodiments, the treatment duration is for 4 days to 10 days, 5 days to 10 days, or 5 days to 7 days.

In one specific embodiment, the compounds described herein are administered to a patient for 3 days to 14 days with a loading dosage of 900 mg to 1,600 mg on day 1 and with a regular dosage of 400 mg to 800 mg twice a day for the rest of the treatment duration. In another specific embodiment, the compounds described herein are administered to a patient for 3 days to 14 days with a loading dosage of 900 mg to 1,200 mg on day 1 and with a regular dosage of 400 mg to 600 mg (e.g., 400 mg, 450 mg, 500 mg, 550 mg, or 600 mg) twice a day for the rest of the treatment duration. In some embodiments, the duration is for 4 days to 10 days, 5 days to 10 days, or 5 days to 7 days.

In one specific embodiment, the compounds described herein are administered to a patient for 4 days or 5 days with a loading dosage of 900 mg to 1,200 mg (e.g., 900 mg or 1,200 mg) on day 1 and with a regular dosage of 400 mg to 600 mg (e.g., 400 mg or 600 mg) twice a day for the rest of the treatment duration (e.g., days 2 through 4, or days 2 through 5). In another specific embodiment, the compounds described herein are administered to a patient for 4 days or 5 days with a loading dosage of 900 mg to 1,200 mg (e.g., 900 mg or 1,200 mg) on day 1 and with a regular dosage of 600 mg to 800 mg (e.g., 600 mg or 800 mg) once a day for the rest of the treatment duration.

Various types of administration methods can be employed in the invention, and are described in detail below under the section entitled "Administration Methods".

Various types of administration methods can be employed in the invention, and are described in detail below under the section entitled "Administration Methods".

IV. COMBINATION THERAPY

An effective amount can be achieved in the method or pharmaceutical composition of the invention employing a compound of the invention (including a pharmaceutically acceptable salt or solvate (e.g., hydrate)) alone or in combination with an additional suitable therapeutic agent, for example, an antiviral agent or a vaccine. When "combination therapy" is employed, an effective amount can be achieved using a first amount of a compound of the invention and a second amount of an additional suitable therapeutic agent (e.g., an antiviral agent or vaccine).

In another embodiment of this invention, a compound of the invention and the additional therapeutic agent, are each administered in an effective amount (i.e., each in an amount which would be therapeutically effective if administered alone). In another embodiment, a compound of the invention and the additional therapeutic agent, are each administered in an amount which alone does not provide a therapeutic effect (a sub-therapeutic dose). In yet another embodiment, a compound of the invention can be administered in an effective amount, while the additional therapeutic agent is administered in a sub-therapeutic dose. In still another embodiment, a compound of the invention can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds of the co-administration in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order.

In one embodiment, the present invention is directed to methods of combination therapy for inhibiting Flu viruses replication in biological samples or patients, or for treating or preventing Influenza virus infections in patients using the compounds described herein. Accordingly, pharmaceutical compositions of the invention also include those comprising an inhibitor of Flu virus replication of this invention in combination with an anti-viral compound exhibiting anti-Influenza virus activity.

Methods of use of the compounds described herein and compositions of the invention also include combination of chemotherapy with a compound or composition of the invention, or with a combination of a compound or composition of this invention with another anti-viral agent and vaccination with a Flu vaccine.

When co-administration involves the separate administration of the first amount of a compound of the invention and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of the invention and the second therapeutic agent can be administered in any order within 24 hours of each other, within 16 hours of each other, within 8 hours of each other, within 4 hours of each other, within 1 hour of each other or within 30 minutes of each other.

More, specifically, a first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of co-administration of a first amount of a compound of the invention and a second amount of an additional therapeutic agent can result in an enhanced or synergistic therapeutic effect, wherein the combined effect is greater than the additive effect that would result from separate administration of the first amount of a compound of the invention and the second amount of an additional therapeutic agent.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) can permit the use of lower dosages of one or more of the therapies and/or less frequent administration of said therapies to a subject. The ability to utilize lower dosages of a therapy (e.g., a prophylactic or therapeutic agent) and/or to administer said therapy less frequently can reduce the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

When the combination therapy using the compounds of the present invention is in combination with a Flu vaccine, both therapeutic agents can be administered so that the period of time between each administration can be longer (e.g. days, weeks, or months).

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

Specific examples that can be co-administered with a compound described herein include neuraminidase inhibitors, such as oseltamivir (Tamiflu®) and Zanamivir (Rlenza®), viral ion channel (M2 protein) blockers, such as amantadine (Symmetrel®) and rimantadine (Flumadine®), and antiviral drugs described in WO 2003/015798, including T-705 under development by Toyama Chemical of Japan. (See also Ruruta et al., Antiviral Research, 82: 95-102 (2009), "T-705 (flavipiravir) and related compounds: Novel broad-spectrum inhibitors of RNA viral infections"). In some embodiments, the compounds described herein can be co-administered with a traditional influenza vaccine.

In some embodiments, the compounds described herein (e.g., Compound (1) and its pharmaceutically acceptable salts thereof, such as Hydrate 2, Hydrate 3, Form D, Form A, Form B, Form C, or amorphous Compound (1))) can be co-administered with zanamivir. In some embodiments, the compounds described herein can be co-administered with flavipiravir (T-705). In some embodiments, the compounds described herein can be co-administered with oseltamivir. In some embodiments, the compounds described herein can be co-administered with amantadine or rimantadine. Oseltamivir can be administered in a dosage regimen specified in its label. In some specific embodiments, it is administered 75 mg twice a day, or 150 mg once a day.

Pharmaceutical Compositions

The compounds described herein can be formulated into pharmaceutical compositions that further comprise a pharmaceutically acceptable carrier, diluent, adjuvant or vehicle. In one embodiment, the present invention relates to a pharmaceutical composition comprising a compound of the invention described above, and a pharmaceutically acceptable carrier, diluent, adjuvant or vehicle. In one embodiment, the present invention is a pharmaceutical composition comprising an effective amount of a compound of the present invention or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount". The term "therapeutically effective amount" refers to an amount effective in treating and/or ameliorating an influenza virus infection in a patient infected with influenza. The term "prophylactically effective amount" refers to an amount effective in preventing and/or substantially lessening the chances or the size of influenza virus infection outbreak. Specific examples of effective amounts are described above in the section entitled Uses of Disclosed Compounds.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this invention. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

V. ADMINISTRATION METHODS

The compounds and pharmaceutically acceptable compositions described above can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., 1 to 4 or more times per day). When multiple daily doses are used, the unit dosage form can be the same or different for each dose.

VI. GENERIC SCHEMES

Compound (1) may be generated according to the general synthetic scheme provided below:

Scheme 1:

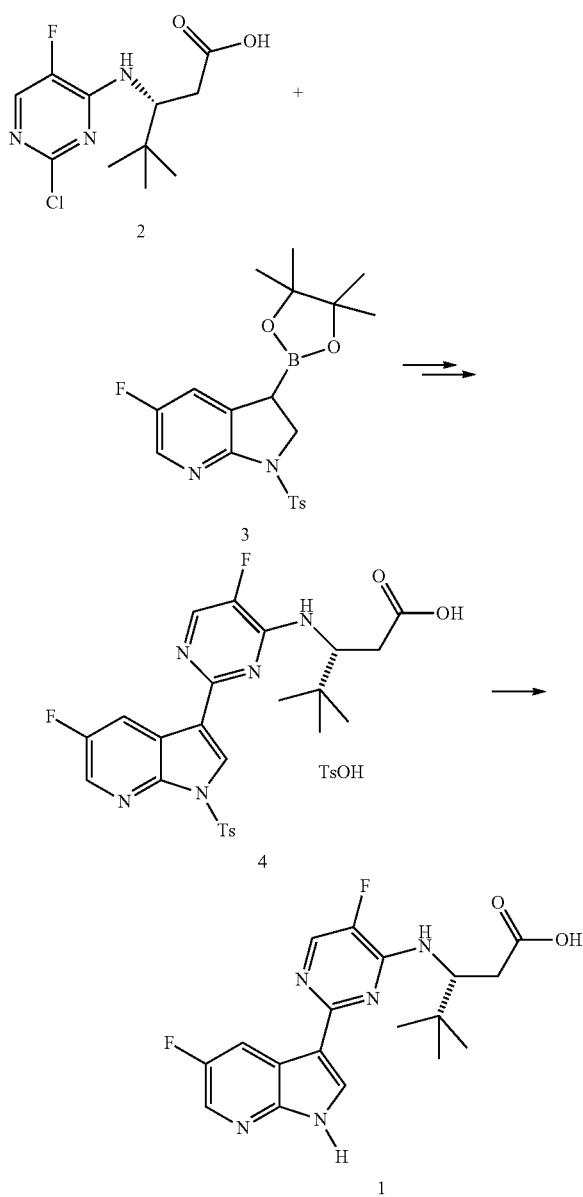

In the scheme above, the coupling of Compound 2 and Compound 3 can be achieved by, for example, the Suzuki coupling reaction, using a catalyst such as the palladium catalyst PdCl$_2$(Amphos)$_2$. The Suzuki coupling of Compound 2 and Compound 3 can also be performed in the presence of a solvent, such as acetonitrile or a mixture of acetonitrile and water, and a base, such as Hunig's base or triethylamine. The palladium catalyst can be removed from the coupled product (<1 ppm) by contacting the product with a resin, such as MP-TMT, in an organic solvent such as isopropyl acetate, and subsequent removal of the resin by filtration. Isolation of the product can be achieved by salt formation of the product with a strong acid, such asp-toluene sulfonic acid, in an organic solvent such as a mixture of isopropyl acetate and 2-methyltetrahydrofuran, and subsequent filtration of the product.

Isolation of Hydrate 1 of Compound (1) (hemi-hydrate) in high purity can be produced by contacting Compound 4 with a base such as lithium hydroxide in, for example, a biphasic solution of 2-methyltetrahydrofuran and water. Isolation of the product can be achieved by first adjusting the pH of the resulting solution to 5.5-6, followed by removal of the aqueous phase, and optionally washing the organic phase with a pH 6 buffer, such as a phosphate buffer.

VII. EXAMPLES

Example 1: General Methods of XRPD, $C^{13}$ Solid State NMR, DSC Measurements

Thermogravimetric analysis (TGA)

Thermogravimetric analysis (TGA) was performed on the TA Instruments TGA model Q5000. The solid sample was placed in a tarred platinum sample pan and heated at 10° C./min to 300° C. from room temperature.

DSC Measurements

DSC was conducted on a TA Instruments DSC Q2000 V24.3 Build 115 instrument. Approximately 1-2 mg of solid sample powder was hermetically sealed in an aluminum pin hole pan. The sample cell was generally heated at 10° C./min to 350° C. from room temperature under nitrogen purge.

SSNMR experimental

Solid state nuclear magnetic spectroscopy (SSNMR) spectra were acquired on the Bruker-Biospin 400 MHz Advance III wide-bore spectrometer equipped with Bruker-Biospin 4 mm HFX probe. Samples were packed into 4 mm ZrO2 rotors (approximately 70 mg or less, depending on sample availability). Magic angle spinning (MAS) speed of typically 12.5 kHz was applied. The temperature of the probe head was set to 275K to minimize the effect of frictional heating during spinning. The proton relaxation time was measured using $^1$H MAS $T_1$ saturation recovery relaxation experiment in order to set up proper recycle delay of the $^{13}$C cross-polarization (CP) MAS experiment. The recycle delay of $^{13}$C CPMAS experiment was adjusted to be at least 1.2 times longer than the measured $^1$H $T_1$ relaxation time in order to maximize the carbon spectrum signal-to-noise ratio. The CP contact time of $^{13}$C CPMAS experiment was set to 2 ms. A CP proton pulse with linear ramp (from 50% to 100%) was employed. The Hartmann-Hahn match was optimized on external reference sample (glycine). Fluorine spectra were acquired using proton decoupled MAS setup with recycled delay set to approximately 5 times of the measured $^{19}$F $T_1$ relaxation time. The fluorine relaxation time was measured using proton decoupled $^{19}$F MAS $T_1$ saturation recovery relaxation experiment. Both carbon and fluorine spectra were acquired with SPINAL 64 decoupling was used with the field strength of approximately 100 kHz. The chemical shift was referenced against external standard of adamantane with its upfield resonance set to 29.5 ppm.

Bruker D8 Discover XRPD Experimental Details

The XRPD patterns were acquired at room temperature in reflection mode using a Bruker D8 Discover diffractometer (Asset Tag V012842) equipped with a sealed tube source and a Hi-Star area detector (Bruker AXS, Madison, Wis.). The X-Ray generator was operating at a voltage of 40 kV and a current of 35 mA. The powder sample was placed in an aluminum holder. Two frames were registered with an exposure time of 120 s each. The data was subsequently integrated over the range of 4.5°-39° 2θ with a step size of 0.02° and merged into one continuous pattern.

Example 2A: Synthesis of Hydrate 1 of Compound (1) (Hemi-Hydrate)

Compound (1) can be prepared as described in WO 2013/019828.

Alternatively, Compound (1) can be generated as provided below:

Synthesis of tosylate salt of (R)-3-((5-fluoro-2-(5-fluoro-1-tosyl-1H-pyrrolo[2,3-b]pyridin-3-yl)pyrimidin-4-yl)amino)-4,4-dimethylpentanoic acid (4)

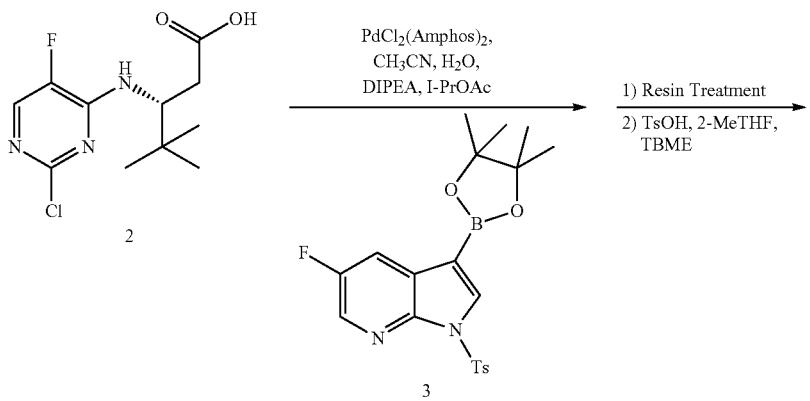

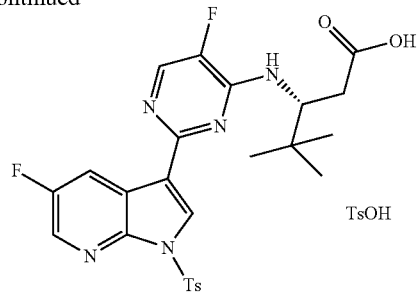

4

The Suzuki coupling was performed under a $N_2$ atmosphere by first taking up the chloropyrimidine (2) (1.73 kg) and boronic ester (3) (3.26 kg) in 9 vol $CH_3CN$ and 1 vol water. The stiff slurry was sparged with $N_2$ for 30 minutes followed by addition of 0.5 mol % $PdCl_2(Amphos)_2$ as catalyst. Hunig's base (3 eq.) was added over 30 minutes and the now thin slurry heated to 71° C. overnight. The reaction was judged complete at 99.3% AUC and the mixture cooled to 20° C. Celite (590 g) was slurried with the reaction mixture for 1 h and then passed through a pad of Celite to remove most of the Pd. The cake was washed with i-PrOAc and the solution solvent switched to 6 volumes of i-PrOAc. A 5 wt % aqueous solution of NaCl (3 vol) was added and the mixture adjusted to pH 5 with of 6N HCl. The aqueous layer was drained to waste and the organic layer treated with 1.21 kg of MP-TMT (35 wt % based on theoretical product amount) overnight. With the Pd level brought below <1 ppm, the resin was removed by filtration. The filtration was slow so the mixture was diluted with 4.3 L of i-PrOAc. After the volume of the mixture was brought to 8 volumes by vacuum distillation, a TsOH solution in 1.4 volumes of 2-MeTHF was added to give stiff slurry. TBME (20 vol) was added over 1 hour at 20° C.-25° C. and the slurry stirred overnight. The solids were collected by suction filtration and dried on the funnel for 2 days to give 4240 g (97% yield; 1 ppm Pd; 99.31% AUC, Compound (1)—0.31% AUC, chloropyrimidine (2)—0.12% AUC, RRT 1.01-2.08% AUC, RRT 1.06-0.36% AUC) of (4)●p-TsOH.

Synthesis of Hydrate 1 of Compound (1) (Hemi-Hydrate)

The TsOH salt (4) (4.14 kg) was taken up in 6 vol of 2-MeTHF as a slurry to which 5 eq. of LiOH in 4 vol water were added over 15 minutes at 20° C. to 25° C. The solution was heated to 53° C. overnight to full conversion. After cooling the mixture to 23° C., the pH was adjusted to 5.5 to 6 with 6N HCl, the layers separated, and the aqueous layer extracted with 2 vol of 2-MeTHF. The combined organic layers were washed twice with 3.6 vol of pH 6 potassium phosphate buffer. The organic solution was concentrated by vacuum distillation at 40° C. to 4 vol (16 L). Heptane (8 vol, 33 L) was added and the slurry cooled to 20° C. over 5 h and held overnight. The solids were collected by suction filtration and the reactor and cake dried on the filter overnight to give 2068 g (93% yield; 0 ppm residual TsOH; 99.6% AUC, RRT 1.17-0.36% AUC, RRT 0.74-<0.05% AUC) of crude Hydrate 1 of Compound (1).

Example 2B: Synthesis of Hydrate 1 of Compound (1) (Hemi-Hydrate)

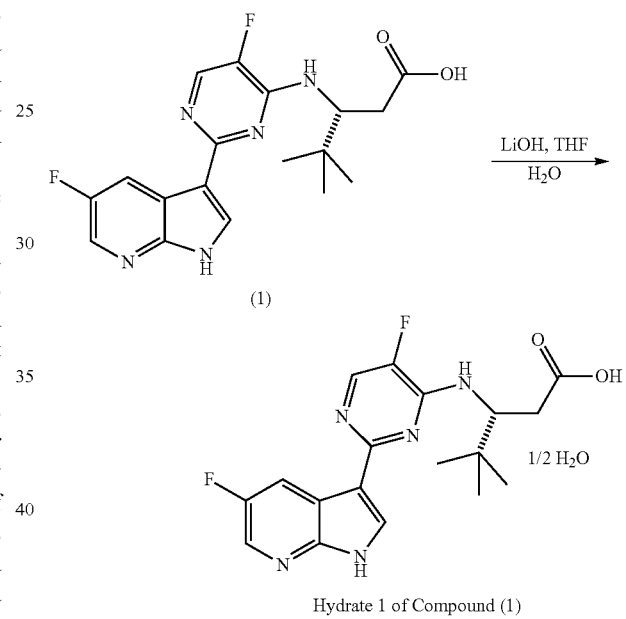

Hydrate 1 of Compound (1)

Hydrate 1 of Compound (1) was prepared by dissolving methyl (3S)-3-[[5-fluoro-2-(5-fluoro-1H-pyrrolo[2,3-b]pyridin-3yl)pyrimidin-4-yl]amino]-4,4-dimethyl-pentanoate in tetrahydrofuran (THF), followed by the addition of lithium hydroxide. The reaction was allowed to stir at room temperature followed by the addition of water. The THF was then removed under vacuum and the resulting aqueous later washed with hexanes and ether. The pH of the aqueous layer was adjusted to 7-8 followed by an extraction with ethyl acetate. The ethyl acetate is then removed under vacuum to form white crystalline solids of Hydrate 1 of Compound (1).

Example 2C: Synthesis of Hydrate 1 of Compound (1) (Hemi-Hydrate)

Amorphous Compound (1) or a THF solvate thereof was suspended in THF at room temperature. Water was slowly added while heating to a mild reflux to give a cloudy solution. The solution was then cooled to room temperature. More water was slowly added to facilitate precipitation. The suspension was stirred for ~4 hours and filtered to give a white powdery solid, which was dried in a vacuum oven at 50° C.-55° C.

TABLE 12

Reaction conditions for preparing Hydrate 1 of Compound (1).

| Comp (1) (g) | Starting Form | Solvent | Solvent Vol (mL) | Water Vol (mL) | Reaction Temp (° C.) | Water (wt %) |
|---|---|---|---|---|---|---|
| 169.9 | Amorphous | THF | 848 | 678.4 | Mild Reflux and RT | 44.4 |

Figure 24:
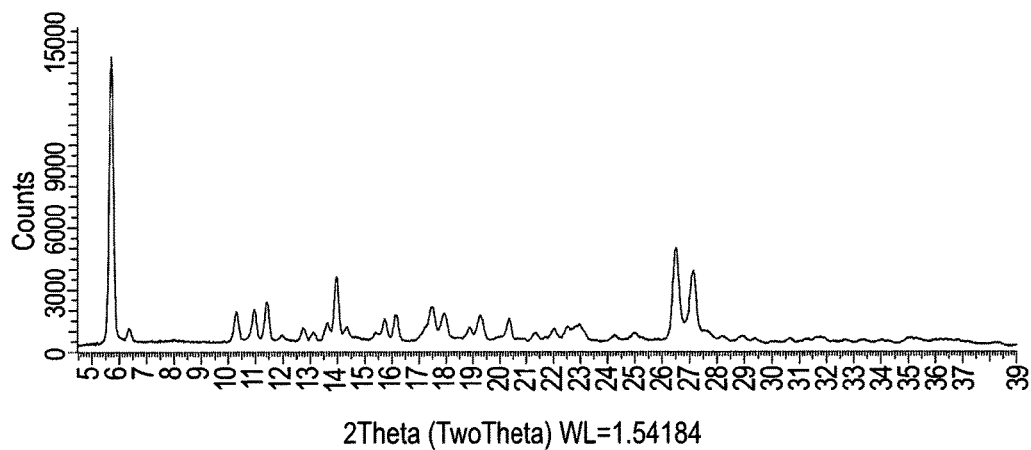
FIG. 24 is an X-ray powder diffraction pattern (XRPD) for Hydrate 1 of Compound (1).

Referring to FIG. 24, Hydrate 1 of Compound (1) was characterized using XRPD analysis according to the procedures described in Example 1, above.

Example 2D: Solubility of Hydrate 1 of Compound (1)

A pH solubility profile was determined by slurring Hydrate 1 of Compound (1) in 0.9% NaCl solutions with pH adjusted to desired levels with HCl or NaOH solutions. The slurries were allowed to equilibrate for two weeks and analyzed by HPLC and XRPD for solubility and form changes respectively. The pH solubility data generated are summarized in Table 13 and FIG. 25.

TABLE 13 pH solubility profile of Hydrate 1 of Compound (1).

| pH | Experimental Solubility (mg/mL) | USP Definition | Final Form |
|---|---|---|---|
| 0.84 | 2.146 | Slightly Soluble | — |
| 1.59 | 1.153 | Slightly Soluble | — |
| 2.84 | 0.057 | Practically Insoluble | Hydrate 3 |
| 4.22 | 0.004 | Practically Insoluble | Hydrate 3 |
| 5.17 | 0.021 | Practically Insoluble | Hydrate 3 |
| 5.96 | 0.078 | Practically Insoluble | Hydrate 3 |
| 6.38 | 0.216 | Very Slightly Soluble | Hydrate 3 |
| 6.71 | 0.420 | Very Slightly Soluble | Hydrate 3 |
| 7.07 | 0.335 | Very Slightly Soluble | Hydrate 3 |
| 7.73 | 2.235 | Slightly Soluble | Hydrate 3 |
| 8.13 | 4.831 | Slightly Soluble | Hydrate 3 |
| 8.40 | 4.355 | Slightly Soluble | Hydrate 3 |

Figure 25:
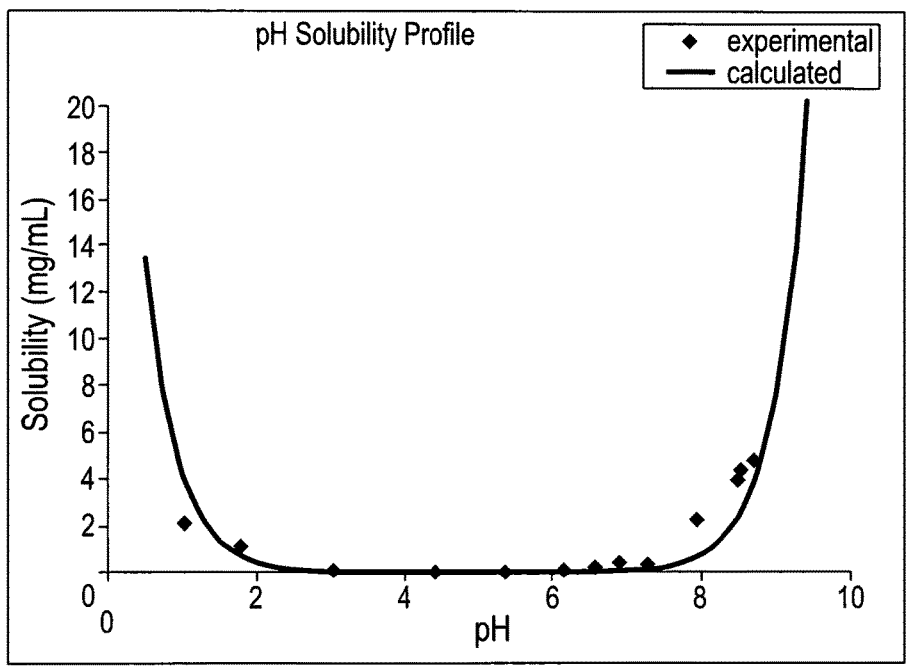
FIG. 25 is a plot of solubility vs. pH for Hydrate 1 of Compound (1).

Referring to FIG. 25, the solubility curve closely follows the predicted pH solubility profile, with a U-shaped or bell-shaped curve indicating very low solubility (the compound is practically insoluble) between pH 2.0 and 7.0. Solubility increases significantly below pH 2.0 and above pH 7.0.

Hydrate 1 of Compound (1) was also suspended in a variety of aqueous solutions and allowed to slurry for five days. Solubility and form changes were observed by HPLC and XRPD, respectively. As observed in the pH solubility profile, solubility was found to be significantly higher when suspended in aqueous solutions at low or high pH values. Solutions with pH values between 3 and 6 showed significantly lower solubility. The solubility assessment also showed that the presence of surfactants and solubilizing agents such as Cremophor, Tween 80 and Vit E TPGS significantly improved the solubility of Hydrate 1 of Compound (1). It should be noted that the 5-day solubility analysis resulted in the formation of Hydrate 2 of Compound (1) in a significant number of the samples. Solubility in organic solvents are summarized in Table 14.

TABLE 14

Five day solubility of Compound (1) in aqueous systems starting with Hydrate 1 of Compound (1).

| Aqueous media | Solubility (mg/mL) | pH | USP Definition | Final Form |
|---|---|---|---|---|
| 5% Dextrose in Water | 0.094 | 4.84 | Practically Insoluble | Hydrate 2 |
| 0.9% Sodium Chloride | 0.108 | 4.18 | Very Slightly Soluble | Hydrates 2 + 3 |
| 5% PG | 0.512 | 5.04 | Very Slightly Soluble | Hydrates 2 + 3 |
| 10% PG | 0.110 | 5.39 | Very Slightly Soluble | Hydrates 2 + 3 |
| 5% PEG300 | 0.135 | 3.96 | Very Slightly Soluble | Hydrate 2 |
| 10% PEG300 | 0.285 | 3.56 | Very Slightly Soluble | Hydrate 2 |
| 5% PEG400 | 0.223 | 5.53 | Very Slightly Soluble | Hydrate 2 |
| 10% PEG400 | 0.089 | 4.79 | Practically Insoluble | Hydrates 2 + 3 |
| 10% Ethanol | 0.289 | 5.74 | Very Slightly Soluble | Hydrate 2 |
| 20% Ethanol | 0.467 | 6.04 | Very Slightly Soluble | Hydrate 2 |
| 5% Glycerin | 0.152 | 5.59 | Very Slightly Soluble | Hydrates 2 + 3 |
| 25% Glycerin | 0.108 | 4.93 | Very Slightly Soluble | Hydrates 2 + 3 |
| 3% DMA | 0.098 | 5.03 | Practically Insoluble | Hydrates 2 + 3 |
| 0.5% Tween 80 | 1.174 | 5.83 | Slightly Soluble | Hydrate 2 |
| 5% Cremorphor EL | 1.152 | 4.15 | Slightly Soluble | Hydrate 2 |
| 10% Cremorphor EL | 1.635 | 4.17 | Slightly Soluble | Hydrate 2 |
| 2% Mannitol | 0.228 | 5.58 | Very Slightly Soluble | Hydrate 2 |
| 10% Captisol | 0.354 | 5.13 | Very Slightly Soluble | Hydrate 2 |
| 20% Captisol | 0.606 | 5.08 | Very Slightly Soluble | Hydrate 2 + 3 |
| 10% Cavitron | 0.343 | 4.49 | Very Slightly Soluble | Hydrate 2 + 3 |
| 20% Cavitron | 1.022 | 5.78 | Slightly Soluble | Hydrate 2 + 3 |
| 0.05% VIT E TPGS | 0.272 | 5.97 | Very Slightly Soluble | Hydrate 2 |
| 5% Pluronic F68 | 0.116 | 4.49 | Very Slightly Soluble | Hydrate 2 |
| pH 7.0, 50 mM Sodium Phosphate buffer | 0.979 | 6.63 | Very Slightly Soluble | Hydrate 2 |
| pH 8.0, 50 mM Sodium Phosphate buffer | 7.623 | 7.42 | Slightly Soluble | Hydrate 2 + 3 |
| pH 7.0, 50 mM Potassium Phosphate buffer | 0.945 | 6.61 | Very Slightly Soluble | Hydrate 2 + 3 |
| pH 8.0, 50 mM Potassium Phosphate buffer | 6.620 | 7.46 | Slightly Soluble | Hydrate 2 |
| FaSSGF | 2.660 | 1.55 | Slightly Soluble | Hydrate 2 |
| FaSSIF | 0.080 | 6.47 | Practically Insoluble | Hydrate 3 |
| FeSSIF | 0.060 | 5.11 | Practically Insoluble | Hydrate 2 |
| 1% Tween 80 | 0.360 | 6.70 | Very Slightly Soluble | Hydrate 2 + 3 |
| 10% Vit E TPGS | 1.620 | 5.22 | Slightly Soluble | Hydrate 2 |
| 30% PEG400 | 0.200 | 6.19 | Very Slightly Soluble | Hydrate 3 |
| 30% PG | 0.170 | 6.18 | Very Slightly Soluble | Hydrate 2 + 3 |
| 0.5% MC | 0.120 | 6.17 | Very Slightly Soluble | Hydrate 2 + 3 |

Example 3: Preparation of Hydrate 2 of Compound (1) (Monohydrate)

Hydrate 2 was prepared by adding amorphous or solvated Compound (1) to a mixture of water and an organic solvent (s), where in the mixture of the water and organic solvent(s) has a specific water activity of 0.2 to 0.9, depending on the organic solvent used. The mixture was stirred at room temperature or heated at ≤40° C. until conversion to the Hydrate 2.

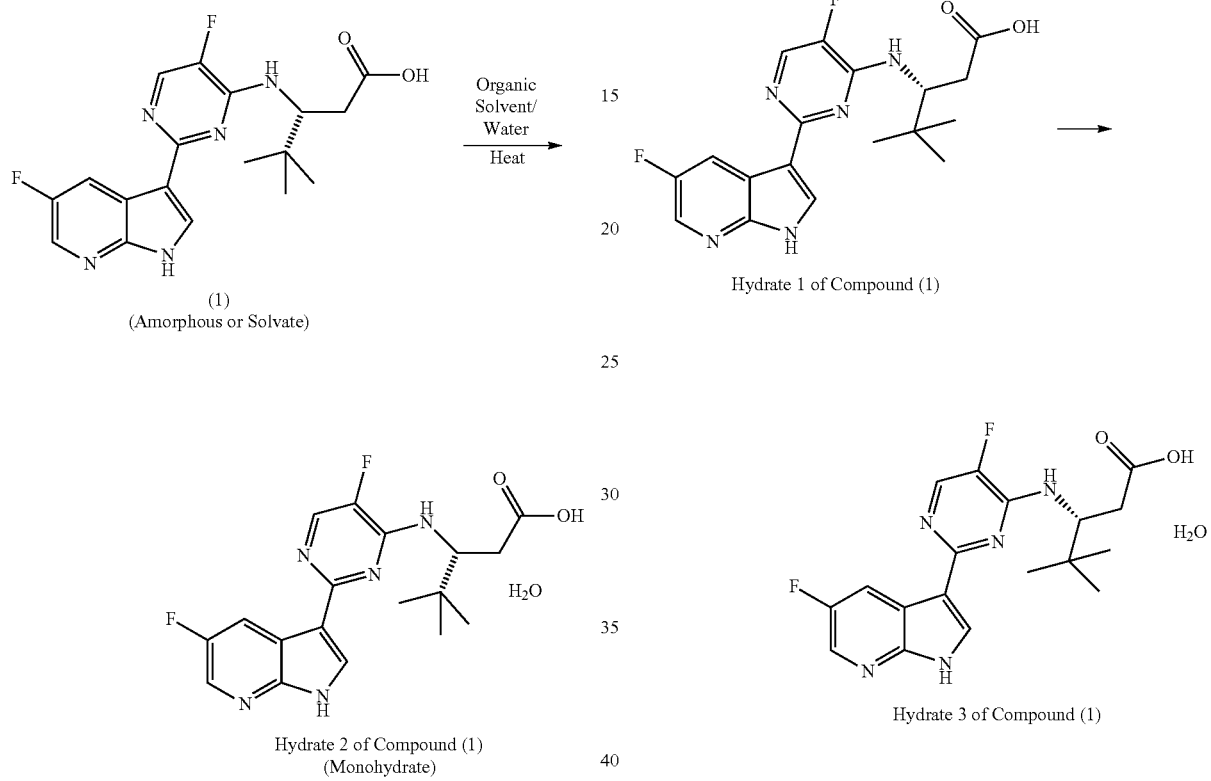

Referring to FIGS. 1-4, Hydrate 2 of Compound (1) was characterized using XRPD, $^{13}$C SSNMR, DSC, and TGA analyses according to the procedures described in Example 1, above.

A single crystal of Hydrate 2 of Compound (1) was grown at room temperature by slow evaporation of a 50 mg/ml solution of Compound (1) in 1:1 acetone/water. Crystallography data were collected with Cu Kα radiation at 100° K on a Bruker APEX II CCD diffractometer.

Hydrate 2 of Compound (1) crystal showed monoclinic unit cells with C2 space group and unit cell dimensions of a=25.0468(10) Å, b=6.6682(3) Å, c=11.0710(5) Å, α=90°. β=92.368(3)°. γ=90°. Volume=1847.47(14) Å3. In Hydrate 2 of Compound (1), there is one Compound (1) molecule and one water molecule in the asymmetric unit, showing fully ordered molecules with the water molecule fully occupied. The structure has high quality with no ambiguity with an R factor of 2.32%. Hydrate 2 of Compound (1) is a zwitterion, confirmed by the C—O distances in the carboxylate group.

Figure 3:
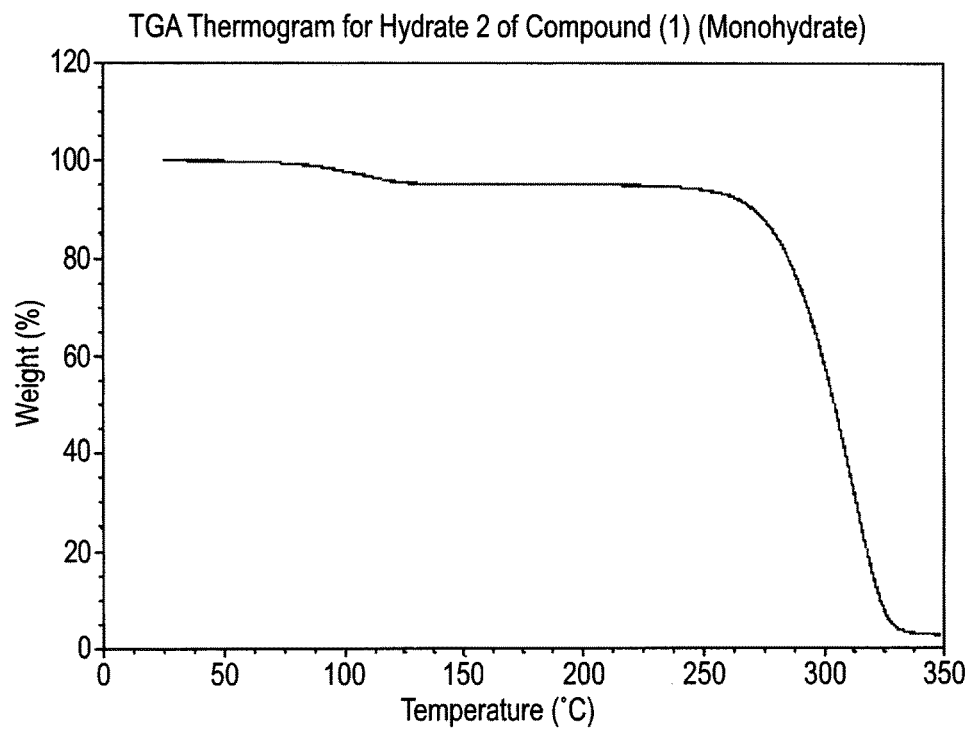
FIG. 3 is a TGA thermogram of Hydrate 2 of Compound (1).

Referring to FIG. 3, the TGA thermogram demonstrates a weight loss of 4.6% when heated to 122° C. with an onset of 75° C. to 80° C. The weight loss is consistent with theoretical monohydrate (4.6%).

Figure 4:
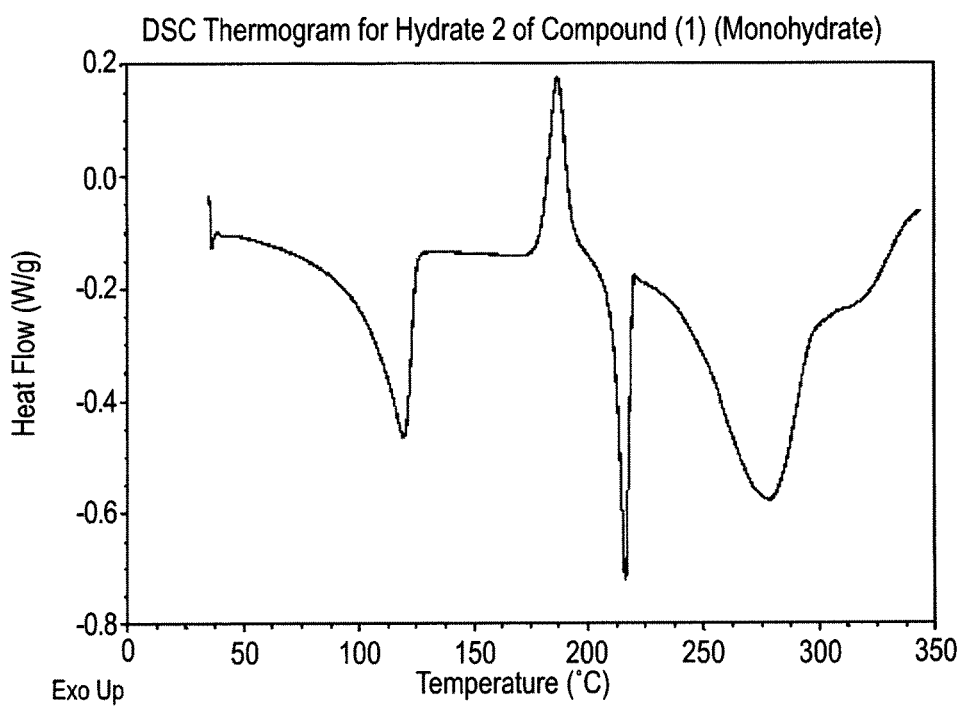
FIG. 4 is a DSC thermogram of Hydrate 2 of Compound (1).

Referring to FIG. 4, the DSC thermogram reveals a dehydration onset temperature of 50° C. to 60.5° C. The dehydration results in the formation of amorphous free form Compound (1) and recrystallizes with an onset of 175° C. to 180° C. to anhydrous free Form A of Compound (1), followed immediately by melting/decomposition with an onset of 211° C.

Example 4A: Preparation of Hydrate 3 of Compound (1) (Monohydrate)

A 90 L reactor was charged sequentially with Hydrate 1 of Compound (1) (2011 g), acetone (10 vol) and water (3 vol) and the slurry heated to 50° C. The homogeneous solution was passed through a 0.22 µm in line filter into a 60 L reactor and cooled to 42° C. To this solution was added 0.5 wt % of jet milled seed (Hydrate 3 of Compound (1)). A slurry of Hydrate 3 of Compound (1) immediately formed as confirmed by XRPD analysis. Water (9 vol) was added over a period of 4 hours. After the slurry was confirmed to be only Hydrate 3 of Compound (1), the batch was cooled to 5.6° C. over 10 hours and held overnight. A sample of the slurry was shown to be >95% Hydrate 3 of Compound (1) by XRPD analysis and the solids collected by suction filtration. The reactor was rinsed with 2 volumes of 4:1 water:acetone and drained to the filter cake. The cake was dried on the funnel by vacuum for 3 h and then covered, without vacuum for 2 days (over weekend). The material was dried at 40° C. under a 20-25 in Hg vacuum with a N$_2$ sweep for 24 hours to give 1810 g (85%) of Hydrate 3 of Compound (1) (monohydrate) in 77% overall yield.

In Examples 4B-4I, Hydrate 3 of Compound (1) was prepared by adding the amorphous Compound (1) or Hydrate 1 of Compound (1) to a mixture of water and an organic solvent, wherein the mixture of the water and organic solvent(s) has a specified water activity from 2.5 to 0.90 depending on the organic solvent used, as provided in Table 15, below:

TABLE 15

Reaction conditions for preparing Hydrate 3 of Compound (1).

| Example No. | Amount of Cmpd (1) (g) | Starting Form | Solvent | Solvent Vol. (mL) | Water Vol. (mL) | Reaction Temp. (° C.) | Water (wt %) |
|---|---|---|---|---|---|---|---|
| 4B | 18.05 | Hydrate 1 | Acetonitrile | 150 | 50 | RT | 25 |
| 4C | 1.02 | Hydrate 1 | — | — | 10 | RT | 100% |
| 4D | 0.50 | Hydrate 1 | — | — | 5 | RT | 100% |
| 4E | 0.50 | Hydrate 1 | — | — | 10 | RT | 100% |
| 4F | 230 | Hydrate 1 | Acetonitrile | 1696 | 1696 | RT | 50% |
| 4G | 0.01 | Hydrate 1 | IPAC | 0.497 | 0.003 | RT | 0.6% |
| 4H | 2.05 | Amorphous | Acetonitrile | 10 | 1 | 40° C. | 9.09% |
| 4I | 2.50 | Amorphous | Acetonitrile | 10 | 2 | RT | 16.67% |

Referring to FIGS. 5-8, Hydrate 3 of Compound (1) was characterized using XRPD, $^{13}$C SSNMR, TGA, and DSC analyses according to the procedures described in Example 1, above.

Figure 7:
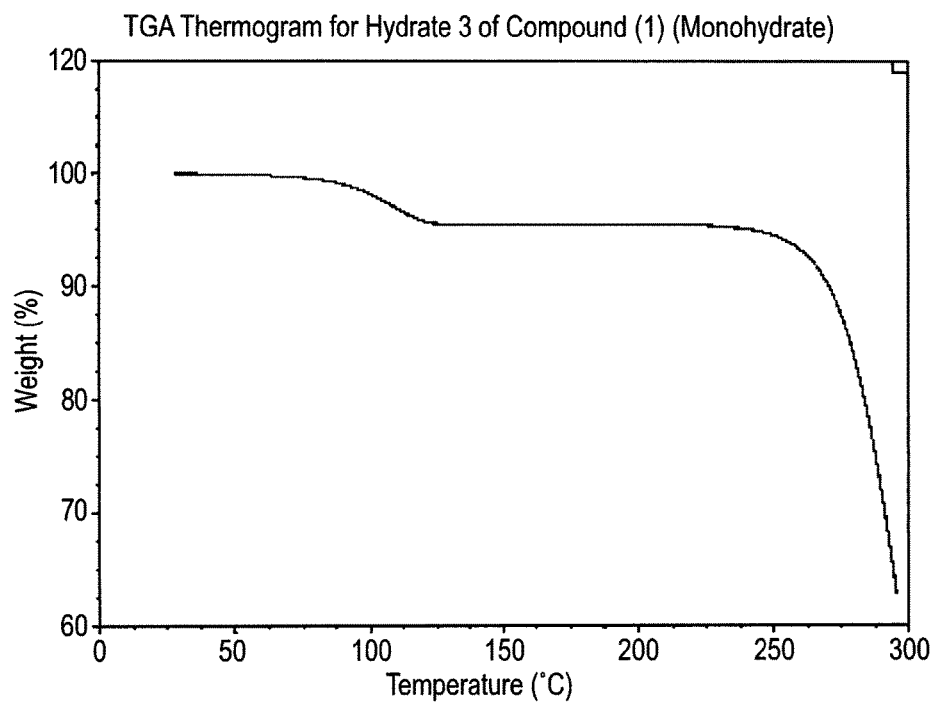
FIG. 7 is a TGA thermogram of Hydrate 3 of Compound (1).

Referring to FIG. 7, the TGA thermogram indicated a weight loss of 5.2% when heated to 115° C. with an onset of 80° C. to 85° C. This weight loss is consistent with the theoretical mono-hydrate (4.58%).

Figure 8:
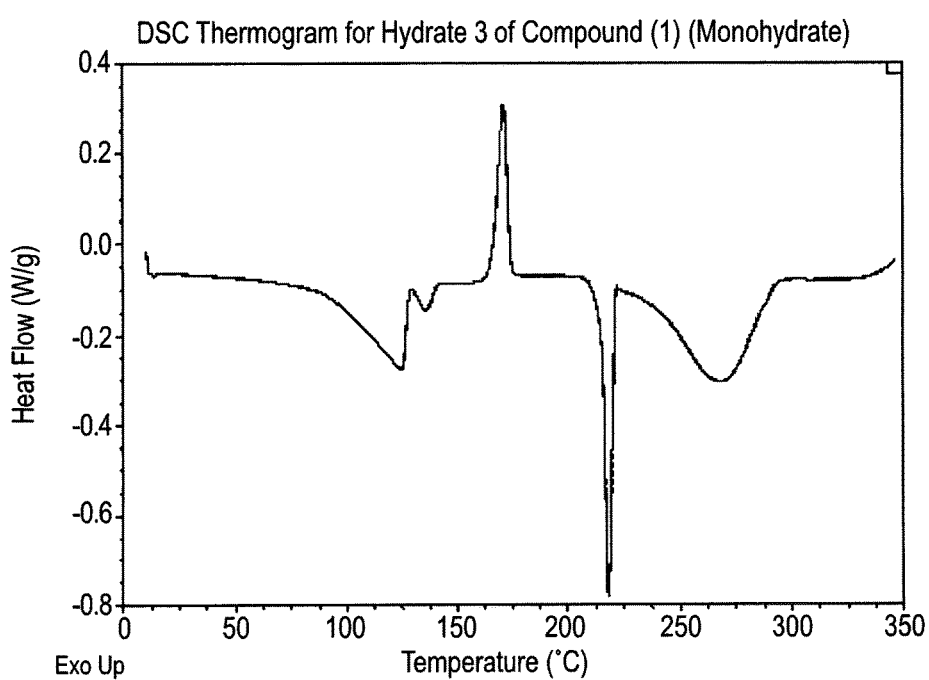
FIG. 8 is a DSC thermogram of Hydrate 3 of Compound (1).

Referring to FIG. 8, the DSC thermogram indicates a loss of moisture with an onset temperature of 75° C. to 80° C. resulting in the formation of anhydrous free Form B, which converts to an amorphous material at an onset temperature of 125° C. followed by decomposition at 240° C.

A single crystal of Hydrate 3 of Compound (1) was also grown at room temperature by slow evaporation of a 50 mg solution of Compound (1) in 1:1 methyl ethyl ketone/water. The crystallographic data were also collected with Cu Kα radiation at 100K on the Bruker APEX II CCD diffractometer. Hydrate 3 of Compound (1) showed an orthorhombic unit cell with P212121 space group and unit cell dimensions a=6.6822(18) Å, b=10.981(3) Å, c=25.394(7) Å, α=90°. β=90°. γ=90°. Volume=1863.3(9) Å3. Similar to Hydrate 2, there is one Compound (1) molecule and one water molecule in the asymmetric unit. The structures are also fully ordered with the water molecule fully occupied. The structure has high quality with no ambiguity with an R factor of 2.41%. Hydrate 3 of Compound (1) structure also confirmed by C—O distances in the carboxylate group as a zwitterion.

Example 4J: Solid State Stability of Hydrate 3 of Compound (1)

A 6-month solid-state (open dish) stability study was performed for Hydrate 3 of Compound (1). Hydrate 3 of Compound (1) was stored for 6 months under the following conditions: 40° C./75% RH, 5° C./60% RH, 25° C./60% RH, and 40° C./dry. No changes were observed by DSC analysis (dehydration and melting/decomposition events). The samples remained crystalline according to XRPD analysis and there were no changes in appearance. Thus, no significant chemical changes to Hydrate 3 of Compound (1) were observed when stored under these study conditions.

Example 4K: pH Solution Stability of Hydrate 3 of Compound (1)

Hydrate 3 of Compound (1) was evaluated in a 50% acetonitrile 50% aqueous (0.1M pH modifier at >0.1 M ionic strength) solution at 0.15 mg/ml. Hydrate 3 of Compound (1) was observed to be chemically stable over a pH range of 3 to 9 for 5 days under ambient conditions. Hydrate 3 of Compound (1) in suspension was observed to be chemically stable over a pH range of 4 to 9 at 2 mg/ml at 40° C. for 5 days (a change of 0.05% area was observed at pH 3 with no new impurities).

Example 4L: In Vitro Dilution in Simulated Fluids

Figure 26:
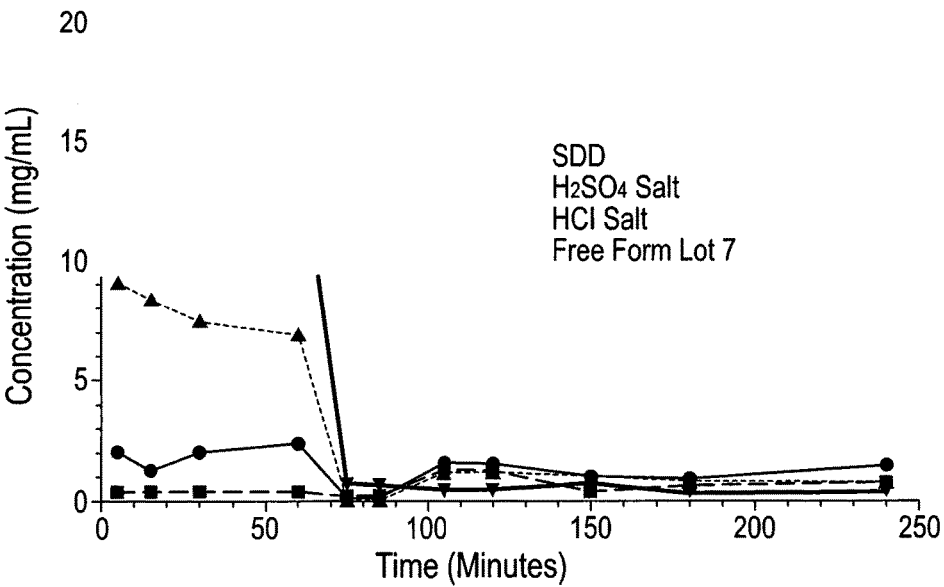
FIG. 26 is a plot of concentration vs. time for two-stage in vitro dissolution of Compound (1) forms in simulated fluids.

The in vitro dissolution profile of a suspension of Hydrate 3 of Compound (1) in 0.5% MC was compared to the corresponding $H_2SO_4$ salt and the spray-dried dispersion (SDD) in 0.5% MC suspensions. For the HCl salt, a 30% PEG300/0.5% MC vehicle was used to prepare the suspension. HCl salt of Form A was physically unstable in the 0.5% vehicle resulting in the formation of a gelatinous material. As shown in FIG. 26 and Table 16 below, in FaSSGF the HCl salt of Form A shows an 8 fold increase in concentrations whereas the SDD shows a 3 to 4 fold increase in concentrations compared to Hydrate 3 of Compound (1). The $H_2SO_4$ salt of Compound (1) showed 10 fold lower concentration levels compared to Hydrate 3 of Compound (1). The HCl salt (starting with anhydrous Form A), converted to an amorphous material in FaSSGF; Hydrate 3 of Compound (1), the $H_2SO_4$ salt, and the SDD remained physically stable in FaSSGF. In FaSSIF, all four forms showed concentration levels that were not significantly different from each other. Hydrate 3 of Compound (1), remained physically stable throughout the in vitro dissolution study. However, the HCl salt, $H_2SO_4$ salt and the SDD where physically unstable and readily converted to Hydrate 2 of Compound (1) in FaSSIF at pH ~6.4.

TABLE 16

Two-Stage In Vitro Dissolution of Hydrate 3 of Compound (1), HCl Salt, $H_2SO_4$ Salt, and Spray Dried Dispersion (SDD).

| Simulated Fluid | Time (Min) | FF Lot 7 | Final Form | HCl Salt | Final Form | $H_2SO_4$ Salt | Final Form | SDD | Final Form |
|---|---|---|---|---|---|---|---|---|---|
| SGF (pH ~1.5) | 5 | 2.053 | H3 | 14.664 | Amorphous | 0.407 | $H_2SO_4$ Form A | 9.021 | Amorphous |
| SGF (pH ~1.5) | 15 | 1.278 | H3 | 16.565 | Amorphous | 0.407 | $H_2SO_4$ Form A | 8.331 | Amorphous |

TABLE 16-continued

Two-Stage In Vitro Dissolution of Hydrate 3 of Compound (1), HCl Salt, $H_2SO_4$ Salt, and Spray Dried Dispersion (SDD).

| Simulated Fluid | Time (Min) | FF Lot 7 | Final Form | HCl Salt | Final Form | $H_2SO_4$ Salt | Final Form | SDD | Final Form |
|---|---|---|---|---|---|---|---|---|---|
| SGF (pH --1.5) | 30 | 2.031 | H3 | 14.808 | Amorphous | 0.417 | $H_2SO_4$ Form A | 7.392 | Amorphous |
| SGF (pH --1.5) | 60 | 2.40 | H3 | 15.135 | Amorphous | 0.399 | $H_2SO_4$ Form A | 6.862 | Amorphous |
| SIF (no pH Adjustment) | 75 | 0.163 | H3 | 0.747 | H2 | 0.242 | H2 | 0.048 | H2 |
| SIF (no pH Adjustment) | 90 | 0.148 | H3 | 0.964 | H2 | 0.236 | H2 | 0.059 | H2 |
| SIF (pH --6.4) | 105 | 1.588 | H3 | 0.474 | H2 | 1.373 | H2 | 1.184 | H2 |
| SIF (pH --6.4) | 120 | 1.534 | H3 | 0.477 | H2 | 1.284 | H2 | 1.182 | H2 |
| SIF (pH --6.4) | 150 | 1.058 | H3 | 0.749 | H2 | 0.396 | H2 | 1.040 | H2 |
| SIF (pH --6.4) | 180 | 0.971 | H3 | 0.340 | H2 | 0.652 | H2 | 0.827 | H2 |
| SIF (pH --6.4) | 240 | 1.497 | H3 | 0.395 | H2 | 0.789 | H2 | 0.803 | H2 |

H2—Hydrate 2 of Compound (1)
H3—Hydrate 3 of Compound (1)
FF—Hydrate 1 of Compound (1)

Example 4M: Intrinsic Dissolution Rate Determination

Figure 27:
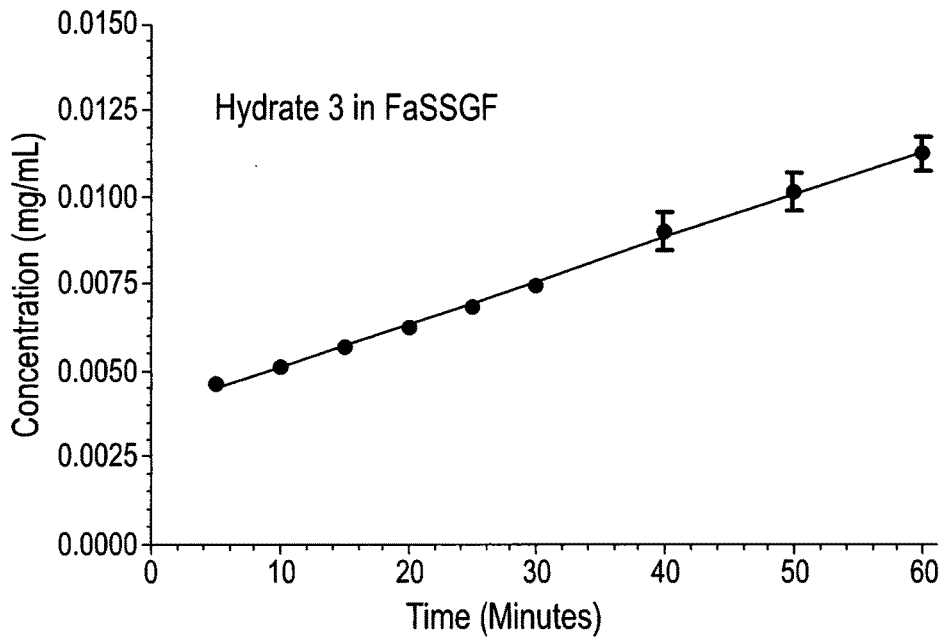
FIG. 27 is a plot of concentration vs. time for the in vitro dissolution of Hydrate 3 of Compound (1) IDR compact (surface area=0.5 cm$^2$) in simulated gastric fluid and intestinal fluids.

The intrinsic dissolution rate (IDR) of Hydrate 3 of Compound (1) was determined using the woods apparatus to press compacts that were suspended in FaSSGF and FaSSIF in a USP dissolution bath. HPLC was used to analyze the concentration at selected time points up to one hour. Referring to FIG. 27, the IDR for Hydrate 3 of Compound (1) was determined to be 0.020 mg/min/cm$^2$ in FaSSGF and 0.012 mg/min/cm$^2$ in FaSSIF, respectively. The IDR values were used to determine the dissolution rate factor (z-factor) to be 1.73×10-3 mL/mg/min assuming a solubility of 2.66 mg/mL in FaSSGF. A z-factor of 5.51×10-3 mL/mg/min was determined for Hydrate 3 of Compound (1) assuming a solubility of 0.08 mg/ml in FaSSIF.

Example 4N: Processing Properties of Hydrate 3 of Compound (1)

Figure 31:
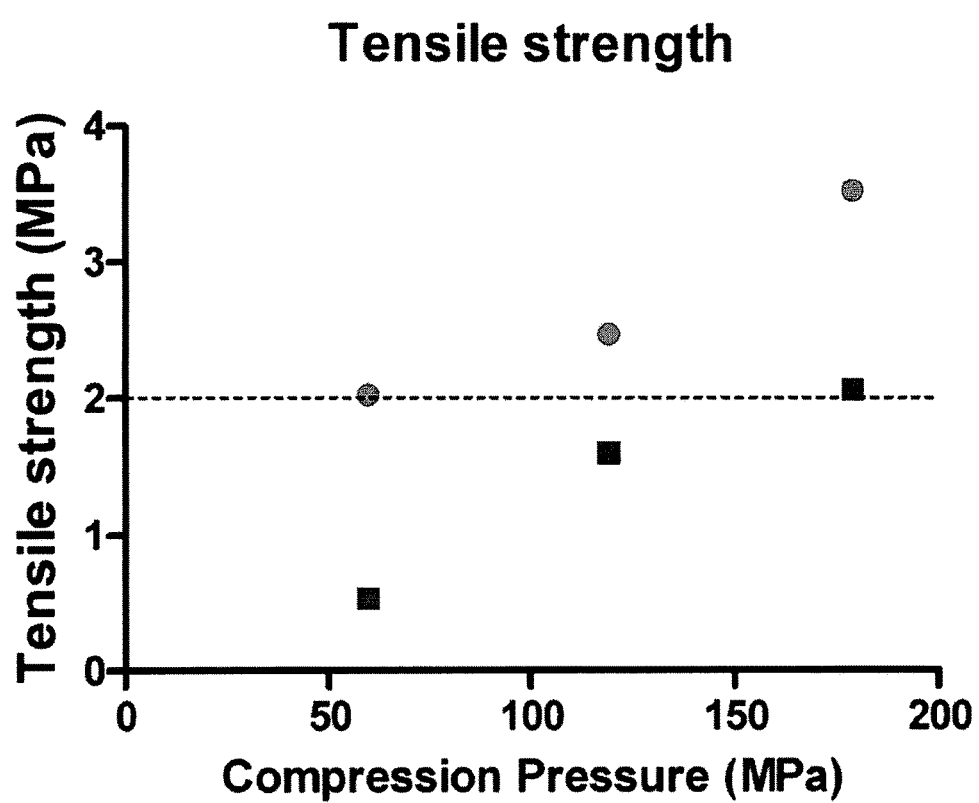
FIG. 31 is a plot of tensile strength vs. compression pressure for Hydrate 3 of Compound (1).

Hydrate 3 of Compound (1) was assessed for compressibility, sticking, flow, and bulk density. Hydrate 3 of Compound (1) showed a bulk density of 0.172 g/cc and a tap density of 0.383 g/cc. Hydrate 3 of Compound (1) is classified as good flow by Ring Shear Testing (RST), with an average flow factor (FFc) of 6.8 (good flow is anywhere from 4-10), and adequate compressibility, see FIG. 31. An increase in tensile strength is observed with an increase in compression, reaching a target tensile strength of 2 MPa at 180 MPa compression pressure. Delamination was observed at a very high compression pressure of 500 MPa. Good compression and tensile strength suggest that the drug substance is amenable to direct compression for the development of solid dosage forms.

Example 5: Preparation of Form D of Compound (1) (Anhydrous)

Hydrate 1 of Compound (1) was suspended in isopropyl acetate room temperature. The sample was stirred for 24 hours to form the anhydrous Form D of Compound (1). The suspension was then filtered and dried under vacuum at 70° C. for approximately 10 hours to give a white powder.

TABLE 17

Reaction conditions for preparing Form D of Compound (1).

| Compound (1) (g) | Starting Form | Solvent | Solvent Vol. (mL) | Reaction Temp. (° C.) |
|---|---|---|---|---|
| 0.50 | Hydrate 1 | IPAC | 5.0 | RT |

Figure 10:
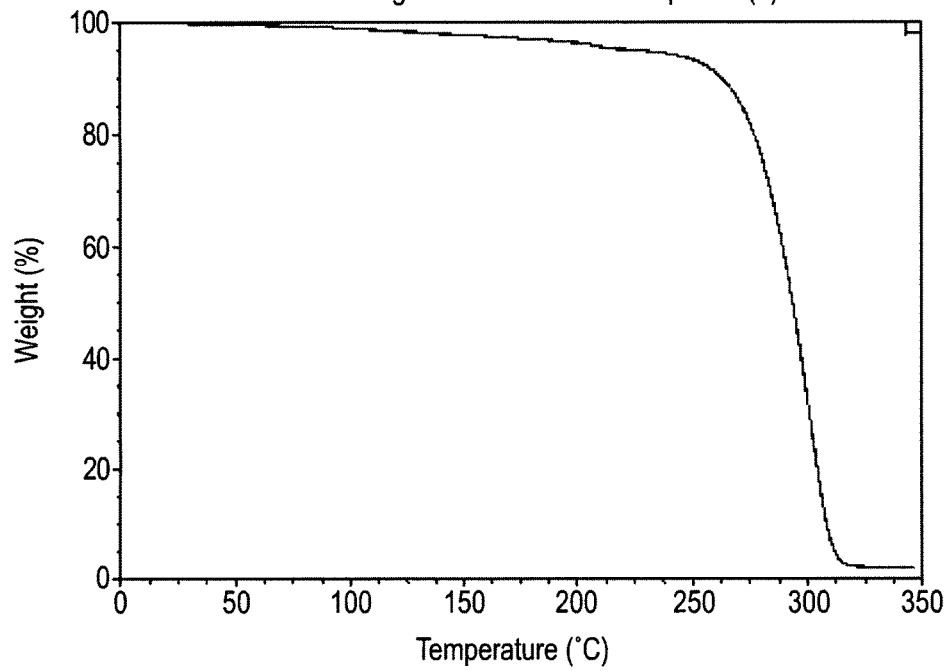
FIG. 10 is a TGA thermogram of Form D of Compound (1).
Figure 11:
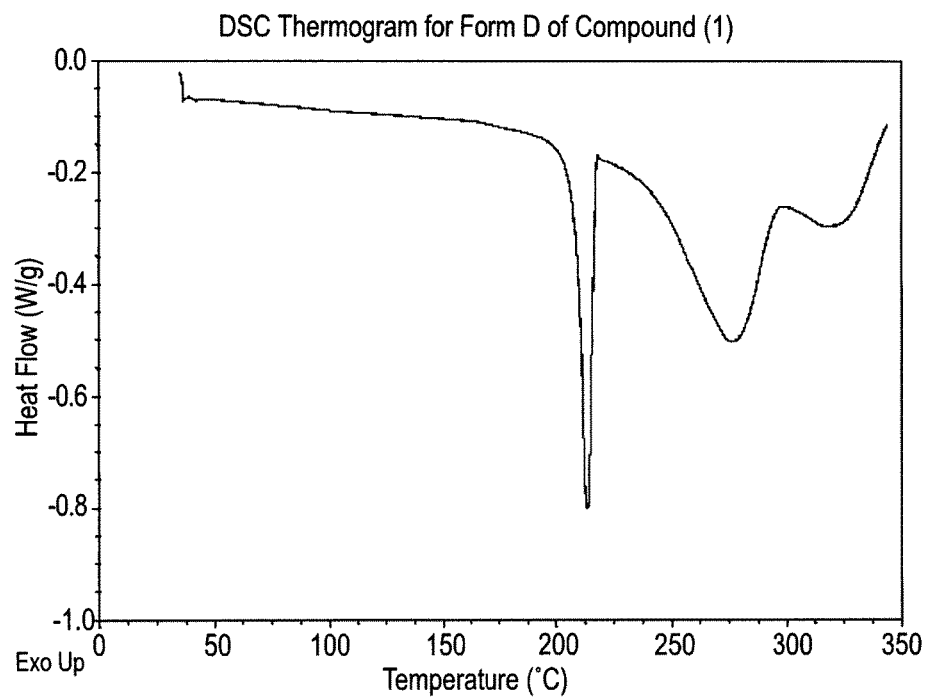
FIG. 11 is a DSC thermogram of Form D of Compound (1).

Referring to FIGS. 9-11, Form D of Compound (1) was characterized using XRPD, TGA, and DSC analyses according to the procedures described in Example 1, above.

Referring to FIG. 10, the TGA thermogram indicated a gradual weight loss of 2.0% when heated to 150° C. representing the loss of isopropyl alcohol. The weight lost was not sufficient to form a stoichiometric amount (21% loss needed for 1:1 stoichiometry), thus indicating that the weight loss is a result of the presence of residual isopropyl alcohol solvent.

Referring to FIG. 11, the DSC thermogram indicates a single melting peak with an onset of 209° C. followed by decomposition.

Example 6: Preparation of Form A of Compound (1) (Anhydrous)

Hydrates 1 and 2 of Compound (1) dehydrate to amorphous Compound (1) at 100° C., and amorphous Compound (1) crystallizes to anhydrous Form A upon further heating to 175° C. Form A of Compound (1) was prepared by dehydrating Hydrates 2 and/or 3 at 175° C., after dehydration is complete; the sample was gradually cooled to room temperature. Furthermore, Form B of Compound (1) converts to anhydrous Form A with heating to 175° C.

Figure 13:
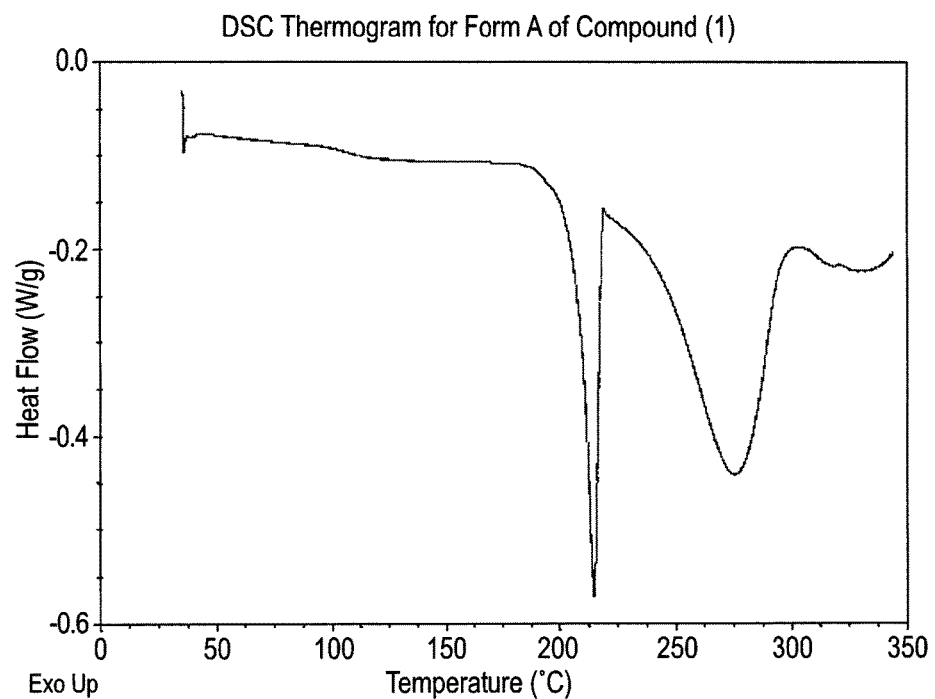
FIG. 13 is a DSC thermogram of Form A of Compound (1).

Referring to FIGS. 12 and 13, Form A of Compound (1) was characterized using XRPD and DSC analyses according to the procedures described in Example 1, above.

Referring to FIG. 13, the DSC thermogram reveals a melt with an onset of 208° C. followed by decomposition.

Example 7: Preparation of Form B of Compound (1) (Anhydrous)

Hydrate 3 of Compound (1) dehydrates at an onset temperature of 80° C., and dehydration is complete at a temperature above 110° C., wherein metastable anhydrous Form B is generated. Form B of Compound (1) was prepared by dehydrating Hydrate 3 (mono-hydrate) of Compound (1) at 100° C. to 125° C.

Referring to FIG. 14, Form B of Compound (1) was characterized using XRPD according to the procedures described in Example 1, above.

Example 8: Preparation of Form C of Compound (1) (Anhydrous)

Anhydrous Form C of Compound (1) was identified from iso-structural solvates of IPA and n-propanol heated to 175° C. Anhydrous Free Form C of Compound (1) was prepared by heating the IPA solvate of Compound (1) to ≥175° C. and slowly cooling it to room temperature.

Referring to FIG. 15, Form C of Compound (1) was characterized using XRPD analysis according to the procedures described in Example 1, above.

Example 9: Preparation of Isopropyl Alcohol Solvate of Compound (1)

The isopropyl alcohol (IPA) solvate of Compound (1) was prepared by slurring the amorphous or hydrated Compound (1) in IPA with a water activity ≤0.2 at ambient conditions.

Figure 17:
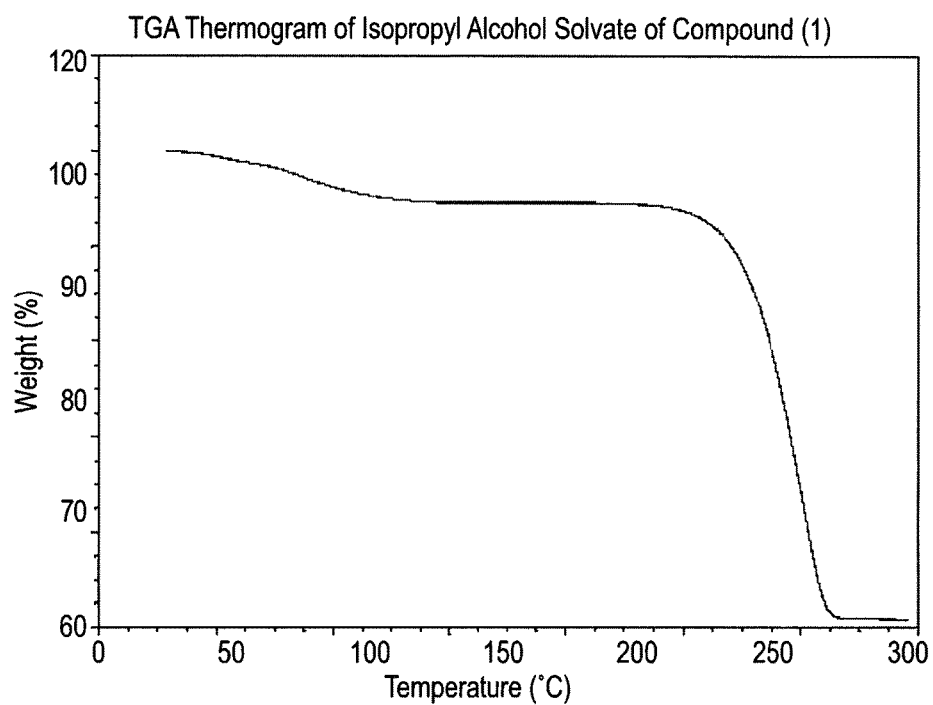
FIG. 17 is a TGA thermogram for an isopropyl alcohol solvate of Compound (1).

Referring to FIGS. 16 and 17, the isopropyl alcohol solvate of Compound (1) was characterized using XRPD and TGA analyses according to the procedures described in Example 1, above.

Referring to FIG. 17, the TGA thermogram demonstrates a weight loss of 10.5% when heated to 150° C., representing the loss of isopropyl alcohol.

Example 10: Preparation of Acetonitrile Solvate of Compound (1)

The acetonitrile solvate of Compound (1) was prepared by slurring the amorphous or hydrated Compound (1) in acetonitrile with a water activity ≤0.25 at ambient conditions.

Figure 19:
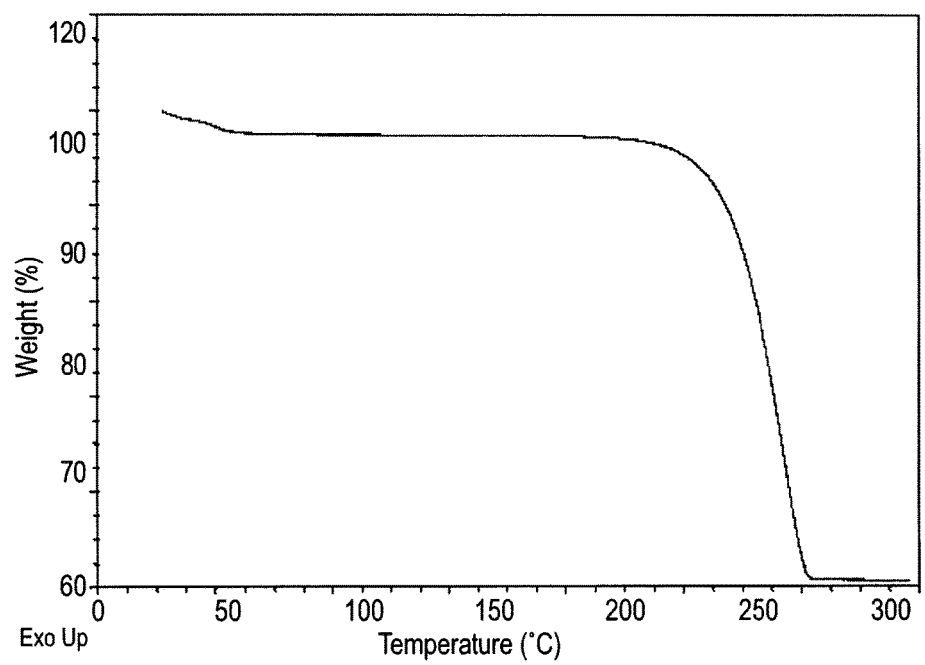
FIG. 19 is a TGA thermogram for an acetonitrile solvate of Compound (1).

Referring to FIGS. 18 and 19, the acetonitrile solvate of Compound (1) was characterized using XRPD and TGA analyses according to the procedures described in Example 1, above.

Referring to FIG. 19, the thermogram demonstrates a weight loss of 5.1% when heated to 75° C., representing the loss of acetonitrile.

Example 11: Preparation of 2-Methyl Tetrahydrofuran Solvate of Compound (1)

The 2-methyl tetrahydrofuran (2-MeTHF) solvate of Compound (1) was prepared by slurring the amorphous or hydrated Compound (1) in 2-MeTHF with a water activity ≤0.25 at ambient conditions.

Referring to FIG. 20, the 2-methyl tetrahydrofuran solvate of Compound (1) was characterized using XRPD analysis according to the procedures described in Example 1, above.

Example 12: Synthesis of Amorphous Compound (1)

Compound (1) was mixed in a solution of lithium hydroxide and water. The mixture was heated to reflux and stirred for one hour. The mixture was then cooled in an ice-bath followed by the drop wise addition of aqueous HCl until pH reaches 4.0 to precipitate the final product. Precipitated solids were then collected by filtration, washed with water and dried in a vacuum oven at elevated temperatures to give a yellow tan solid of amorphous Compound (1).

Amorphous Compound (1) may also be generated by dehydrating Hydrate 1 of Compound (1) at 100° C. and recrystallizing the heated material.

Figure 22:
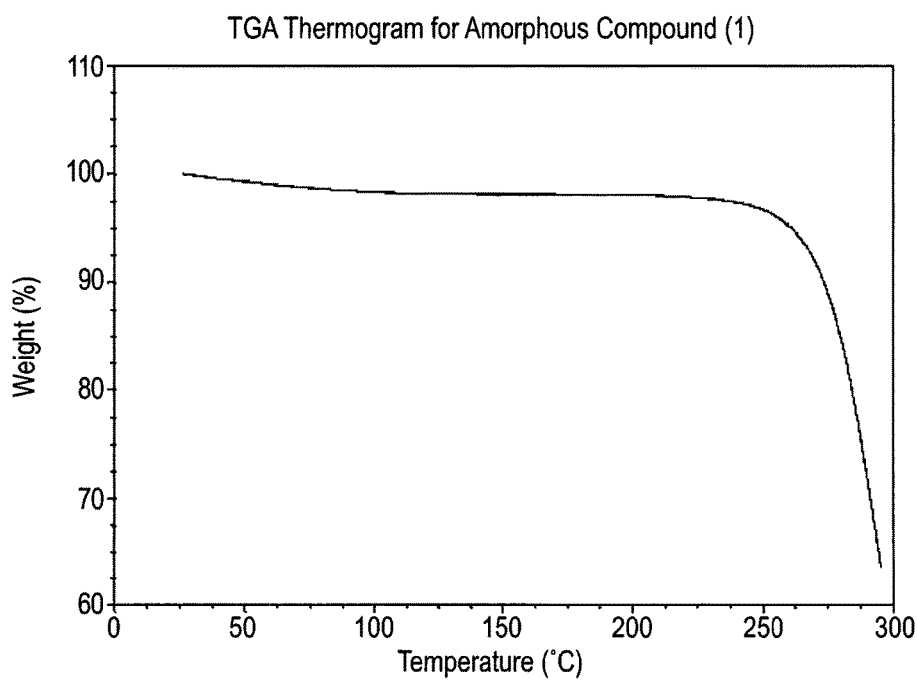
FIG. 22 is a TGA thermogram of amorphous Compound (1).
Figure 23:
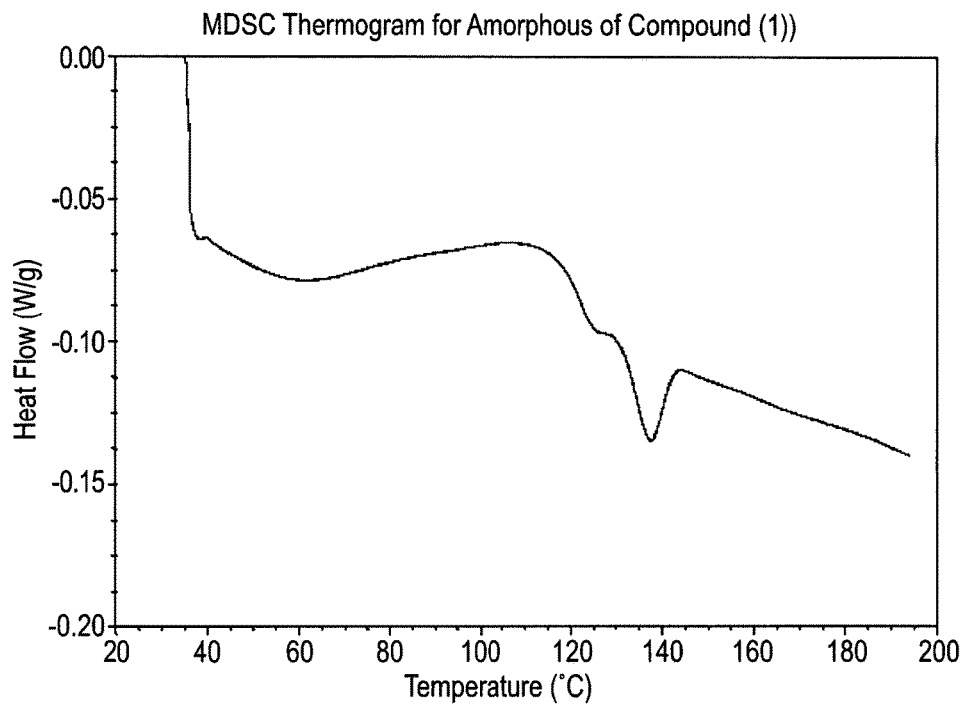
FIG. 23 is a MDSC thermogram of amorphous Compound (1).

Referring to FIGS. 21-23, amorphous Compound (1) was characterized using XRPD, TGA, and DSC analyses.

Referring to FIG. 22, the TGA thermogram demonstrates a gradual weight loss of less than 2.0% when heated to 150° C.

Referring to FIG. 22, a modulated DSC (MDSC) thermogram for amorphous Compound (1) was obtained using TA Instruments DSC Q2000. Amorphous Compound (1) was heated at 1° C./min from 25° C. to 200° C. The MDSC thermogram reveals a glass transition temperature at 120° C.

Example 13: Two Week Solubility of Compound (1)

Compound (1) was also subjected to a 2 week solubility study as summarized in Table 18.

TABLE 18

Two week solubility study of Compound (1).

| Solvent/Media | Starting Form | Final Form (After two Weeks) |
|---|---|---|
| Water | Hydrate 1 | Hydrate 2 + 3 |
| Methanol | Hydrate 1 | Solvate |
| Ethanol | Hydrate 1 | Solvate |
| Acetonitrile | Hydrate 1 | Solvate |
| Tetrahydrofuran | Hydrate 1 | Solvate |
| Acetone | Hydrate 1 | Solvate |
| Isopropyl Alcohol | Hydrate 1 | Solvate |
| Methylethyl Ketone | Hydrate 1 | Solvate |
| 2-Methyl THF | Hydrate 1 | Solvate |
| Methyl t-Butyl Ether | Hydrate 1 | Solvate |
| Ethyl Acetate | Hydrate 1 | Solvate |
| Isopropyl Acetate | Hydrate 1 | Form D |
| 1,1,2-Trichloroethane | Hydrate 3 | Hydrate 3 |
| 1,2-Dichloroethane | Hydrate 3 | Form D |
| 1,2-Dimethoxyethane | Hydrate 3 | Form D |
| 1,4-Dioxane | Hydrate 3 | Solvate |
| 1-Butanol | Hydrate 3 | Solvate |
| 1-Pentanol | Hydrate 3 | Solvate |
| 1-Propanol | Hydrate 3 | Solvate |
| 2-Butanol | Hydrate 3 | Solvate |
| 2-Methoxyethanol | Hydrate 3 | Solvate |
| 2-Methy-1-propanol | Hydrate 3 | Solvate |
| 3-Methyl-1-butanol | Hydrate 3 | Solvate |
| Anisole | Hydrate 3 | Solvate |
| Butyl acetate | Hydrate 3 | Solvate |
| Chlorobenzene | Hydrate 3 | Hydrate 3 |
| Chloroform | Hydrate 3 | Hydrate 1 |
| Cumene | Hydrate 3 | Hydrate 3 |
| Cyclohexane | Hydrate 3 | Hydrate 3 |
| Dichloromethane | Hydrate 3 | Solvate |
| Dimethyl sulfoxide | Hydrate 3 | Solvate |
| Ethyl ether | Hydrate 3 | Form D |
| Ethyl formate | Hydrate 3 | Solvate |
| Ethylene glycol | Hydrate 3 | Solvate |
| Formic acid | Hydrate 3 | Solvate |
| Heptane | Hydrate 3 | Hydrate 3 |
| Isobutyl acetate | Hydrate 3 | Form D |
| Methyl acetate | Hydrate 3 | Solvate |
| Methylbutylketone | Hydrate 3 | Form D |
| Nitromethane | Hydrate 3 | Solvate |
| Pentane | Hydrate 3 | Hydrate 3 |
| Propyl acetate | Hydrate 3 | Solvate |
| Tetralin | Hydrate 3 | Hydrate 3 |
| Toluene | Hydrate 3 | Hydrate 3 |
| Xylene | Hydrate 3 | Hydrate 3 |

Example 14: Toxicology Formulation Development

Figure 28:
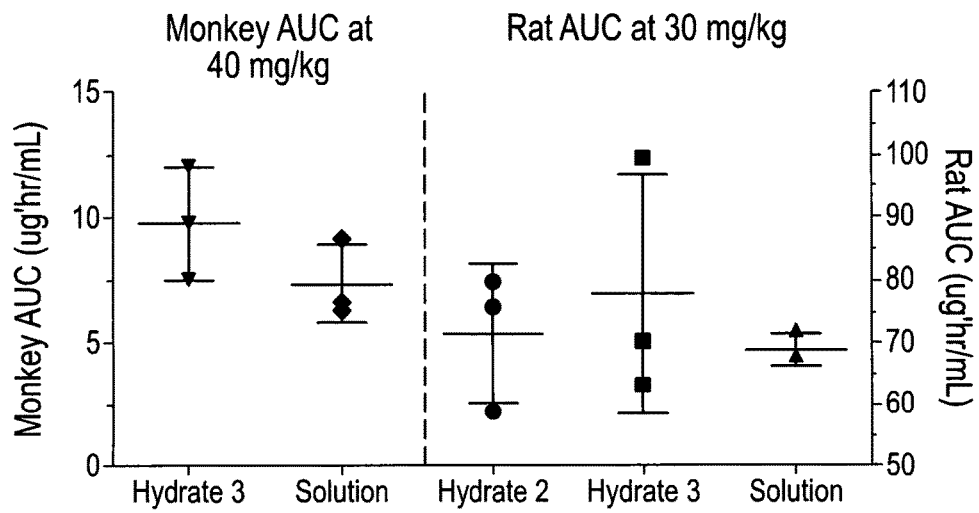
FIG. 28 is a plot of AUC for in vivo exposures of Hydrates 3 and 2 of Compound (1), compared to a solution formulation in monkeys (40 mg/kg) and rats (30 mg/kg).

A solution formulation of Compound (1) consisting of 0.5% MC with 1.5 eq NaOH (pH 8.0) was compared to suspension formulations Hydrates 2 and 3 of Compound (1) in 0.5% MC in both monkeys and rats. Referring to FIG. 28, exposures observed in both rats and monkeys were statistically comparable at 30 and 40 mg/kg, respectively.

A suspension of Hydrate 3 of Compound (1) was also compared to the suspensions of the corresponding HCl salt, $H_2SO_4$ salt, and the SDD (50% Drug Load in HPMCAS HF) in both rats and monkeys at 30 and 350 mg/kg, respectively. The monkeys and rats were dosed with formulations according to Table 19.

TABLE 19

Formulations dosed in Monkeys and Rats.

| Starting Form | Vehicle | Final Form Prior to Dosing |
|---|---|---|
| Hydrate 3 of Compound (1) | 0.5% MC | Hydrate 3 of Compound (1) |
| HCl salt Form A | 30% PEG 300/0.5% MC | HCl salt Form A |
| $H_2SO_4$ salt Form A | 0.55% MC | $H_2SO_4$ salt Form A |
| SDD | 0.5% MC | Amorphous |

Figure 29:
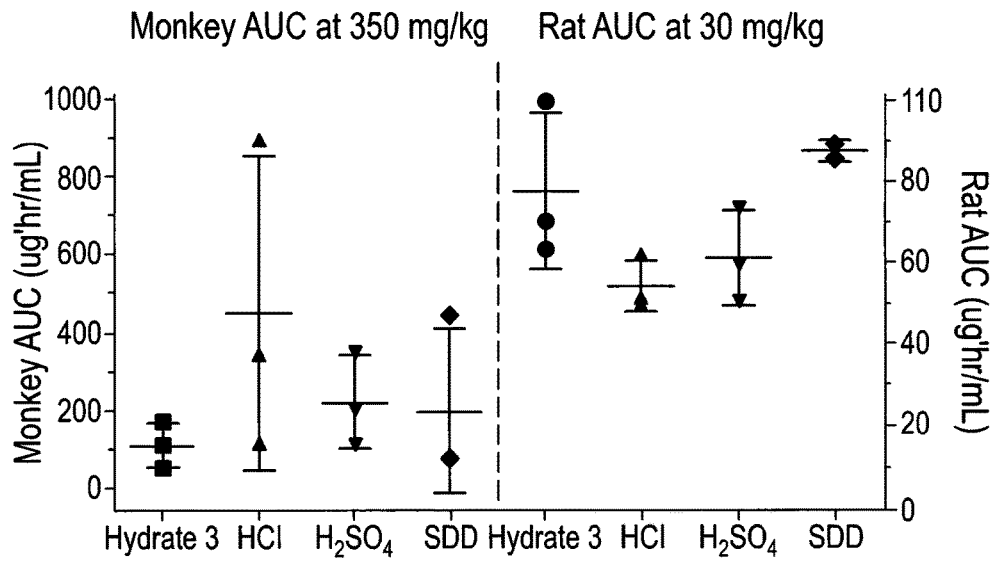
FIG. 29 is a plot of AUC for in vivo exposures of Hydrate 3 of Compound (1) compared to exposures of the corresponding HCl salt, $H_2SO_4$ salt, and SDD in monkeys and rats.

Referring to FIG. 29, no significant differences were observed in exposures. The salts and the SDD showed a higher degree of variability than Hydrate 3 of Compound (1) in the monkeys compared to the rats.

Figure 30:
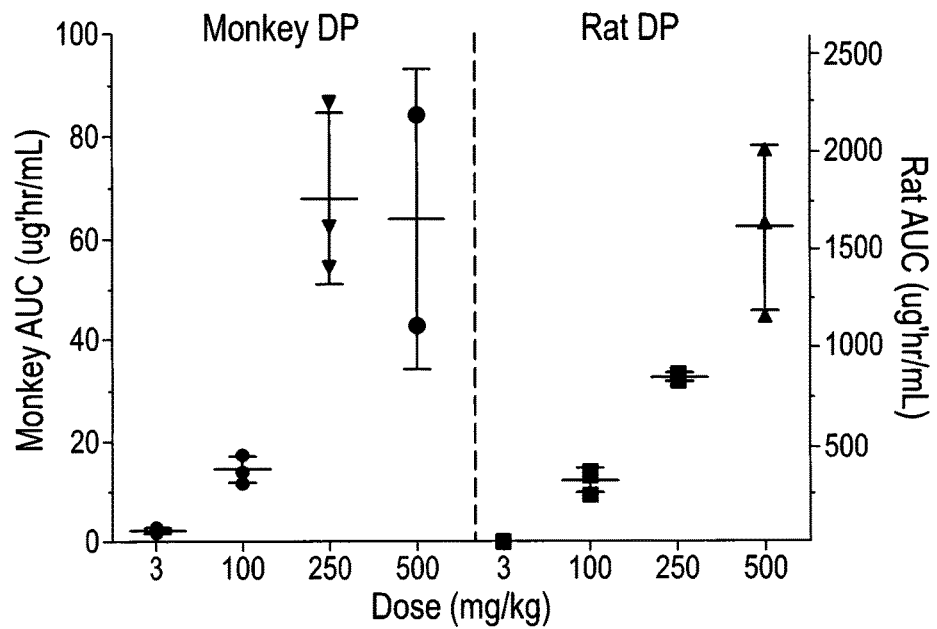
FIG. 30 is a plot of concentration vs. dose for Hydrate 3 of Compound (1) in rats and monkeys.

Referring to FIG. 30, a dose proportional study in rats and monkeys, using Hydrate 3 of Compound (1) as a suspension in 0.5% MC showed a proportional increase in exposures with respect to dose in rats up to 500 mg/kg. A dose proportional increase was observed in monkeys up to 250 mg/kg, above which a plateau was observed in the exposures.

Example 15: Toxicology Formulation Stability

Hydrate 3 of Compound (1) was evaluated for chemical stability and homogeneity in 0.5% MC in water (suspension) at 1, 60 mg/mL and 100 mg/mL under ambient and refrigerated conditions (5° C.) for two weeks. The samples were evaluated by HPLC (% area and assay) and no changes were observed in purity (% Area), with % recovery within 85-115% of all samples. The results demonstrate stability and homogeneity (average particle size lower than 50 μm) over the two week time period.

Example 16: Compound (1) Activity Against Test Panel of Influenza Type A and Type B Strains Compound (1) showed potent, broad spectrum antiviral activity in a 3-day CP assay in MDCK cells infected with a panel of influenza type A (H1N1, H3N2, and H3N8) viral strains, with an average EC50 of 4.3 nM (SD 5.7 nM, N=39, Table 21). The panel included strains that are resistant to commercially available neuraminidase and matrix protein 2 (M2) inhibitors (N=5, and N=22, respectively). Compound (1) is active against both the highly pathogenic avian influenza H5N1 strain A/VN/1203/2004 and the pandemic swine origin H1N1 strain A/CA/07/2009, with EC50 values for Compound (1) of 4.2 nM and 4.0 nM, respectively. A comparison of the activity of Compound (1) with that of amantadine, oseltamivir, zanamivir and favipiravir (T-705, a competitor compound currently in clinical trials) is shown in Table 20.

TABLE 20

Comparative activity for Compound (1).

| | Compound (1) $EC_{50}$ nM (SD) | Oseltamivir Carboxylate $EC_{50}$ μM (SD) | Zanamivir $EC_{50}$ μM (SD) | T-705 $EC_{50}$ μM (SD) | Amantadine $EC_{50}$ μM (SD) |
|---|---|---|---|---|---|
| Influenza A Strains | | | | | |
| A/WS/33 | 2.4 (1.1) | >10 (ND) | >10 (ND) | >10 (ND) | >10 (ND) |
| A/NWS/33 | 1.7 (0.92) | >10 (ND) | >10 (ND) | 7.6 (12.0) | >10 (ND) |
| A/Puerto Rico/8/34 | 14 (19) | >10 (ND) | >10 (ND) | >10 (ND) | >10 (ND) |
| A/Weiss/43 | 1.3 (0.30) | 0.49 (0.47) | 0.080 (0.049) | 1.5 (1.5) | >10 (ND) |
| A/FM/1/47 | 1.5 (0.57) | 6.4 (3.6) | 2.6 (3.2) | 4.5 (4.9) | 0.66 (0.73) |
| A/Mal/302/54 | 3.9 (3.0) | 1.1 (1.0) | 0.28 (0.20) | 3.4 (4.0) | 2.1 (2.9) |
| A/Denver/1/57 | 1.4 (0.29) | >10 (ND) | >10 (ND) | 1.1 (1.1) | 0.31 (0.12) |
| A/Aichi/2/68 | 4.4 (1.9) | 5.0 (ND) | >10 (ND) | >10 (ND) | 6.6 (4.9) |
| A/Hong Kong/8/68 | 1.9 (1.5) | 0.038 (0.025) | 0.15 (0.057) | 4.5 (6.9) | 3.7 (ND) |
| A/Port Chalmers/1/73 | 2.3 (1.8) | 0.12 (0.010) | 0.67 (0.76) | 1.9 (2.6) | >10 (ND) |
| A/Victoria/3/75 | 2.1 (1.5) | >10 (ND) | 4.1 (5.9) | >10 (ND) | 8.6 (11) |
| A/New Jersey/8/76 | 0.96 (1.3) | 3.8 (4.8) | 6.2 (4.0) | 2.1 (2.3) | 0.82 (0.25) |
| A/Wisconsin/67/2005 | 3.7 (3.8) | 0.35 (0.22) | 0.16 (0.21) | >10 (ND) | >10 (ND) |
| A/Chelyabinsk/1/200 | 3.1 (1.9) | >10 (ND) | 7.6 (ND) | 6.5 (ND) | >10 (ND) |
| A/Fukushima/141/2006 | 1.5 (1.1) | 0.58 (0.40) | 0.27 (0.23) | 1.9 (0.59) | 0.46 (0.83) |
| A/Georgia/17/2006 | 9.1 (15) | >10 (ND) | >10 (ND) | 9.6 (13) | 0.25 (0.19) |
| A/Georgia/20/2006 | 1.7 (1.9) | >10 (ND) | 4.3 (5.7) | 6.3 (5.2) | >10 (ND) |
| A/Hawaii/2/2006 | 1.2 (0.53) | >10 (ND) | >10 (ND) | 5.5 (3.4) | 9.2 (ND) |
| A/Missouri/3/2006 | 2.6 (3.1) | 2.5 (2.3) | 3.6 (3.2) | 5.3 (1.8) | 6.0 (ND) |
| A/Nebraska/1/2006 | 1.9 (0.90) | >10 (ND) | >10 (ND) | 6.4 (4.1) | >10 (ND) |
| A/Santiago/7981/2006 | 1.8 (1.3) | >10 (ND) | 4.0 (ND) | 0.86 (0.87) | >10 (ND) |
| A/St. Petersburg8/2006 | 1.3 (0.56) | 9.3 (2.4) | 6.0 (ND) | >10 (ND) | >10 (ND) |
| A/Virginia/01/2006 | 12 (8.5) | 0.83 (0.72) | 0.83 (0.82) | 3.1 (0.79) | >10 (ND) |
| A/Cambodia0371/2007 | 1.2 (1.2) | 7.8 (17) | 2.1 (ND) | 6.5 (9.1) | >10 (ND) |
| A/Henan/Jinshui/147/2007 | 19 (12) | >10 (ND) | >10 (ND) | 6.1 (1.5) | >10 (ND) |
| A/South Dakota/6/2007 | 0.52 (0.44) | 8.2 (ND) | 3.4 (ND) | 7.1 (ND) | 0.14 (0.059) |
| A/Texas/12/2007 | 30 (30) | 8.5 (ND) | 8.2 (ND) | 7.1 (2.3) | >10 (ND) |
| A/Uruguay/716/2007 | 1.0 (1.0) | >10 (ND) | 4.7 (ND) | 4.5 (ND) | >10 (ND) |
| A/California/07/2009 | 4.0 (4.4) | >10 (ND) | >10 (ND) | 2.0 (1.1) | >10 (ND) |
| A/California/07/2009 NYMC, X-179A | 10 (8.7) | >10 (ND) | 5.6 (2.7) | >10 (ND) | >10 (ND) |
| A/Mexico/4108/2009 | 3.7 (4.2) | >10 (ND) | 3.8 (ND) | >10 (ND) | >10 (ND) |

TABLE 20-continued

Comparative activity for Compound (1).

| | Compound (1) EC$_{50}$ nM (SD) | Oseltamivir Carboxylate EC$_{50}$ μM (SD) | Zanamivir EC$_{50}$ μM (SD) | T-705 EC$_{50}$ μM (SD) | Amantadine EC$_{50}$ μM (SD) |
|---|---|---|---|---|---|
| A/New York/18/2009 | 1.4 (0.86) | 0.16 (0.26) | 0.31 (0.46) | 1.3 (0.55) | >10 (ND) |
| A/Texas/48/2009 | 1.2 (0.60) | >10 (ND) | 1.7 (0.28) | 9.3 (3.3) | >10 (ND) |
| A/Virginia/ATCC2/2009 | 1.4 (0.82) | >10 (ND) | >10 (ND) | 5.3 (ND) | >10 (ND) |
| A/Virginia/ATCC3/2009 | 1.2 (0.40) | >10 (ND) | >10 (ND) | 7.7 (ND) | >10 (ND) |
| Influenza A Animal Strains | | | | | |
| A/Swine/Iowa/15/30 | 4.3 (4.8) | 7.8 (0.071) | 1.8 (0.071) | >10 (ND) | 0.22 (ND) |
| A/Swine/1976/31 | 5.2 (11) | 0.56 (0.13) | 0.25 (0.14) | >10 (ND) | 0.078 (0.0071) |
| A/Equine/Miami/63 | 3.7 (5.9) | 0.25 (0.14) | 0.93 (0.38) | >10 (ND) | 1.75 (0.071) |
| Influenza A HPAIV (H5N1) | | | | | |
| A/VN/1203/2004 | 4.2 (ND) | ND | ND | ND | ND |
| Influenza B Strains | | | | | |
| B/Lee/40 | >10,000 (ND) | >10 (ND) | >10 (ND) | 6.5 (5.7) | >10 |
| B/Mass/3/66 | >10,000 (ND) | 6.7 (ND) | ND | 3.4 | ND |
| B/Russia/69 | >10,000 (ND) | 6.0 (ND) | 3.1 (ND) | 0.29 | >10 |
| B/Memphis/20/1996--070 | >10,000 (ND) | >10 (ND) | 2.6 (ND) | 2.4 (1.5) | >10 |
| B/Memphis/20/1996--071 | >10,000 | >10 (ND) | 6.0 (ND) | >10 (ND) | ND |

EC50: effective concentration at which ATP is half the maximum in the CPE-based assay; ND: not determined; SD: standard deviation.

Example 17: In Vivo Assay for Combination of Compound (1) with or without Oseltamivir Influenza A Model Referring to FIG. 32, the potential for a positive therapeutic interaction between Compound (1) and oseltamivir against influenza A was explored in the mouse model. Mice were challenged with influenza A and dosed with vehicle (10 mL/kg 0.5% MC) or Compound (1) at 1, 3, 10, or 30 mg/kg BID alone, or in combination with 10 mg/kg BID oseltamivir. Therapy was started 48 hours post influenza A infection and continued for 10 days. All of the vehicle-treated controls succumbed to disease by study day 8 (Table 21).

TABLE 21

In Vivo Efficacy Data of Compound (1) with or without Oseltamivir Administered + 48 Hours After Influenza A Infection.

| | | Percent Survival Compound (1) (mg/kg BID) | | | | |
|---|---|---|---|---|---|---|
| | | 0 | 1 | 3 | 10 | 30 |
| Oseltamivir (mg/kg BID) | 0 | 0% | 0% | 75% | 100% | 100% |
| | 10 | 0% | 87.5% | 100% | 100% | 100% |

Treatment with Compound (1) at 10 or 30 mg/kg BID alone provided complete protection from mortality. In contrast, treatment with Compound (1) at 3 mg/kg BID alone provided a partial survival benefit and 1 mg/kg BID Compound (1) or 10 mg/kg oseltamivir administered alone failed to protect mice from influenza infection in this study. Interestingly, the combinations of 1 or 3 mg/kg BID Compound (1) with 10 mg/kg oseltamivir dosed BID provided increased protection from mortality compared to the single agents. These data imply a synergistic effect of the Compound (1) and oseltamivir combination.

Figure 32:
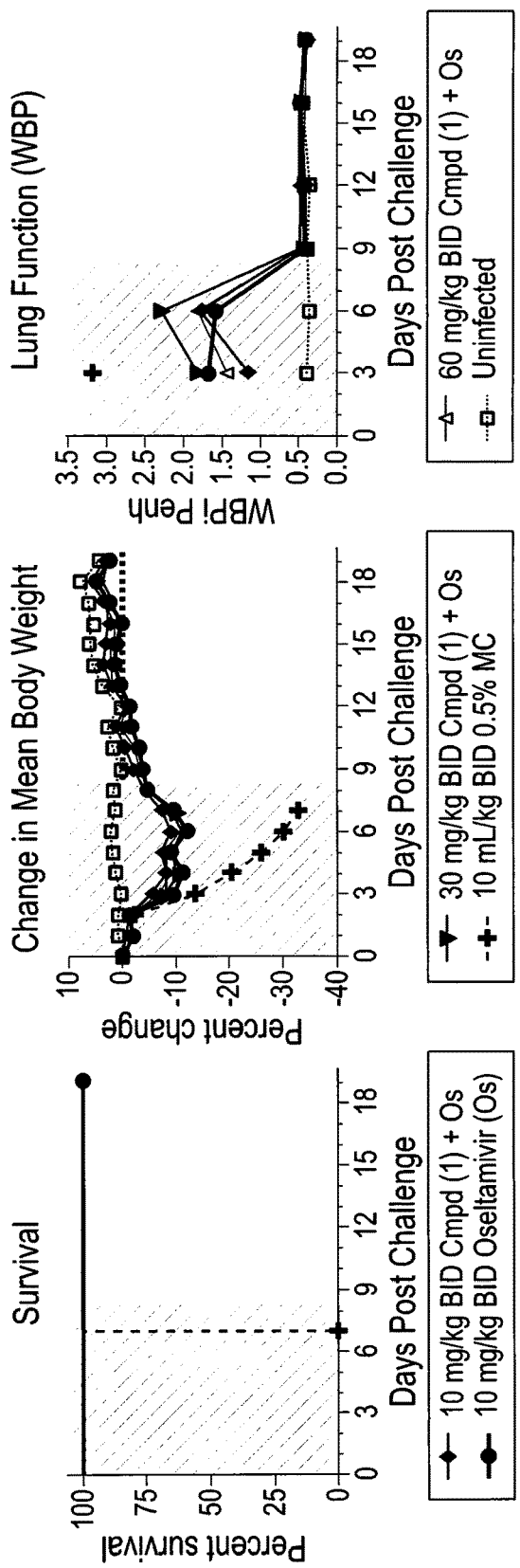
FIG. 32 is a plot of survival, change in mean body weight, and lung function vs. days post challenge for Compound (1) and oseltamivir combination therapy.
Figure 33:
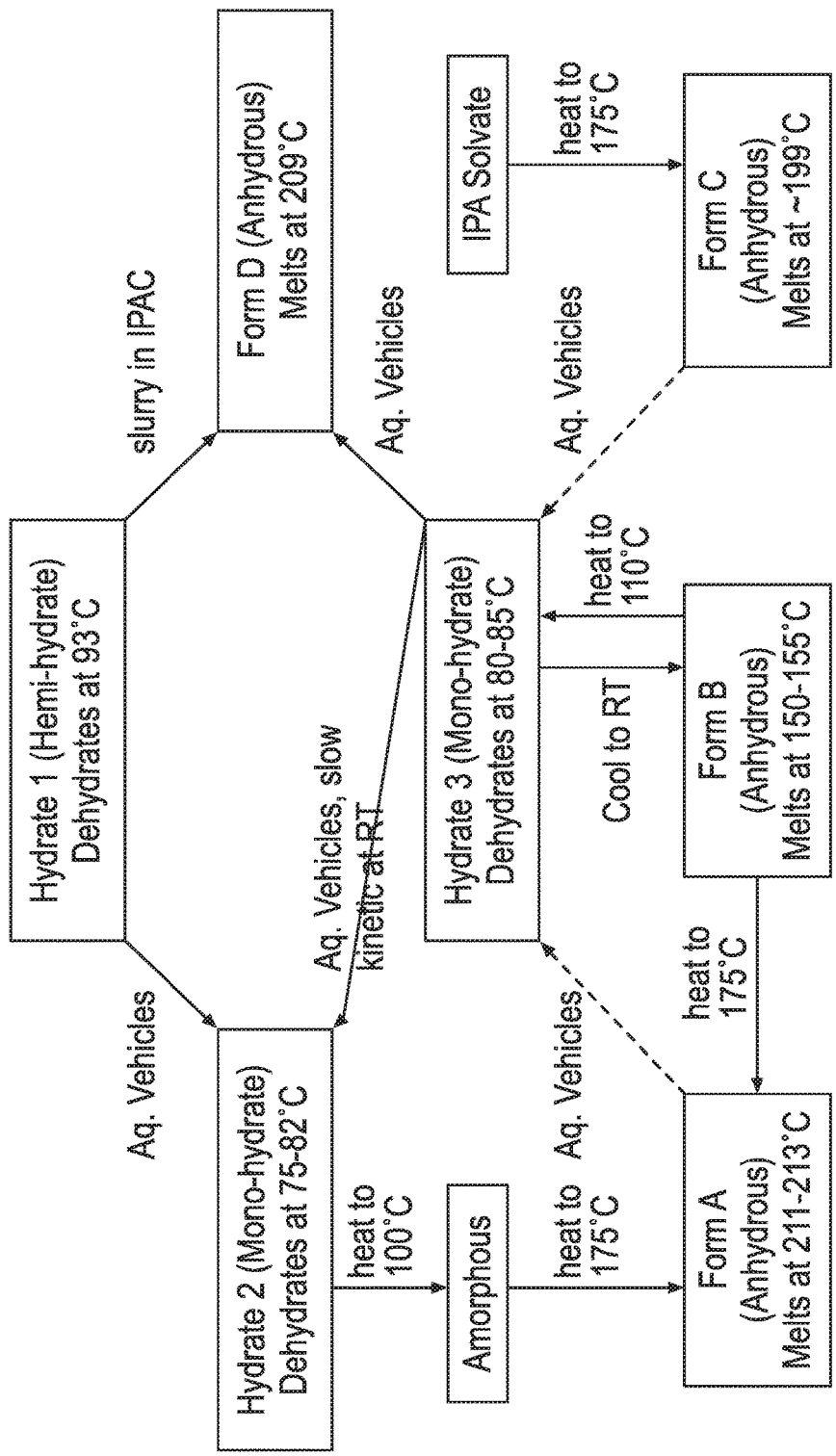
FIG. 33 is an illustration of a chemical scheme for the interconversion of polymorphic forms of Compound (1).

Influenza B Model:

The consequence of combining Compound (1) and oseltamivir was explored in the influenza B mouse model. Mice were dosed prophylactically with vehicle (10 mL/kg 0.5% MC), 10 mg/kg oseltamivir, or oseltamivir in combination with Compound (1) at 10 mg/kg, 30 mg/kg or 60 mg/kg BID and treatment continued for 10 days. All of the vehicle-treated controls succumbed to disease by study day 7 as shown in FIG. 32. Consistent with a lack of Compound (1) activity against influenza B, treatment with 10, 30 mg/kg or 60 mg/kg BID Compound (1) in combination with oseltamivir (Os) at 10 mg/kg BID provided the same survival benefit and protection from BW and lung function loss as oseltamivir treatment alone (FIG. 32). There was no negative interaction when Compound (1) was added to oseltamivir therapy.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polymorphic form of Compound (1) or a pharmaceutically acceptable salt thereof, wherein Compound (1) is represented by the following structural formula:

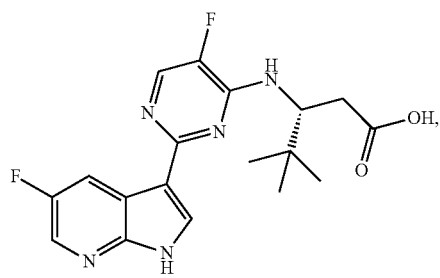 [SMILES: CC(C)(C)[C@@H](CC(=O)O)Nc1nc(-c2c[nH]c3ncc(F)cc23)ncc1F]

and wherein the polymorphic form is selected from the group consisting of: Hydrate 2 of Compound (1) and Hydrate 3 of Compound (1), wherein Hydrate 2 of Compound (1) is characterized by one or more peaks corresponding to 2-theta values, measured in degrees, of 6.9±0.2, 7.9±0.2, 13.8±0.2, 15.9±0.2, 20.9±0.2, and 23.4±0.2 in an X-ray powder diffraction pattern and wherein Hydrate 3 of Compound (1) is characterized by one or more peaks corresponding to 2-theta values, measured in degrees, of 7.0±0.2, 18.6±0.2, 20.8±0.2, 23.3±0.2, and 26.0±0.2 in an X-ray powder diffraction pattern.

2. The polymorphic form of claim 1, wherein the polymorphic form is Hydrate 2 of Compound (1), and wherein Hydrate 2 of Compound (1) is further characterized by one or more peaks corresponding to 2-theta values, measured in degrees, of 17.1±0.2, 18.6±0.2, 22.1±0.2 and 29.2±0.2 in an X-ray powder diffraction pattern.

3. The polymorphic form of claim 1, wherein the polymorphic form is Hydrate 2 of Compound (1), and wherein Hydrate 2 of Compound (1) is further characterized by a $^{13}$C SSNMR spectrum of 178.5 ppm, 137.2 ppm, 126.8 ppm, 107.0 ppm, and 35.3 ppm.

4. The polymorphic form of claim 1, wherein the polymorphic form is Hydrate 3 of Compound (1), and wherein Hydrate 3 of Compound (1) is further characterized by one or more peaks corresponding to 2-theta values, measured in degrees, of 8.9±0.2, 16.6±0.2, and 28.9±0.2 in an X-ray powder diffraction pattern.

5. The polymorphic form of claim 1, wherein the polymorphic form is Hydrate 3 of Compound (1), and wherein Hydrate 3 of Compound (1) is further characterized by a $^{13}$C SSNMR spectrum of 178.8 ppm, 136.7 ppm, 107.8 ppm, 34.9 ppm, and 26.3 ppm.

6. A pharmaceutical composition comprising a polymorphic form of Compound (1) according to claim 1, and at least one pharmaceutically acceptable carrier or excipient.

7. A method of reducing the amount of influenza viruses in a biological in vitro sample or in a subject, comprising administering to the sample or subject an effective amount of a polymorphic form of Compound (1) according to claim 1.

8. A method of inhibiting the replication of influenza viruses in a biological in vitro sample or in a subject, comprising administering to the sample or subject an effective amount of a polymorphic form of Compound (1) according to claim 1.

9. A method of treating influenza infection in a subject, comprising administering to the subject a therapeutically effective amount of a polymorphic form of Compound (1) according to claim 1.

10. The method of claim 7, further comprising co-administering one or more additional therapeutic agents to the sample or subject.

11. The method of claim 10, wherein the additional therapeutic agents include an anti-virus drug.

12. The method of claim 11, wherein the anti-virus drug is a neuraminidase inhibitor or a polymerase inhibitor.

13. The method of claim 12, wherein the neuraminidase inhibitor is oseltamivir or zanamivir.

14. The method of claim 12, wherein the polymerase inhibitor is flavipiravir.

15. The method of claim 9, wherein the influenza infection is an influenza A virus infection.

16. A method of preparing Hydrate 2 of Compound (1), wherein Compound (1) is represented by the following structural formula:

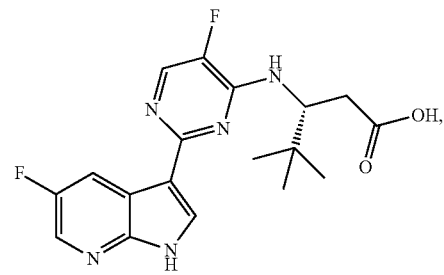 [SMILES: CC(C)(C)[C@@H](CC(=O)O)Nc1nc(-c2c[nH]c3ncc(F)cc23)ncc1F]

and Hydrate 2 of Compound (1) is characterized by one or more peaks corresponding to 2-theta values, measured in degrees, of 6.9±0.2, 7.9±0.2, 13.8±0.2, 15.9±0.2, 20.9±0.2, and 23.4±0.2 in an X-ray powder diffraction pattern, comprising:
mixing Hydrate 1 of Compound (1) with a solvent system comprising water to generate a mixture; and
removing at least some of the solvent system from the mixture to generate Hydrate 2 of Compound (1).

17. The method of claim 16, wherein the solvent system further comprises chlorobenzene, cyclohexane, 1,2-dichloroethene, dichloromethane, 1,2-dimethoxyethane, N,N-dimentylacetamide, N,N-dimethylformamide, 1,4-dioxane, 2-ethoxyethanol, formamide, hexane, 2-methoxyethanol, methylbutyl ketone, methylcyclohexane, N-methylpyrrolidone, nitromethane, pyridine, sulfolane, tetrahydrofuran, methyl tetrahydrofuran, tetralin, tolune, 1,1,2-trichloroethene, xylene, acetic acid, acetone, anisole, 1-butanol, 2-butanol, butyl acetate, tert-butylmethyl ether, cumene, heptane, isobutyl acetate, isopropyl acetate, methyl acetate, 3-methyl-1-butanol, methylethyl ketone, methylisobutyl ketone, 2-methyl-1-propanol, ethyl acetate, ethyl ether, ethyl formate, pentane, 1-pentanol, 1-propanol, 2-propanol, propyl acetate, or any combination thereof.

18. The method of claim 16, wherein the solvent system further comprises chlorobenzene, cyclohexane, 1,2-dichloroethane, dichloromethane, 1,2-dimethoxyethane, formamide, hexane, 2-methoxyethanol, methylbutyl ketone, methylcyclohexane, nitromethane, tetralin, xylene, toluene, 1,1,2-trichloroethane, acetone, anisole, 1-butanol, 2-butanol, butyl acetate, t-butylmethylether, cumene, ethanol, ethyl acetate, ethyl ether, ethyl formate, heptane, isobutyl acetate, isopropyl acetate, methyl acetate, 3-methyl-1-butanol, methylethyl ketone, 2-methy-1-propanol, pentane, 1-propanol, 1-pentanol, 2-propanol, propyl acetate, tetrahydrofuran, methyl tetrahydrofuran, or any combination thereof.

19. The method of claim 16, wherein the solvent system further comprises 2-ethoxyethanol, ethyleneglycol, methanol, 2-methoxyethanol, 1-butanol, 2-butanol, 3-methyl-1-butanol, 2-methyl-1-propanol, ethanol, 1-pentanol, 1-propanol, 2-propanol, methylbutyl ketone, acetone, methylethyl ketone, methylisobutyl ketone, butyl acetate, isobutyl acetate, isopropyl acetate, methyl acetate, ethyl acetate, propyl acetate, pyridine, toluene, xylene, or any combination thereof.

20. The method of claim 16, wherein the solvent system further comprises acetone, n-propanol, isopropanol, isobutylacetate, acetic acid, or any combination thereof.

21. The method of claim 16, wherein the solvent system includes water and acetone, or water and isopropanol.

22. The method of claim 16, wherein the solvent system further comprises sodium chloride, dextrose, glycerine, or a surfactant.

23. The method of claim 16, wherein the mixing is performed at a temperature in a range from 20° C. to less than 40° C.

24. The method of any claim 16, further comprising applying a vacuum to the mixture to remove the solvent system.

25. A method of preparing Hydrate 3 of Compound (1), wherein Compound 1 is represented by the following structural formula:

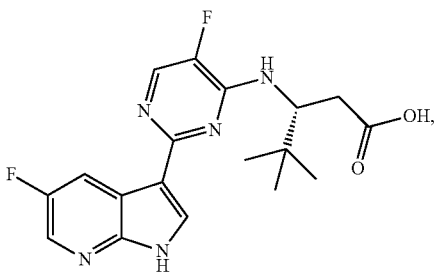 [SMILES: CC(C)(C)[C@@H](CC(=O)O)Nc1nc(-c2c[nH]c3ncc(F)cc23)ncc1F]

and wherein Hydrate 3 of Compound (1) is characterized by one or more peaks corresponding to 2-theta values, measured in degrees, of 7.0±0.2, 18.6±0.2, 20.8±0.2, 23.3±0.2, and 26.0±0.2 in an X-ray powder diffraction pattern, comprising:
mixing Hydrate 1 of Compound (1) or amorphous Compound (1) with a solvent system comprising water to generate a mixture;
heating the mixture; and
removing at least some of the solvent system to generate Hydrate 3 of Compound (1).

26. The method of claim 25, wherein the solvent system further comprises acetonitrile, chlorobenzene, cyclohexane, 1,2-dichloroethene, dichloromethane, 1,2-dimethoxyethane, N,N-dimentylacetamide, N,N-dimethylformamide, 1,4-dioxane, 2-ethoxyethanol, formamide, hexane, 2-methoxyethanol, methylbutyl ketone, methylcyclohexane, N-methylpyrrolidone, nitromethane, pyridine, sulfolane, tetrahydrofuran, tetralin, tolune, 1,1,2-trichloroethene, xylene, acetic acid, acetone, anisole, 1-butanol, 2-butanol, butyl acetate, tert-butylmethyl ether, cumene, heptane, isobutyl acetate, isopropyl acetate, methyl acetate, 3-methyl-1-butanol, methylethyl ketone, methylisobutyl ketone, 2-methyl-1-propanol, ethyl acetate, ethyl ether, ethyl formate, pentane, 1-pentanol, 1-propanol, 2-propanol, propyl acetate, or any combination thereof.

27. The method of claim 25, wherein the solvent system further comprises chlorobenzene, cyclohexane, 1,2-dichloroethane, dichloromethane, 1,2-dimethoxyethane, formamide, hexane, 2-methoxyethanol, methylbutyl ketone, methylcyclohexane, nitromethane, tetralin, xylene, toluene, 1,1,2-trichloroethane, acetone, anisole, 1-butanol, 2-butanol, butyl acetate, t-butylmethylether, cumene, ethanol, ethyl acetate, ethyl ether, ethyl formate, heptane, isobutyl acetate, isopropyl acetate, methyl acetate, 3-methyl-1-butanol, methylethyl ketone, 2-methy-1-propanol, pentane, 1-propanol, 1-pentanol, 2-propanol, propyl acetate, tetrahydrofuran, methyl tetrahydrofuran, or any combination thereof.

28. The method of claim 25, wherein the solvent system further comprises 2-ethoxyethanol, ethyleneglycol, methanol, 2-methoxyethanol, 1-butanol, 2-butanol, 3-methyl-1-butanol, 2-methyl-1-propanol, ethanol, 1-pentanol, 1-propanol, 2-propanol, methylbutyl ketone, acetone, methylethyl ketone, methylisobutyl ketone, butyl acetate, isobutyl acetate, isopropyl acetate, methyl acetate, ethyl acetate, propyl acetate, pyridine, toluene, xylene, or any combination thereof.

29. The method of claim 25, wherein the solvent system further comprises isopropanol, acetonitrile, acetone, or any combination thereof.

30. The method of claim 25, where in the mixture is heated to a temperature of from about 45° C. to about 55° C.

31. The method of claim 25, further comprising applying a vacuum to the mixture to remove the solvent system.

32. A dosage regimen for treating influenza virus infection in a subject comprising administering to the subject a polymorphic form of Compound (1) or a pharmaceutically acceptable salt thereof according to claim 1 in a dosage amount of 100 mg to 1,600 mg, wherein the dosage amount is administered once, twice, or three times per day.

33. The dosage regimen of claim 32, wherein the dosage amount is 300 mg to 1,600 mg.

34. The dosage regimen of claim 33, wherein the dosage amount is 600 mg to 1,200 mg.

35. The dosage regimen of claim 33, wherein the dosage is administered once per day.

36. The dosage regimen of claim 34, wherein the dosage amount is 600 mg or 800 mg.

37. The dosage regimen of claim 33, wherein the dosage amount is 300 mg to 900 mg.

38. The dosage regimen of claim 37, wherein the dosage is administered twice per day.

39. The dosage regimen of claim 32, wherein the dosage amount is 400 mg or 600 mg.

40. The dosage regimen of claim 32, wherein Compound (1) or a pharmaceutically acceptable salt thereof is administered for a treatment duration of 1 day to an entire flu season.

41. The dosage regimen of claim 40, wherein the treatment duration is 3 days to 14 days.

42. The dosage regimen of claim 41, wherein the treatment duration is 3 days, 4 days, or 5 days.

43. The dosage regimen of claim 40, wherein a loading dosage amount of 600 mg to 1,600 mg is administered to the subject on day 1 and a dosage amount of 400 mg to 1,200 mg is administered to the subject for the rest of the treatment duration.

44. The dosage regimen of claim 43, wherein a loading dosage amount of 900 mg to 1,600 mg is administered to the subject on day 1 and a dosage amount of 400 mg to 1,200 mg is administered to the subject for the rest of the treatment duration.

45. The dosage regimen of claim 44, wherein a loading dosage amount of 900 mg or 1,200 mg is administered to the subject on day 1 and a dosage amount of 600 mg to 800 mg is administered to the subject for the rest of the treatment duration.

46. The dosage regimen of claim 45, wherein a loading dosage amount of 900 mg is administered to the subject on day 1 and a dosage amount of 600 mg is administered once a day to the subject for the rest of the treatment duration.

47. The dosage regimen of claim 45, wherein a loading dosage amount of 1,200 mg is administered to the subject on day 1 and a dosage amount of 600 mg is administered once a day to the subject for the rest of the treatment duration.

* * * * *